(12) United States Patent
Ding et al.

(10) Patent No.: US 7,297,551 B2
(45) Date of Patent: Nov. 20, 2007

(54) RECOMBINANT PROTEINS AND PEPTIDES FOR ENDOTOXIN BIOSENSORS, ENDOTOXIN REMOVAL, AND ANTI-MICROBIAL AND ANTI-ENDOTOXIN THERAPEUTICS

(75) Inventors: Jeak L. Ding, Singapore (SG); BoW Ho, Singapore (SG); Nguan S. Tan, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 10/638,125

(22) Filed: Aug. 7, 2003

(65) Prior Publication Data

US 2004/0175388 A1    Sep. 9, 2004

Related U.S. Application Data

(60) Division of application No. 09/626,795, filed on Jul. 26, 2000, now Pat. No. 6,719,973, which is a continuation-in-part of application No. 09/219,868, filed on Dec. 24, 1998, now abandoned.

(60) Provisional application No. 60/159,569, filed on Oct. 15, 1999.

(51) Int. Cl.
    G01N 1/00      (2006.01)
    G01N 33/566    (2006.01)
    G01N 33/00     (2006.01)
    C02F 3/34      (2006.01)
    C12Q 1/00      (2006.01)

(52) U.S. Cl. ............... 436/177; 435/4; 435/7.1; 435/7.2; 435/7.92; 435/7.95; 435/13; 435/29; 435/32; 435/34; 435/39; 435/69.1; 435/69.8; 435/262; 435/440; 436/174; 436/175; 436/501

(58) Field of Classification Search ............ 435/4, 435/7.2, 7.3, 7.31, 7.32, 13, 30, 71.2, 71.3, 435/174, 183, 221, 224; 436/45, 86, 161, 436/162, 172, 177; 530/413, 417, 418; 424/124
See application file for complete search history.

(56) References Cited

U.S. PATENT DOCUMENTS

| | | | |
|---|---|---|---|
| 5,439,807 A | 8/1995 | Grinna | |
| 5,565,362 A | 10/1996 | Rosen | |
| 5,648,244 A | 7/1997 | Kuliopulos et al. | |
| 5,712,144 A | 1/1998 | Ding | |
| 5,858,706 A | 1/1999 | Ding et al. | |
| 5,985,590 A * | 11/1999 | Ding et al. | 435/23 |
| 6,719,973 B1 * | 4/2004 | Ding et al. | 424/185.1 |

FOREIGN PATENT DOCUMENTS

| | | |
|---|---|---|
| WO | WO 99/15676 | 4/1999 |
| WO | WO 00/26366 | 5/2000 |

OTHER PUBLICATIONS

Ding et al. 1995. Mol. Marine. Bio. and Biotech. 4(1): 90-103.*
Dwarakanath et al. Nov. 1997. Biotech. Letters. 19(11): 1147-1150.*
Muta et al. 1991. J. Biol. Chem. 266(10):6554-6561.*
Alberts et al., Molecular biology of the Cell. 1994. p. 557-560.*
Ding et al., "Expression of full length and deletion homologues of *Carcinoscorpius rotundicauda* Factor C in *Saccharomyces cerevisiae*: immunoreactivity and endotoxin binding," *J. Endotoxin Res.* 4(1):33-43, 1997.
Pui et al., "Recombinant Factor C from *Carcinoscorpius rotundicauda* binds endotoxin," *New Developments on Marine Biotechnology* (ed. Le Gal and Halvorson), Plenum Press, New York, pp. 151-154, 1998.
Roopashree et al., "Expression of *Carcinoscorpius rotundicauda* Factor C in *Pichia pastoris*," *Mol. Marine Biol. and Biotech.* 5(4):334-343, 1996.
Alberts et al., *Molecular Biology of the Cell*, pp. 557-560, 1994.
Ding et al., "Molecular cloning and sequence analysis of factor C cDNA from the Singapore horseshoe crab, *Carcinoscorpius rotundicauda*," *Mol. Mar. Biol. and Biotechnol.* 4(1):90-103, 1995.
Dwarakanath et al., "The Cys-rich and EGF-like domains of *Carcinoscorpius rotundicauda* Factor C yields soluble fusion protein with GFP," *Biotech. Lett.* 19(11):1147-1150, 1997.

Muta et al., "Limulus Factor C, an endotoxin-sensitive serine protease zymogen with a mosaic structure of complement-like, epidermal growth factor-like, and lectin-like domains," *J. Biol. Chem.* 266(10)6554-6561, 1991.

Pul et al., "Yeast recombinant Factor C from horseshoe crab binds endotoxin and causes bacteriostasis," *J. Endotox. Res.* 4(6):391-406, 1997.

Tan et al., "Definition of endotoxin binding sites in horseshoe crab Factor C recombinant sushi proteins and neutralization of endotoxin by sushi peptieds," *FASEB Journal* : 14(12):1801-1813, 2000.

Tan et al., "High-affinity LPS binding domain(s) in recombinant factor C of a horseshoe crab neutralizes LPS-induced lethality," *FASEB Journal* 14(7):859-870, 2000.

\* cited by examiner

*Primary Examiner*—Jeffrey Siew
*Assistant Examiner*—J. Hines
(74) *Attorney, Agent, or Firm*—Klarquist Sparkman, LLP

(57) ABSTRACT

Recombinant fragments of Factor C are disclosed. These proteins and peptides show great potency in recognizing, binding to, neutralizing and removing endotoxin. These molecules can thus be used for anti-microbial, anti-endotoxin, and anti-sepsis therapy. SSCrFCES is a 38 kDa protein representing the LPS-binding domain of Factor C. The ability of SSCrFCES to bind lipid A was analyzed using an ELISA-based assay as well as surface plasmon resonance. Surface plasmon resonance similarly carried out for SSCrFC-sushi-1,2,3-GFP, SSCrFC-sushi-1GFP, and SSCrFC-sushi-3GFP confirmed their superior affinity for endotoxin. The 50% endotoxin-neutralizing concentration of SSCrFCES against 200 EU of endotoxin is 0.069 μM, suggesting that SSCrFCES is an effective inhibitor of LAL coagulation cascade. Although partially attenuated by human serum, as low as 1 μM of SSCrFCES inhibits the LPS-induced secretion of hTNF-α and hIL-8 by THP-1 and human pheripheral blood mononuclear cells with a potency more superior than polymyxin B. SSCrFCES is non-cytotoxic, with a clearance rate of 4.7 ml/minute. The $LD_{90}$ of SSCrFCES for LPS lethality in mice is achieved at 2 μM. These results demonstrate the endotoxin-neutralizing capability of SSCrFCES in vitro and in vivo, as well as its potential for use in the treatment of endotoxin-induced septic shock. Also embodied in this application is the use of the sushi peptides and their mutant derivatives as potent antimicrobials. Further embodied in this application is the use of sushi peptides or sushi recombinant proteins to remove endotoxin from liquids.

36 Claims, 34 Drawing Sheets

```
         BHBHB          BHBHB
V1: Acetyl-C-VKVKVKV-GSG-VKVKVKV-C-NH2             SEQ ID NO:15
         BHPHB          BHPHB
V2: Acetyl-C-VKVSVKV-GSG-VKVSVKV-C-NH2             SEQ ID NO:16
```

Fig. 11A

| | | | |
|---|---|---|---|
| S1 | GFKLKGMARISCLPNGQWSNFPPKCIRECAMVSS | (S171-204) | SEQ ID NO:5 |
| S1Δ | GFKLKGKAKISCLPNGQWSNFPPKCIRECAMVSS | (S171-204@177,179) | SEQ ID NO:6 |
| S3 | HAEHKVKIGVEQKYGQFPQGTEVTYTCSGNYFLM | (S268-301) | SEQ ID NO:7 |
| S3Δ | HAEHKVKIKVKQKYGQFPQGTEVTYTCSGNYFLM | (S268-304@276,278) | SEQ ID NO:8 |
| S4 | RAEHKVKKIVKQLYGQFRQLTRVTRTCSRFLRRM | | SEQ ID NO:9 |
| S5 | HKVKKIVKQLYRAEHKVKKIVKQL | | SEQ ID NO:10 |
| S6-vg1 | MRKLVLALAKALAKVDKKNL | | SEQ ID NO:11 |
| S7-vg2 | LLNAVPHKATHAALKFLKEK | | SEQ ID NO:12 |
| S8-vg3 | GVSTTVLNIYRGIINLLQLNVKK | | SEQ ID NO:13 |
| S9-vg4 | IYRGIINLIQLAVKKAQNVYQM | | SEQ ID NO:14 |

Fig. 11B

Sushi peptides puncture holes (*P. aeruginosa* & *K. pneumoniae*) into or "de-coat" (*H. pylori*) these multiple antibiotic-resistant strains of bacteria.

An example of FITC-LPS bound to SΔ3-peptide coupled Agarose CL-6B beads viewed under microscope. (A) Bright field observation. (B) UV light fluorescence mircosopic view. (C) Beads treated with 1% DOC and observed under UV light - negligible FITC-LPS remained on the bead.

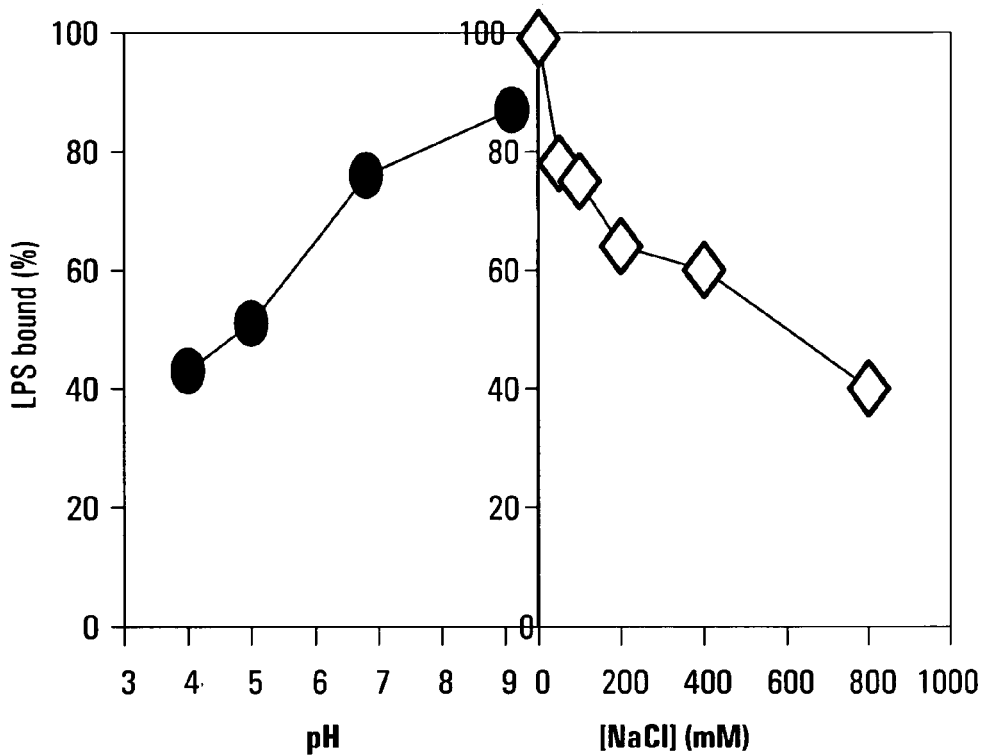

A. Binding efficiency of LPS to the affinity beads under different pH conditions.

B. binding efficiency of LPS to the affinity beads under different ionic strength.

Test of binding of LPS to the peptide affinity beads under different conditions. (A) Different pH: pH 4.0, 5.0 (20 mM sodium acetate), pH 6.8 and pH 9.1 (20 mM Tris-HCl). All buffers were supplemented with 50 mM NaCl. (B) Different ionic strength: 20 mM Tris-HCl (pH 6.8) were supplemented with different concentrations of NaCl, except for the 0 mM point which is in pyrogen-free water as control.

Fig. 18

Lipid A strips

Lipid A strips

RECOMBINANT PROTEINS AND PEPTIDES FOR ENDOTOXIN BIOSENSORS, ENDOTOXIN REMOVAL, AND ANTI-MICROBIAL AND ANTI-ENDOTOXIN THERAPEUTICS

CROSS-REFERENCES TO RELATED APPLICATIONS

This is a divisional of U.S. patent application Ser. No. 09/626,795, filed Jul. 26, 2000, now issued as U.S. Pat. No. 6,719,973, which is a continuation-in-part of U.S. patent application Ser. No. 09/219,868, filed Dec. 24, 1998, now abandoned, and which claims the benefit of U.S. Provisional Application No. 60/159,569 filed Oct. 15, 1999. The entire disclosure of each of 09/219,868 and 60/159,569 are hereby expressly incorporated by reference.

FIELD OF THE INVENTION

The present invention relates to the use of recombinant polypeptides and synthetic peptides derived from a horseshoe crab Factor C as well as computationally designed peptide analogues, all of which have endotoxin-binding domain(s). The recombinant proteins may be expressed from insect cell clones, either as is or as fusion proteins, e.g. with green fluorescent protein (GFP). The extreme sensitivity of the present recombinant Factor C to LPS, with its unique LPS-binding domains which have unsurpassed binding affinity for LPS, may be exploited in accordance with the present invention for anti-endotoxin and anti-microbial therapeutics as well as for the tracing, detection, and removal of LPS or gram-negative bacteria. The present invention also relates to a method for treating bacterial infection of a subject by inducing bacteriostasis by administration of a recombinant Factor C protein.

BACKGROUND OF THE INVENTION

Endotoxin, also known as lipopolysaccharide (LPS), is an integral component of the gram-negative bacterial cell membrane and is responsible for many, if not all, of the toxic effects that occur during gram-negative bacterial sepsis (1). LPS is a mixture of glycolipids consisting of a variable polysaccharide domain covalently bound to a conserved glucosamine-based phospholipid known as lipid A. LPS directly stimulates host monocytes and macrophages to secrete a wide array of inflammatory cytokines that include tumor necrosis factor-$\alpha$ (TNF-$\alpha$), interleukins-1 (IL-1), and interleukin-8 (IL-8) (2). Excessive release of these cytokines by host macrophages almost assuredly contributes to organ failure and death that occur after episodes of gram-negative bacterial sepsis (3). The proinflammatory bioactivities exhibited by LPS typically reside in the lipid A moiety (4).

LPS from gram-negative bacteria induces the amoebocytes of horseshoe crabs to aggregate and degranulate. Presumably, the LPS-induced coagulation cascade represents an important defense mechanism used by horseshoe crabs against invasion by gram-negative bacteria (5). The amoebocyte lysate constituted as the *Limulus* amoebocyte lysate (LAL) test has been used for decades as a tool for detecting trace concentrations of LPS in solution (6,7). The molecular mechanism of coagulation in horseshoe crab has been established and it involves a protease cascade. This cascade is based on 3 kinds of serine protease zymogens, Factor C, Factor B, proclotting enzyme, and one clottable protein, coagulogen (8). Being the initial activator of the clotting cascade, Factor C functions as a biosensor that responds to LPS.

Despite advances in antimicrobial therapy, septic shock and other clinical complications due to Gram-negative bacterial infections continue to pose a major problem. Endotoxin or lipopolysaccharide (LPS) present on the cell wall of Gram-negative bacteria (GNB) plays an important role in the pathophysiology of these infections. It does so by mediating toxicity and also mediating release of factors like tumor necrosis factor and interleukins (40), and also by forming a rigid shield around the bacteria protecting them from the effects of antibiotics. Therefore, the detection and/or removal of LPS from the bloodstream or any parenteral solution may aid in the prevention of the inflammatory and pyrogenic effects of LPS. The lipid A component of LPS plays the most important biological role; lipid A gives rise to all the ill effects elicited by endotoxin.

A number of LPS-binding proteins have been identified. Among them are the LPS binding protein, LBP (41), and bactericidal permeability increasing protein, BPI (18,42). LBP, a 60 kDa mammalian serum protein, has a binding site with a high degree of specificity for lipid A (43). BPI, a 55 kDa protein found in human neutrophils, is capable of binding to the toxic lipid A moiety of LPS resulting in neutralization of the endotoxin (18,42,44,45).

The circulating amoebocytes of the horseshoe crab contain an array of proteins that are capable of binding and neutralizing LPS. The Limulus antilipopolysaccharide factor, LALF, an 11.8 kDa LPS-binding peptide, has been identified in the amebocytes of horseshoe crabs *Limulus polyhemus* and *Tachypleus tridentatus*. LALF has subsequently been isolated and characterized (46-49). Purified LALF has been shown to bind LPS and exhibit endotoxin neutralization (50,19,51,52). Two other LPS-binding proteins from horseshoe crab hemocytes are tachyplesin (53,54) and big defensin (55).

Factor C is a serine protease zymogen. It is the key enzyme in the *C. rotundicauda* amoebocyte lysate (CAL) that is activated by LPS to initiate the coagulation cascade (56-58). Factor C activity is the basis of a very sensitive assay for femtogram levels of endotoxin used in the quality control of pharmaceutical products (59). The importance of Factor C in the detection of endotoxin has thus led to the expression of recombinant Factor C, rFC (12,60,61,73-38), as an alternative source that should alleviate the batch-to-batch and seasonal variation in the sensitivity of detection of endotoxin which is a recognized drawback with conventional amoebocyte lysate (59-61).

SUMMARY OF THE INVENTION

Since Factor C can be activated by femtograms of LPS, it is thought that Factor C has an LPS-binding region that exhibits exceptionally high affinity for LPS. Consequently, this LPS-binding domain can be utilized to detect and remove pyrogenic contaminants in pharmaceutical products intended for parenteral administration as well as for in vivo immunohistochemical determination of endotoxin localization (9).

The LPS-binding property of Factor C resides in the amino-terminal region spanning 333 amino acids. This short region constitutes a signal peptide, a cysteine-rich region, followed by epidermal growth factor-like domain and finally 3 sushi domains. High LPS affinity, comparable to the native Factor C, requires the correct formation of 9 disulfide bonds (16). This obstacle is compounded by the presence of a cysteine-rich region. Here, for the first time, we report the expression and secretion of a functional LPS-binding domain of C. rotundicauda Factor C (SSCrFCES) via a novel secretory signal. The secretory signal (SEQ ID NO: 17) is disclosed in U.S. Pat. No. 6,733,997. The entire disclosures of U.S. Pat. No. 6,733,997 and of the provisional application upon which it is based, Ser. No. 60/106,426, are hereby expressly incorporated by reference.

Homologous Factor C zymogen cDNAs have been cloned from one of the four extant species of horseshoe crab, *Carcinoscorpius rotundicauda* (CrFC) (10). Initial attempts to express CrFC and its truncated forms in *E. coli* resulted in a non-active enzyme (11). Subsequently, CrFC was cloned and expressed in *Saccharomyces cerevisiae* and a methylotropic yeast, *Pichia pastoris*. However, neither the Factor C nor the *Saccharomyces cerevisiae* a mating factor signal sequences were capable of directing secretion of the recombinant protein into the culture media for easier purification (12). Full-length CrFC expressed in yeast was not enzymatically active although it retained endotoxin-binding properties (13).

Expression in a baculoviral system (U.S. patent application Ser. No. 09/081,767, filed May 21, 1998, now abandoned, a continuation-in-part application of which issued to U.S. Pat. No. 6,645,724) yielded recombinant Factor C (rFC) with LPS-inducible enzyme activity. The entire disclosures of Ser. No. 09/081,767 (now abandoned, a continuation-in-part application of which issued to U.S. Pat. No. 6,645,724) and of the provisional application upon which it is based, Ser. No. 60/058,816, are hereby expressly incorporated by reference. The rFC has extremely high sensitivity to trace levels of LPS (<0.005 EU/ml). Before these experiments, the LPS-binding domain of Factor C exhibiting high affinity for LPS was never before successfully expressed in a heterologous host. The difficulty in doing so was largely due to its highly complex mosaic structure. While many highly disulfide-bonded proteins, like epidermal growth factor (14) and secreted acetylcholinesterase (15), were successfully expressed, few display the kind of complexity posed by the Factor C LPS-binding domain.

A form of SSCrFCES was secreted in accordance with the present invention and was purified to homogeneity. The biological functions of the recombinant SSCrFCES were assessed by measuring the ability of the SSCrFCES to bind lipid A using an ELISA-based lipid A binding assay as well as surface plasmon resonance interaction. Other subfragments containing the LPS-binding domain(s)—e.g., SSCrFCsushi-1,2,3-GFP, SSCrFCsushi-1-GFP, SSCrFCsushi-3-GFP (fusion constructs with green fluorescent protein, GFP)—as well as synthetic peptides, e.g.; sushi-1 (S1), sushi-1Δ (S1Δ), sushi-3 (S3), and sushi-3Δ (S3Δ), each of 34 mer length, and designed variant forms of peptides bearing BHBHB and/or BHPHB (where B=basic, H=hydrophobic, P=polar amino acids)—also show strong affinity for endotoxin.

The ability of these proteins and peptides to mediate inhibition of endotoxin-induced *Limulus amoebocyte* lysate (LAL) coagulation was measured with a sensitive LAL Kinetic-QCL assay. The SSCrFCES protein and peptides were also tested for their ability to suppress LPS-induced cytokines TNF-α and IL-8) produced by THP-1 and normal human peripheral blood mononuclear cells (hPBMC). SSCrFCES and the peptides were non-cytotoxic. SSCrFCES has a clearance rate of 4.7 ml/min. We also show that low doses of SSCrFCES protein and the synthetic peptides protect galactosamine-sensitized mice from LPS-induced lethality. The peptides have strong antimicrobial potencies and can therefore be used as potent therapeutics.

The present invention thus includes treating bacterial infections by administration of proteins or peptides that will bind to endotoxins, especially endotoxins produced by gram-negative bacteria, to an infected subject. The binding is apparently mediated by the lipid A component of the endotoxin. The administered protein induces bacteriostasis (that is, inhibition of bacterial proliferation) in the subject.

A preferred embodiment of this aspect of the invention is one wherein recombinant Factor C is the administered protein. The recombinant Factor C can be a full-length Factor C protein, or any portion thereof that retains the activity of binding to lipid A. It is not necessary that the Factor C retain its serine protease enzymatic activity for the protein to be effective in the method of the invention. It may in fact be beneficial if the serine protease activity is absent.

BRIEF DESCRIPTION OF THE DRAWINGS

FIG. 1(A). Coomassie brillant blue-stained 12% reducing SDS-PAGE profile of crude and purified SSCrFCES. The recombinant protein, SSCrFCES, was effectively secreted into the culture medium of S2 cells and identified as a 38 kDa protein band. Purification using ISOPrime™ resulted in an isoelectrically homogenous SSCrFCES.

FIG. 1(B). Immunoblotting analysis was perfomed with INDIA™ His-HRP antibody and visualized using SuperSignal™ Chemiluminescence. A specific 38 kDa band, in close agreement to calculated SSCrFCES size, was identified as the only secreted and purified protein harbouring a polyhistidine tag. Exposure time, using Biomax™ film (Kodak), was limited to 5 sec. Lanes are identified as follows: 1, Low-Molecular Weight marker (Pharmacia); 2, control medium (30 μg); 3, crude SSCrFCES medium (30 μg); 4, Affinity purified SSCrFCES (1 μg); 5, ISOprime™ purified SSCrFCES (1 μg)

FIG. 2(A). SSCrFCES displayed a biphasic binding profile to lipid A measured by an ELISA-based assay. Three different concentrations of lipid A were coated overnight onto Polysorp™ plates (Nunc). Varying concentrations of SSCrFCES were allowed to interact with the immobilized lipid A. The amount of bound SSCrFCES was determined by rabbit anti-SSCrFCES IgG and quantitated by ABTS substrate. The O.D.$_{405nm}$ of the samples and reference wavelength at 490 nm were determined using a microtiter plate reader. The biphasic response is indicative of multiple binding sites for lipid A.

FIG. 2(B). SSCrFCES binds to lipid A at a stoichiometry of ~3 lipid A molecules per SSCrFCES. A plot of the molar ratio of bound SSCrFCES to immobilized lipid A, gave a value of 0.37 at saturation. This means that each SSCrFCES molecule has the ability to bind ~3 lipid A molecules.

FIG. 2(C). A Hill's plot showing Hill's coefficient, determined by the slope of the straight line obtained from plotting that data according to the Hill's equation, is 2.2. This indicates that SSCrFCES exhibited positive cooperativity in lipid A binding.

FIG. 3(A). A surface plasmon resonance (SPR) sensogram depicting the interaction of SSCrFCES, with immobilized lipid A. 800 ng/100 μl of SSCrFCES was injected which resulted in an increase of 200 relative response unit. After the dissociation phase, by passing PBS in a running buffer, INDIA™ His-HRP antibody was injected. The further increase in relative response unit clearly indicates that SSCrFCES is bound to lipid A. The surface was regenerated by a pulse of 100 mM NaOH. At all times, the flow rate was maintained at 10 μl/min.

Figure 4A:
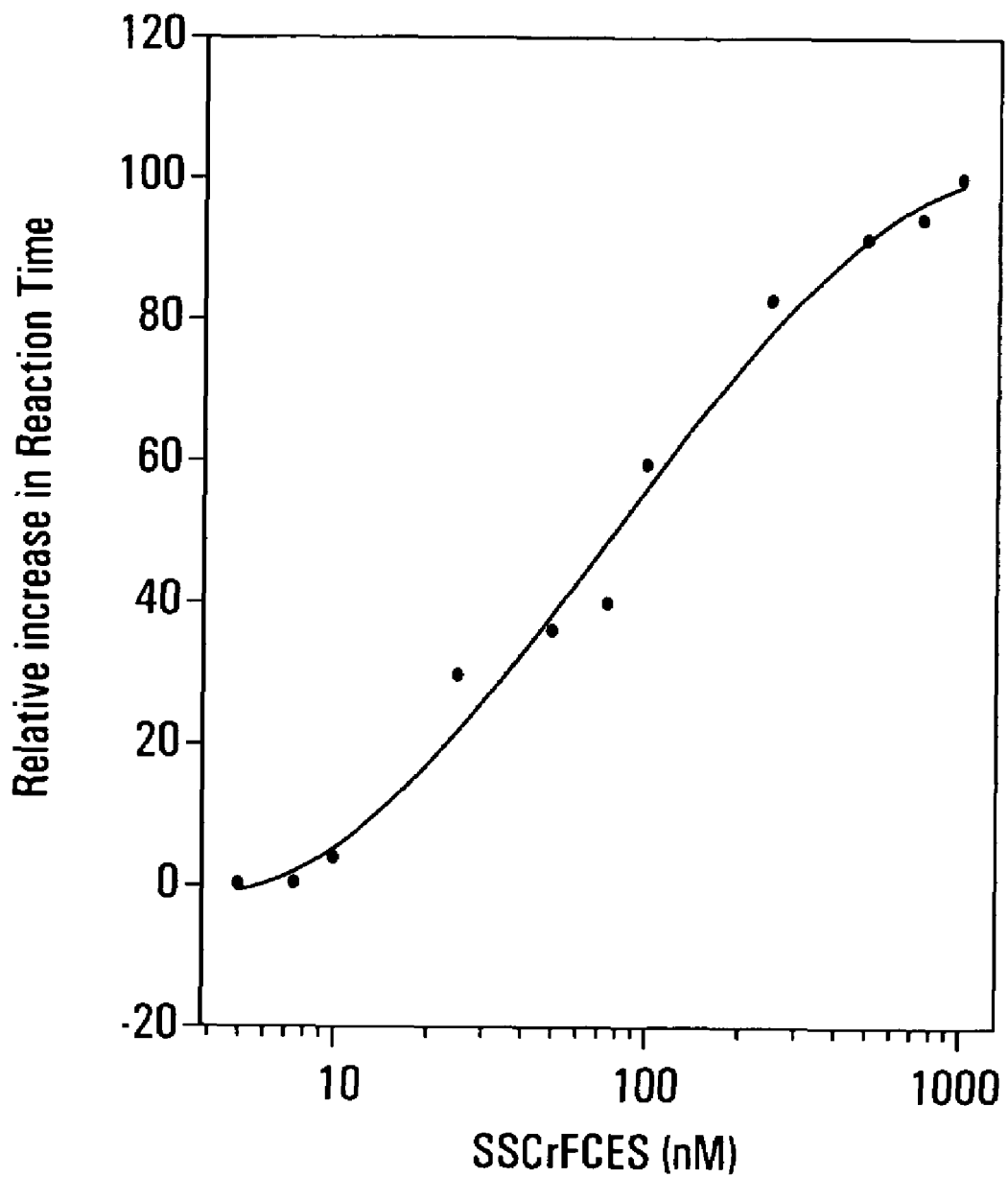

FIG. 4(A). SSCrFCES increases LAL-based Kinetic QCL reaction time. Various concentrations of SSCrFCES were incubated with 200 EU/ml of E. Coli (055:B5) LPS for 1 h at 37° C. Following pre-incubation, the mixture was diluted 1000-fold prior to assay by Limulus Kinetic-QCL. The $O.D._{405nm}$ of each well of the microtitre plate was monitored at time intervals of 5 min over a period of 2 h. The endotoxin-neutralizing concentration ($ENC_{50}$) of SSCrFCES, which is the concentration of SSCrFCES that increase the mean reaction time by 50% was found to be 0.069 μM. Mean reaction time using only LPS is designated as 0%.

Figure 4B:
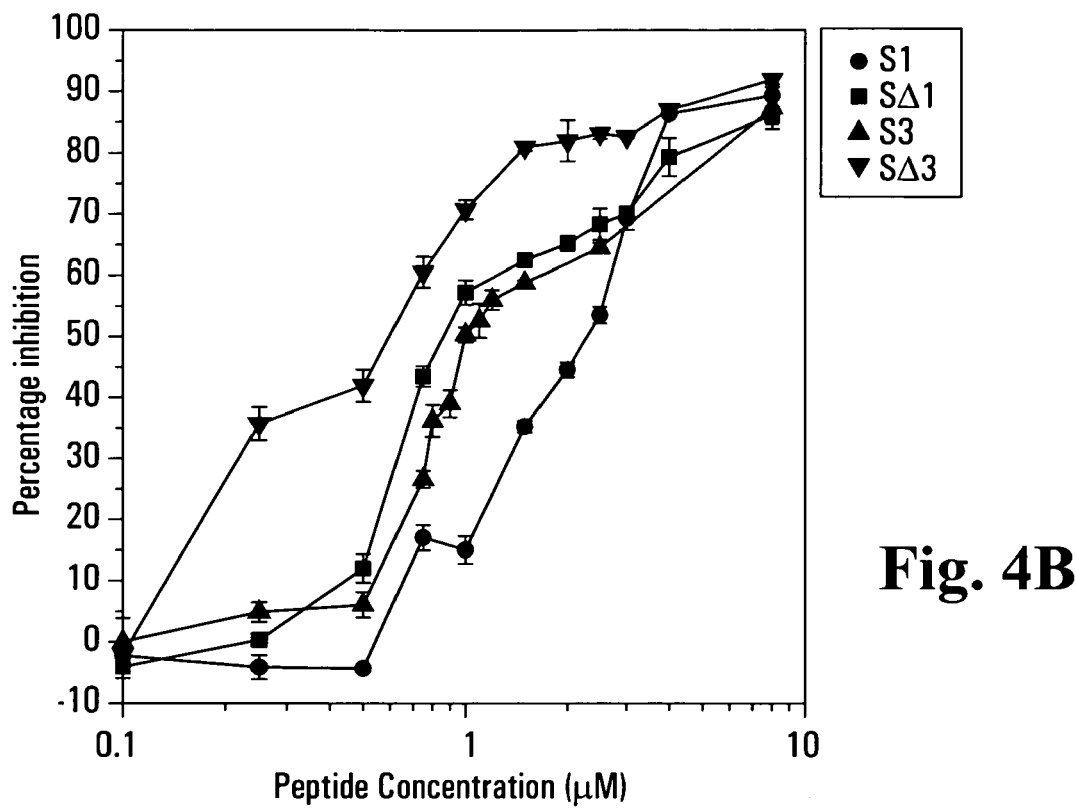

FIG. 4(B). Binding of S1, S1Δ, S3, and S3Δ to LPS. The 50% endotoxin-neutralising concentration ($ENC_{50}$) were determined to be S1=2.25 μM, S1Δ=0.875 μM, S3=1 μM, and S3Δ=0.625 μM.

Figure 4C:
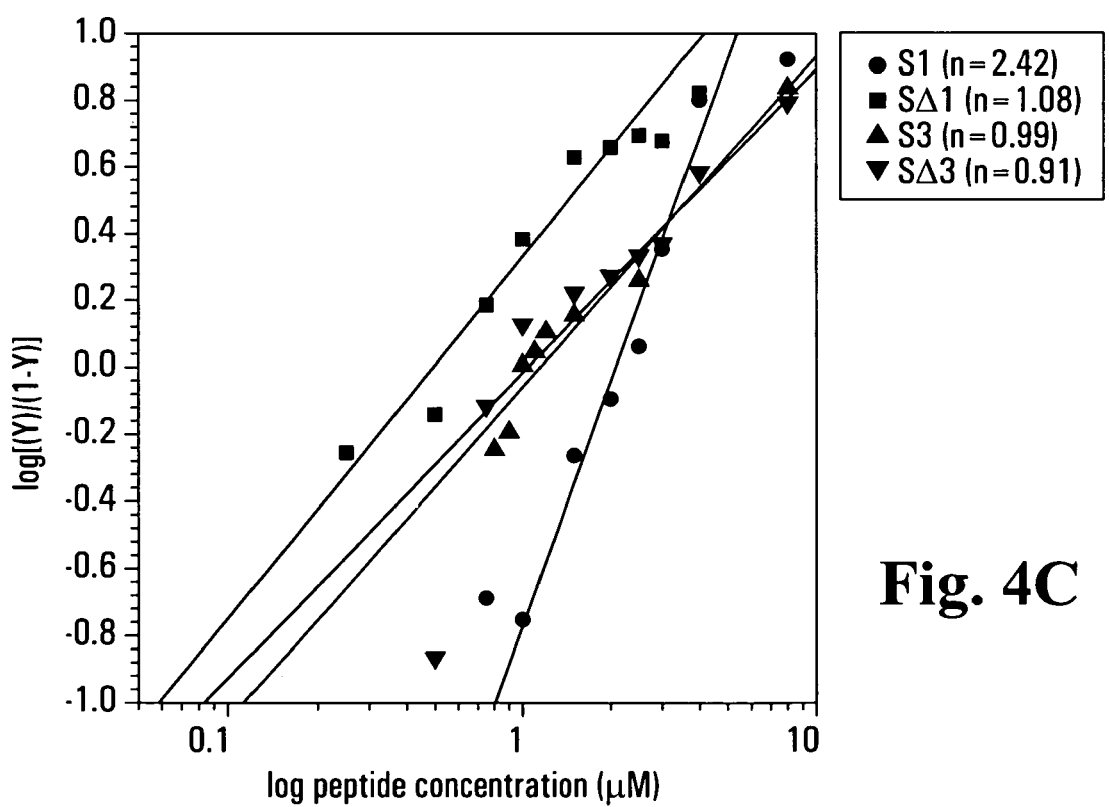

FIG. 4(C). Hill's plot for interaction between synthetic peptides and lipid A shows that S1 exhibits high positive co-operativity of n=2.42, indicating that more than 2 S1 peptides interact with 1 LPS molecule.

Figure 5A:
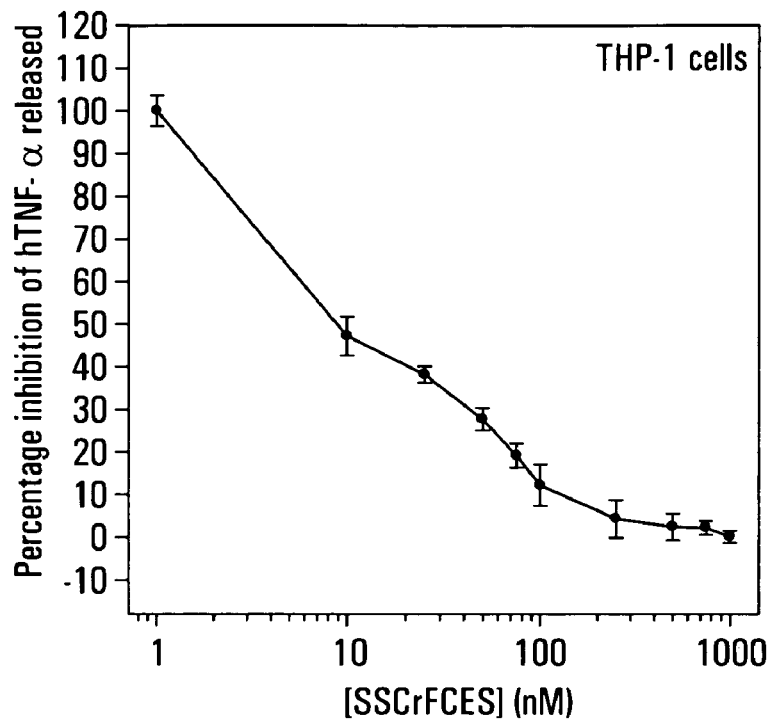

FIG. 5(A). SSCrFCES inhibits LPS-induced hTNF-α secretion from THP-1 in a dose-dependent manner. PMA-treated THP-1 cells were treated with 25 ng/ml of E. coli 055:B5 LPS which were preincubated with varying concentrations of SSCrFCES. After 6 h of stimulation, the culture medium was assayed for TNF-α. The decrease in TNF-α were expressed as percentage of control (LPS only). Complete inhibition of TNF-α was achieved using 1 μM of SSCrFCES.

Figure 5B:
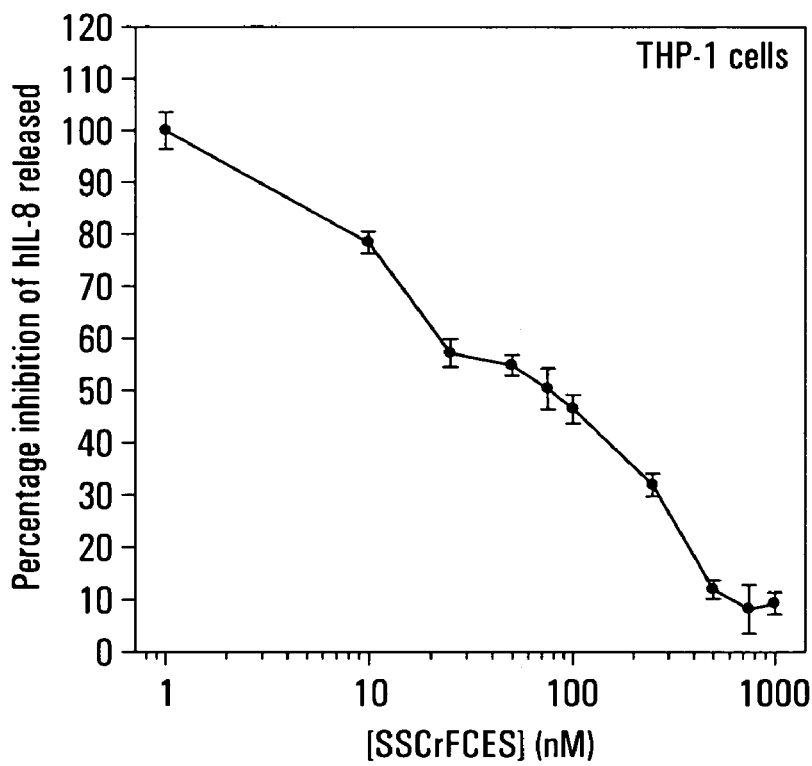

FIG. 5(B). SSCrFCES inhibits LPS-induced hIL-8 secretion from THP-1 in a dose-dependent manner. PMA-treated THP-1 cells were treated with 100 ng/ml of E. coli 055:B5 LPS which was preincubated with varying concentrations of SSCrFCES. After 6 h of stimulation, the culture medium was assayed for IL-8. The decrease in IL-8 secretion was expressed as percentage of control (LPS only). 95% inhibition of IL-8 secretions were achieved using 1 μM of SSCrFCES.

Figure 6A:
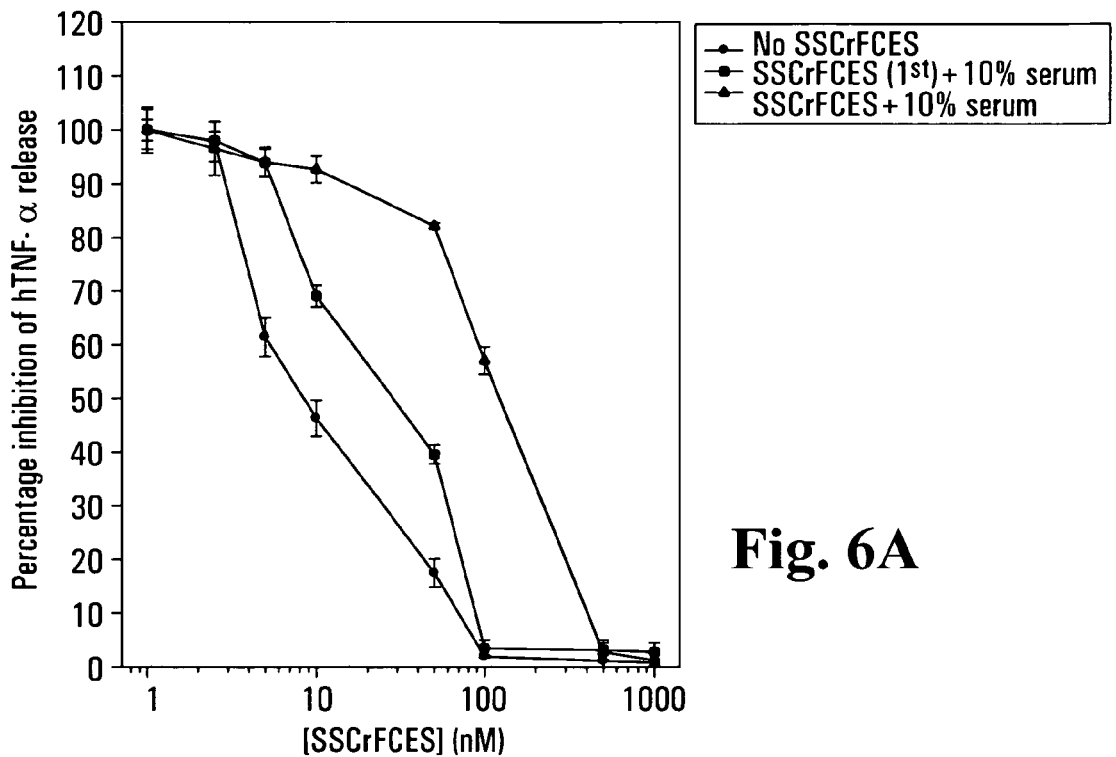

FIG. 6(A). The ability of SSCrFCES to inhibit LPS-stimulated TNF-α secretion from PBMC cells. In the absence of human serum, addition of only 8.5 nM of SSCrFCES caused 50% inhibition of TNF-α response to 10 ng/ml LPS. SSCrFCES pre-incubated with 10% human serum required 17-fold more protein to achieve 50% inhibition. The attenuation can be minimized if the SSCrFCES was mixed with endotoxin 5 min before the addition of serum, thus requiring only 4-fold more SSCrFCES for 50% inhibition of cytokine release.

Figure 6B:
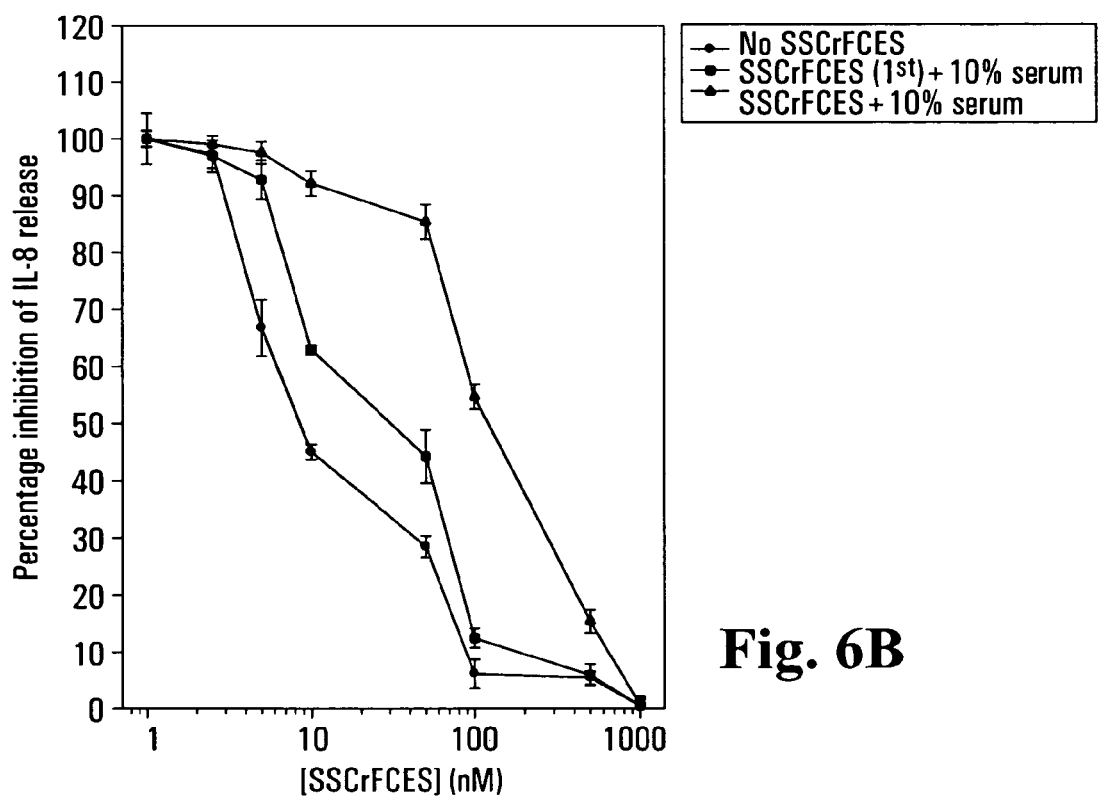

FIG. 6(B). The ability of SSCrFCES to inhibit LPS-stimulated IL-8 secretion from PBMC cells. In the absence of human serum, addition of only 8.5 nM of SSCrFCES caused 50% inhibition of IL-8 response to 10 ng/ml LPS. SSCrFCES pre-incubated with 10% human serum required 17-fold more protein to achieve 50% inhibition. The attenuation can be minimized if the SSCrFCES was mixed with endotoxin 5 min before the addition of serum, thus requiring only 4-fold more SSCrFCES for 50% inhibition of cytoidne release.

Figure 6C:
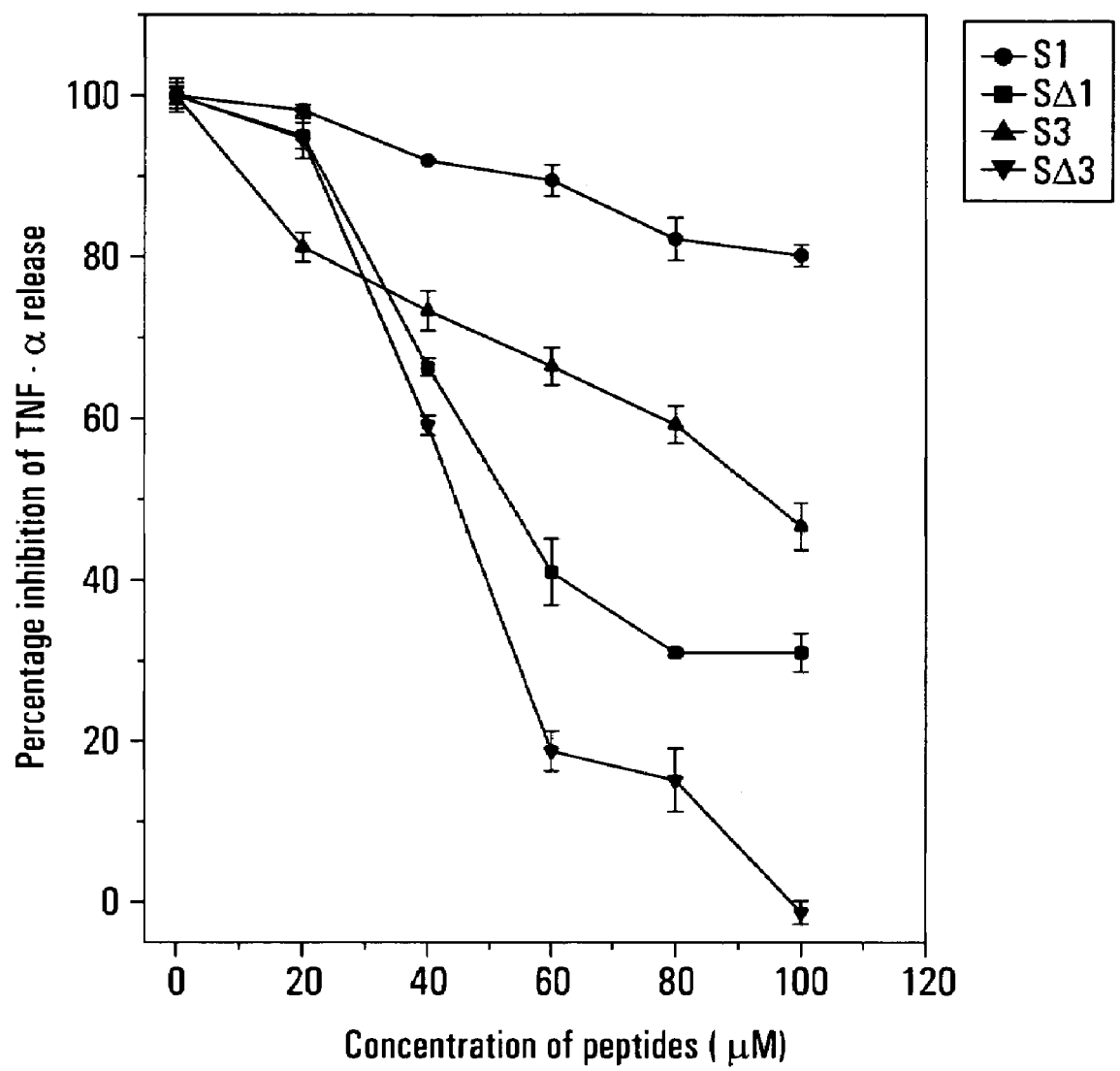

FIG. 6(C). The ability of synthetic peptides to suppress LPS-induced TNF-α.

Figure 7:
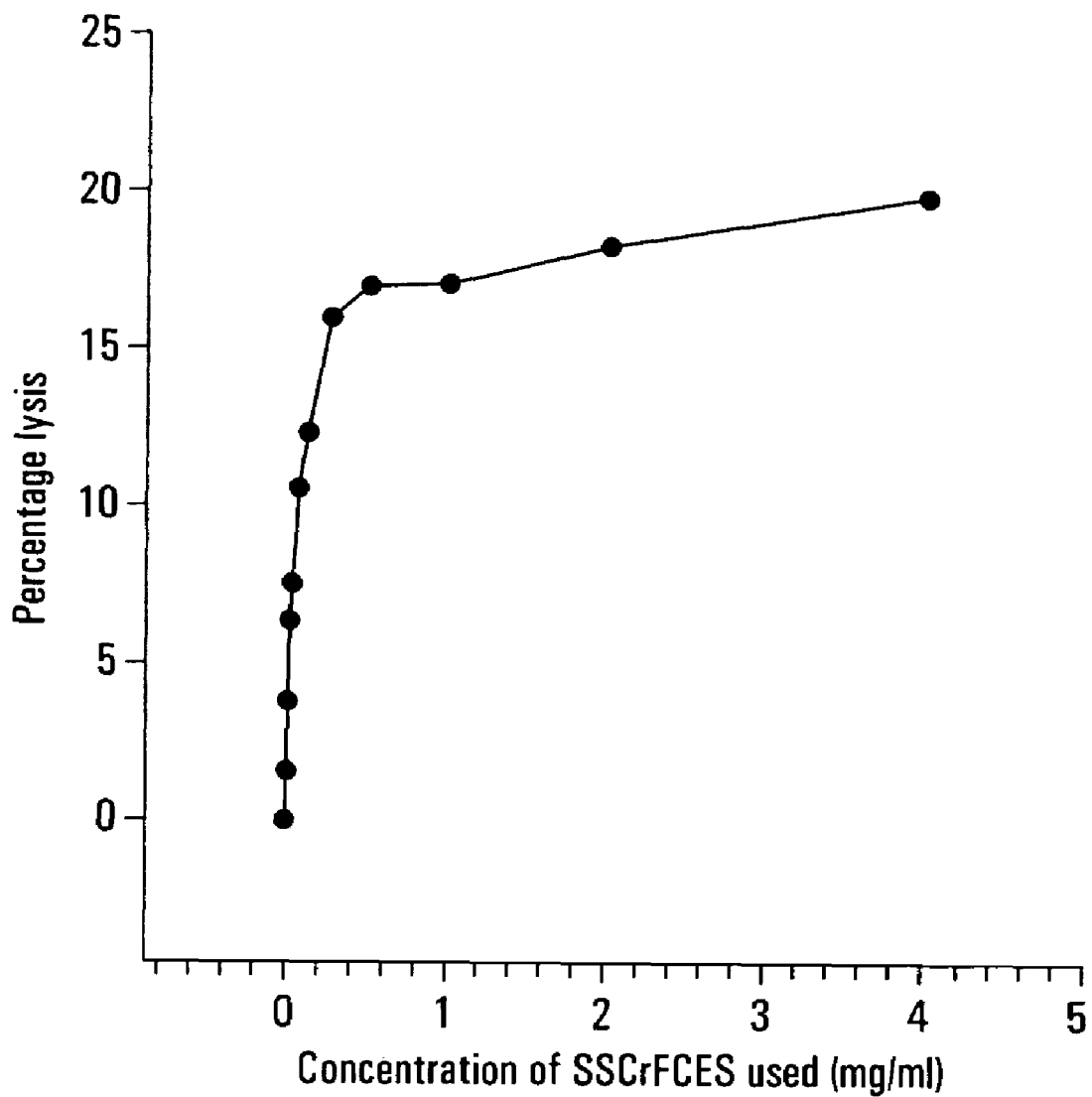

FIG. 7. SSCrFCES is not cytotoxic to mammalian cells. At the highest concentration of 4 mg/ml or 109 μM, only 20% cell lysis was observed.

Figure 8:
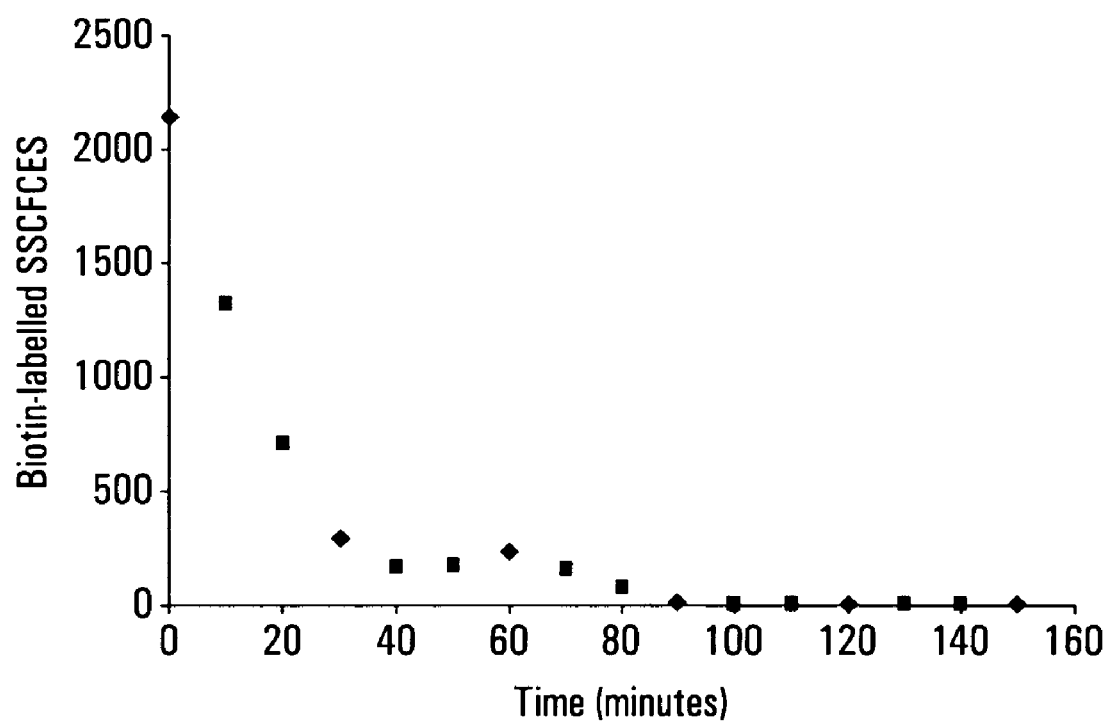

FIG. 8. Pharmacokinetic analysis of SSCrFCES shows that clearance rate of biotin-labeled SSCrFCES in C57BL/6J mice is 4.7 ml/min.

Figure 9A:
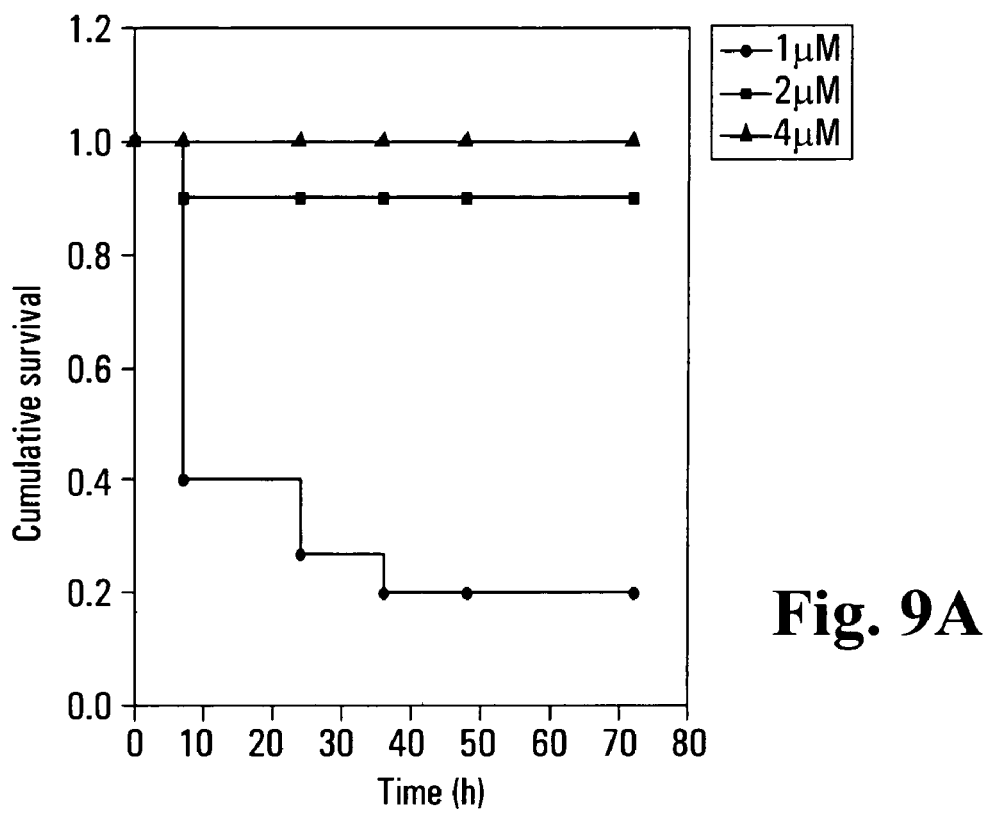

FIG. 9(A). SSCrFCES protects C57BL/6J mice against LPS-induced lethality. 100% LPS-induced lethality was achieved using 2.0 ng of E. coli 055:B5 within 7 h. The percentage of survival was increased to >90% when 2 and 4 μM of SSCrFCES were injected i.v. 10 min after LPS challenge. Kaplan-Meier analysis indicates that there is significant difference between 1 μM and 2 μM of SSCrFCES (P<0.0005). No significant difference was observed between 2 μM and 4 μM of SSCrFCES.

Figure 9B:
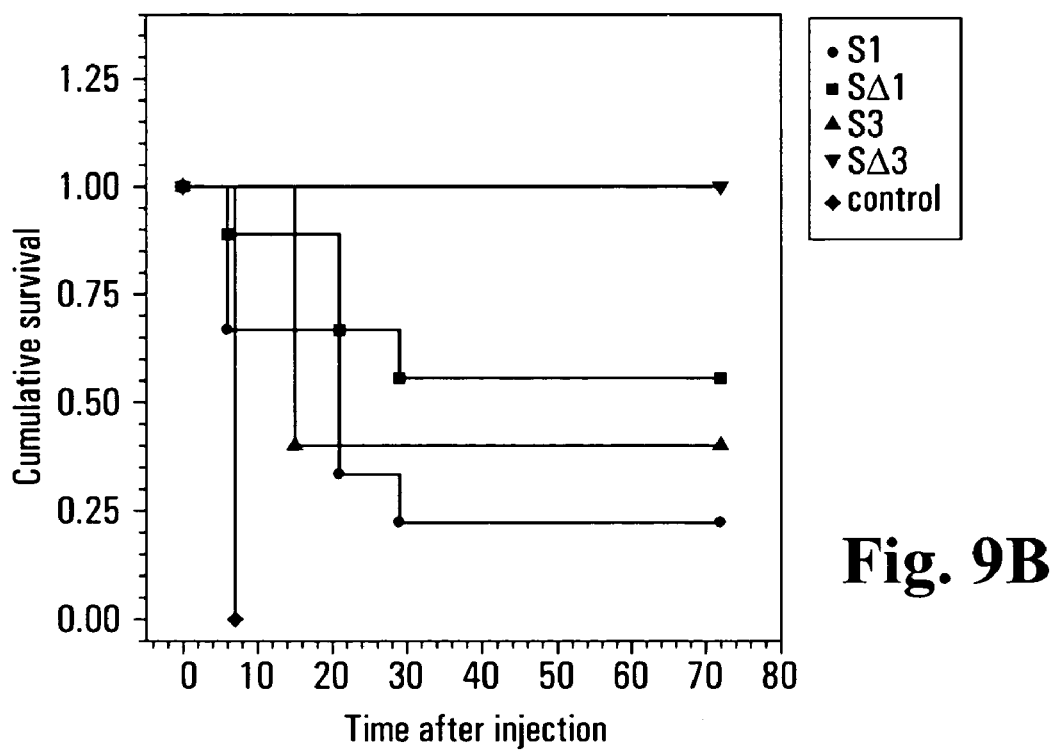

FIG. 9(B). S1, S1Δ, S3, S3Δ, and other designed variant peptides protect C57BL/6J mice against LPS-induced lethality. 100% LPS-induced lethality was achieved using 2.0 ng of E. coli 055:B5 within 7 h. The synthetic peptides (25 or 75 μg) were pre-incubated with LPS for 30 min prior to i.p. injection. S1, S1Δ, and S3 conferred 20-55% decrease in LPS-induced lethality. However, S3Δ is significantly more effective in protection, where 75 ug was sufficient to confer 100% protection.

Figure 10A:
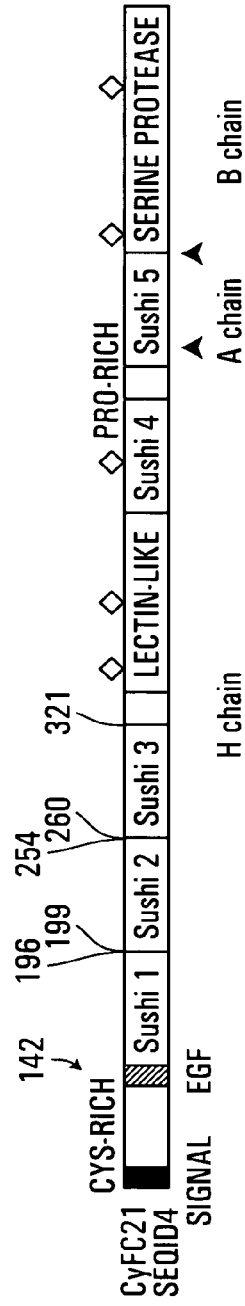

FIG. 10(A). CrFC21 (SEQ ID NO:4) showing functional domains of Factor C.

Figure 10B:
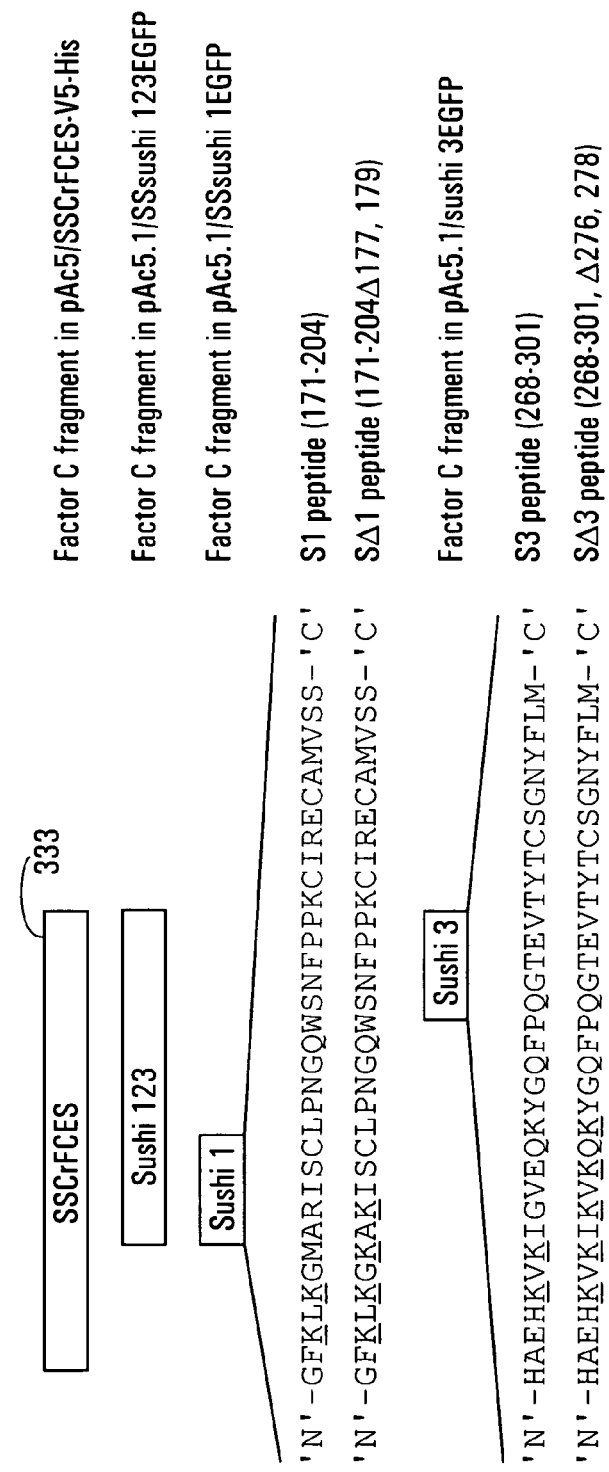

FIG. 10(B). Recombinant fragments: ssCrFCES; sushi-1, 2,3-EGFP; sushi 1-EGFP; and sushi-3-EGFP fusion proteins. Sushi peptides of 34 mer each (S1, S1Δ, S3, & S3Δ).

FIG. 11A. Sequences of V1 and V2 peptides.

FIG. 11B. Sequences of peptides featured in Table 3.

Figure 12:
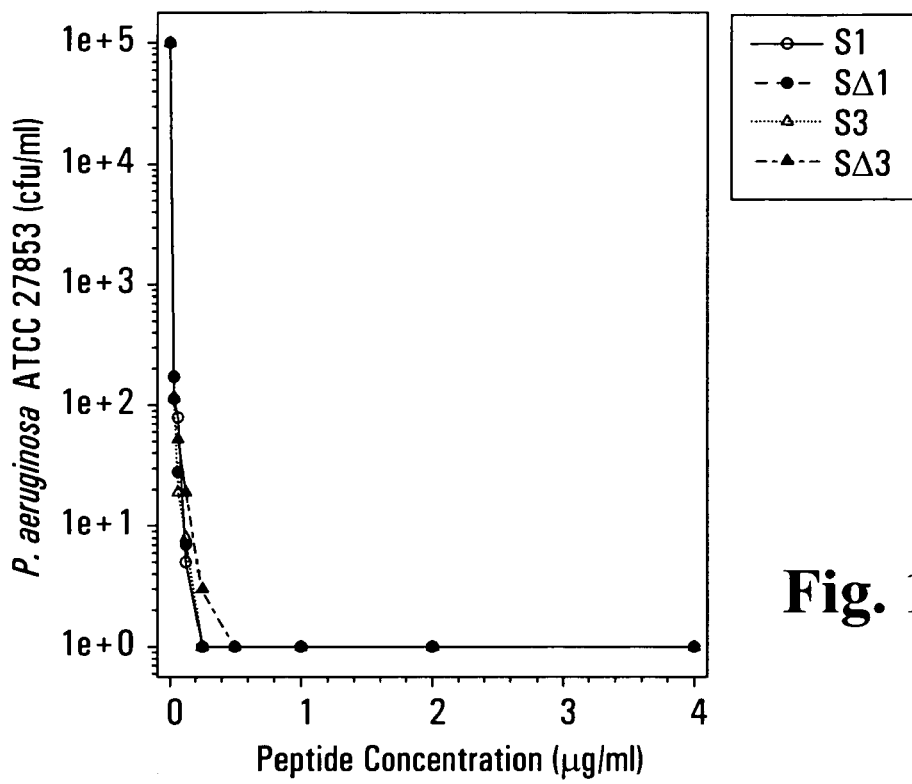

FIG. 12. The microbicidal concentrations (MBC) of sushi peptides against P. aeruginosa (ATCC 27853). An initial density of $10^5$ cfu/ml of P. aeruginosa was used in the assay. Doubling of the peptide concentrations in the region of 0.03-0.5 ug/ml resulted in exponential reduction of bacterial count. S1 and S3 were more effective against P. aeruginosa than S1Δ and S3Δ.

Figure 13:
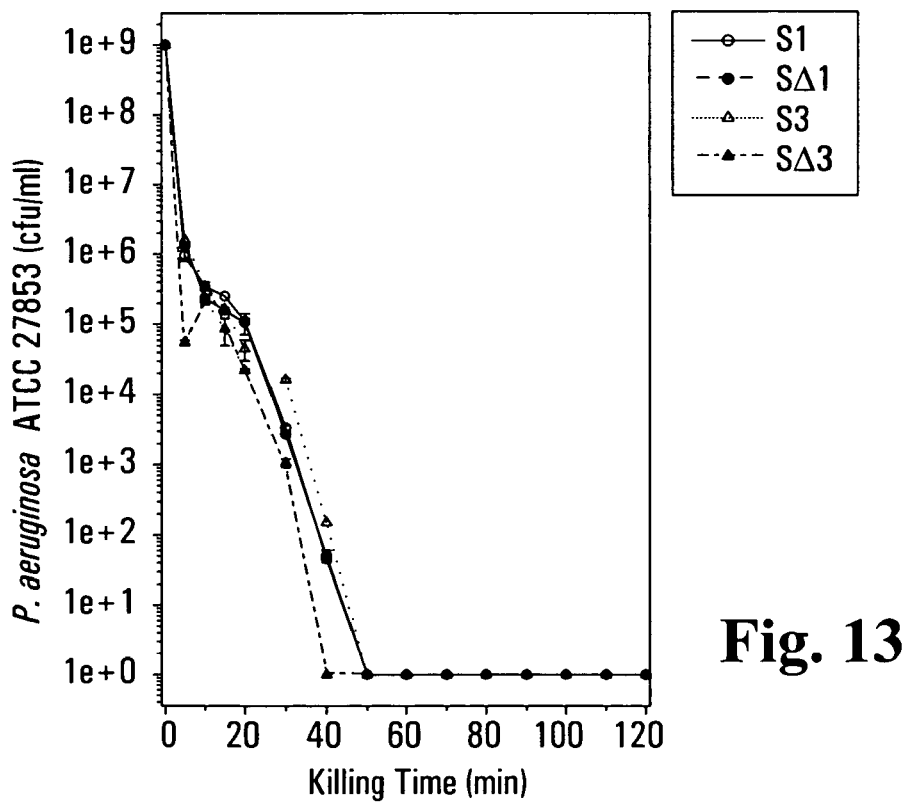

FIG. 13. Time-dependent killing of P. aeruginosa ATCC 27853. An initial density of $10^9$ cfu/ml of P. aeruginosa was used in the assay. The effect of test peptides at 0.06 ug/ml was assessed by enumerating the viable (cfu/ml) at indicated time intervals after overnight incubation. The bacterial count was exponentially reduced to achieve $MBC_{90}$ within 7 min. By 30-40 min, the bacterial was completely eradicated.

Figure 14:
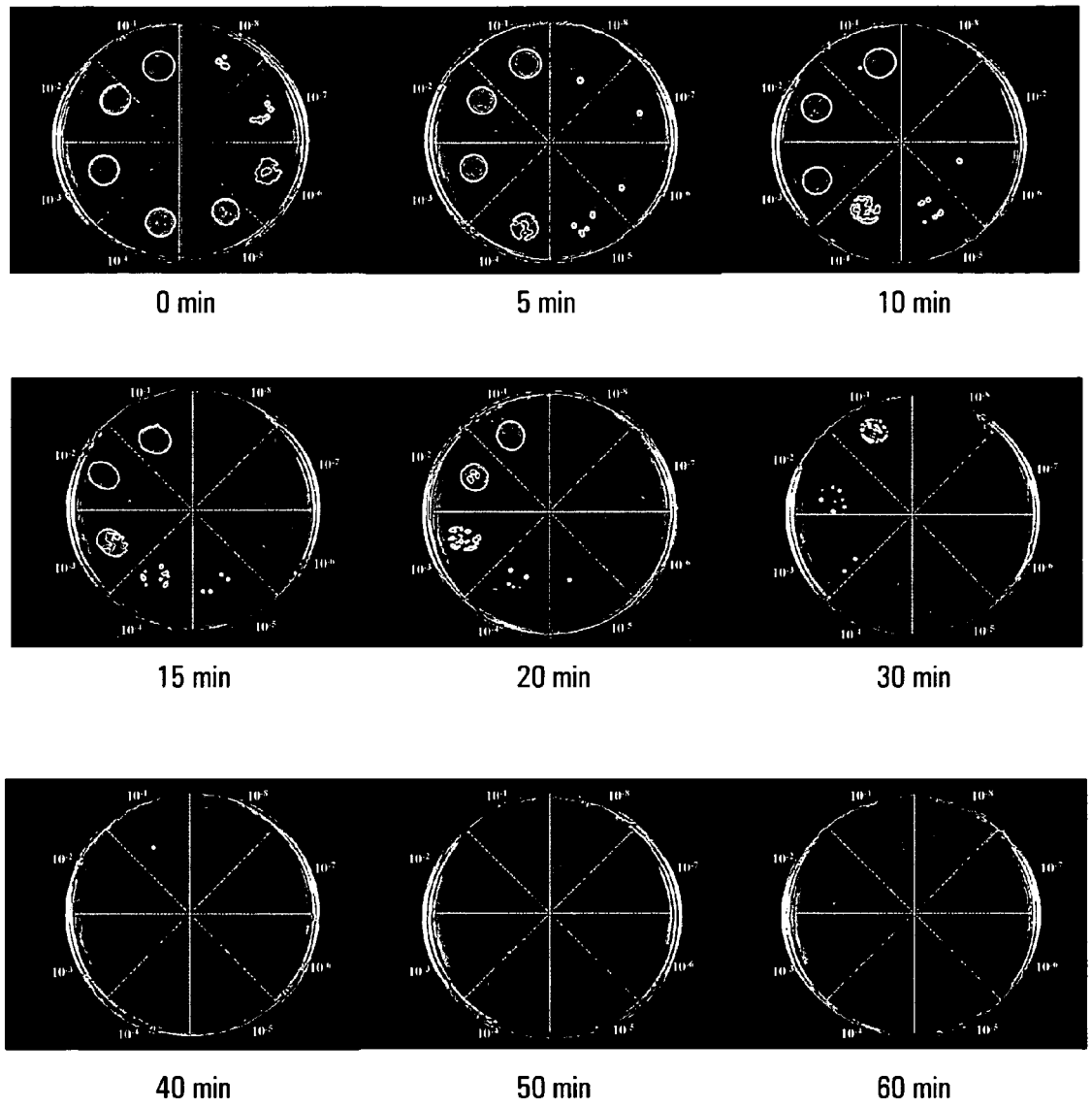

FIG. 14. Drop count plates for the killing rate assay at 0.06 ug/ml of sushi peptides in general, monitored at the indicated time intervals. Segments of the plates contain P. aeruginosa culture at 10-fold dilution starting from $10^{-1}$ to $10^{-8}$ from the upper quadrant in anti-clockwise direction. S3Δ peptide eradicated the bacteria at a log reduction rate.

Figure 15:
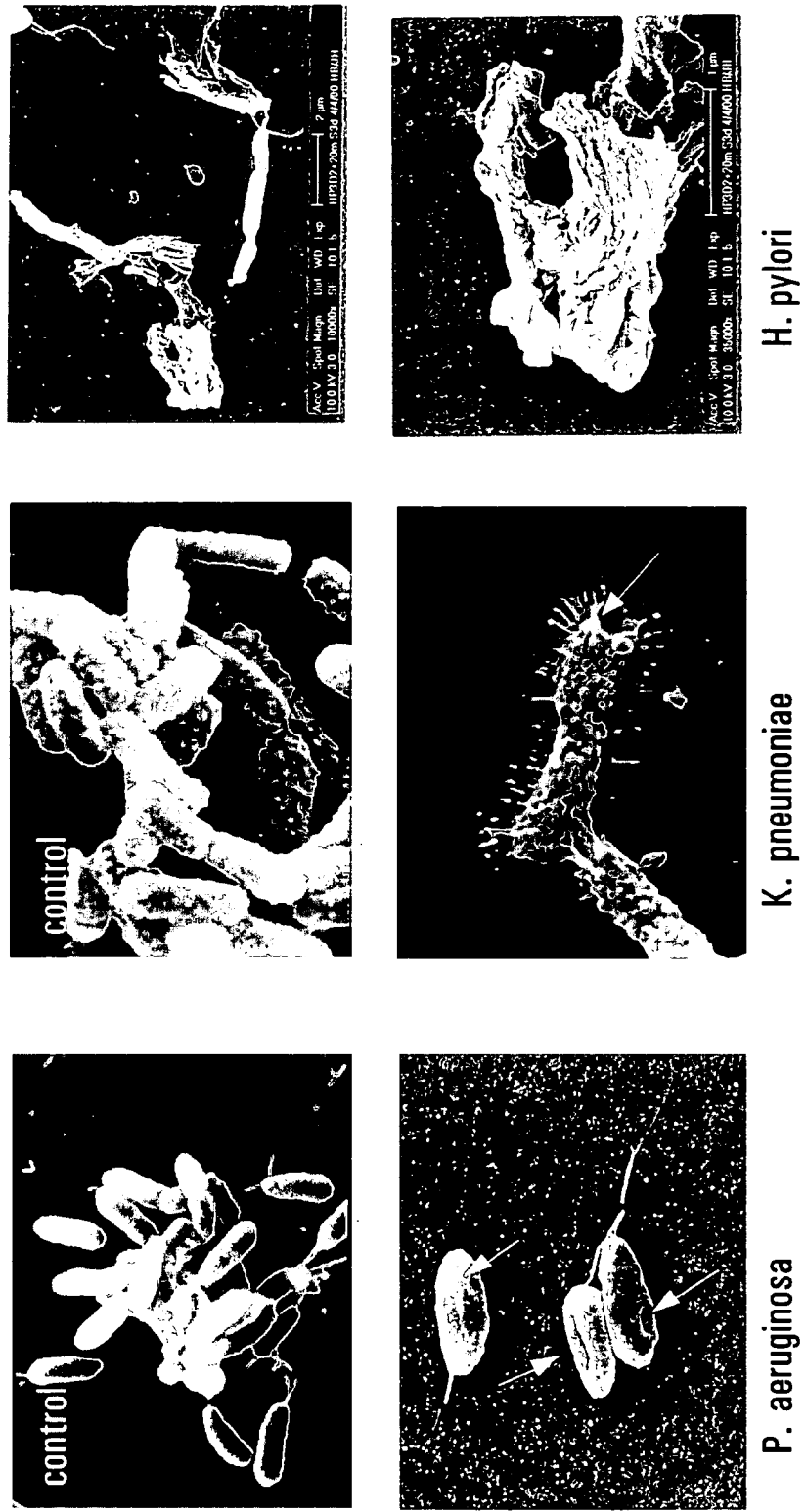

FIG. 15. Electron micrographs showing examples of how the antimicrobial peptides kill the bacteria.

Figure 16:
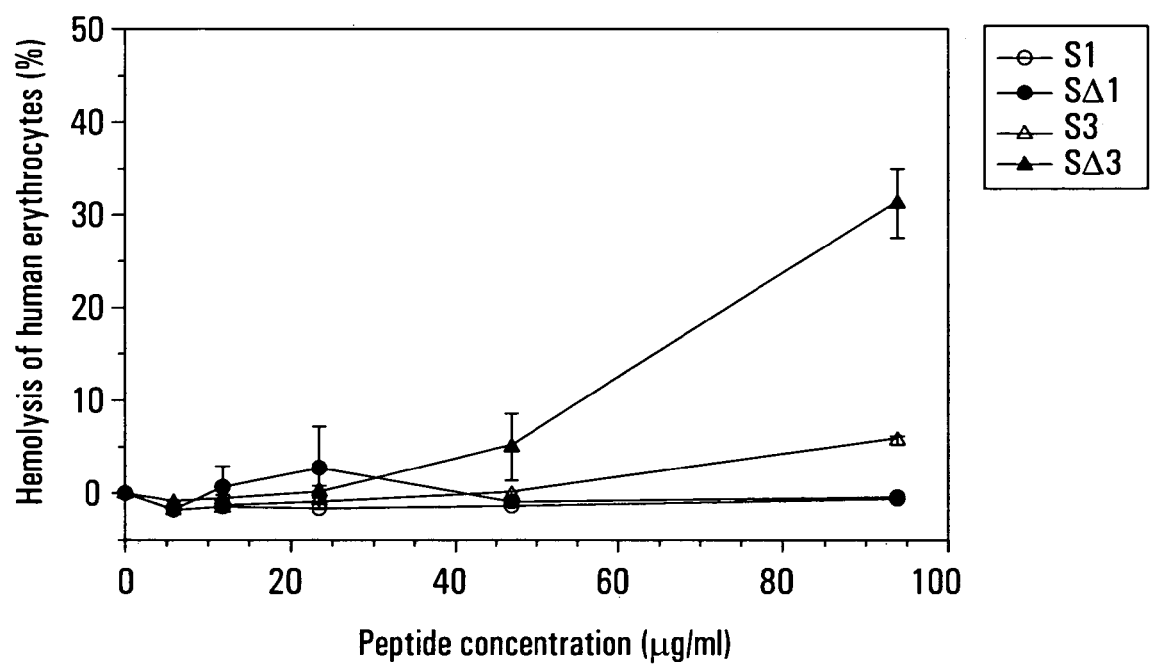

FIG. 16. Sushi peptides display negligible hemolytic activities. Human and rabbit erythrocytes at 0.4% were reacted separately with different doses of peptides (6-100 μg/ml). 0.4% erythrocytes lysed in 1% Triton-X was taken as 100% lysis. The negative control was 0.4% erythrocytes in pyrogen-free saline. Sushi peptides were minimally hemolytic up to concentration of 100 μg/ml. S1, S1Δ, and S3 showed negligible haemolysis and S3Δ caused a 35% haemolysis at 100 µg/ml. Concentration of peptide to induce 50% haemolysis: S1 290 µg/ml; S1Δ 295 µg/ml; S3 160 µg/ml; and S3Δ 120 µg/ml.

Figure 17A:
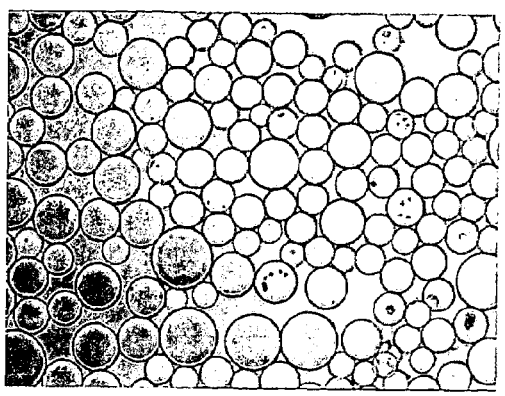
Figure 17B:
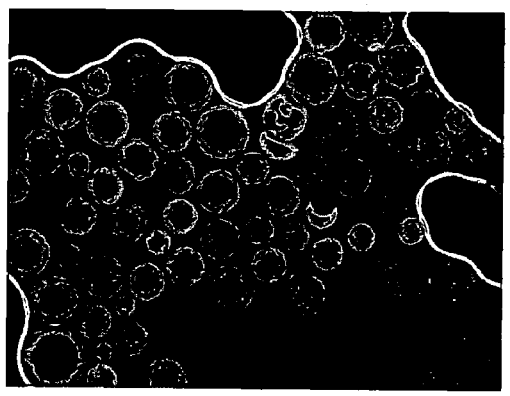
Figure 17C:
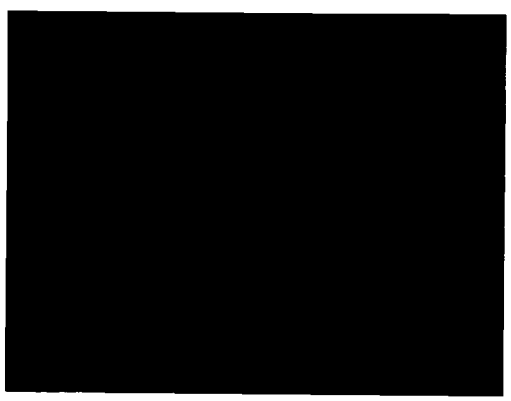

FIG. 17. Example of S3Δ-peptide coupled Agarose CL-6B beads bound with FITC-LPS, seen under microscope. (A) Bright field observation; (B) Beads with FITC-LPS bound, seen under UV light; (C) Bound beads after treatment with 1% DOC—no FITC-LPS left on the beads (observed under UV light).

FIG. 18. A test of binding conditions of LPS to S3Δ peptide affinity beads under increasing pH and ionic strength. (A) pH of 4.0 and 5.0 (in 20 mM sodium acetate), pH 6.8 and 9.1 (20 mM Tris-HCl). All buffers were supplemented with 50 mM NaCl. (B) Different ionic strength: 20 mM Tris-HCl (pH 6.8) were supplemented with different concentrations of NaCl, except of the 0 mM point which contained pyrogen-free water as control.

Figure 19:
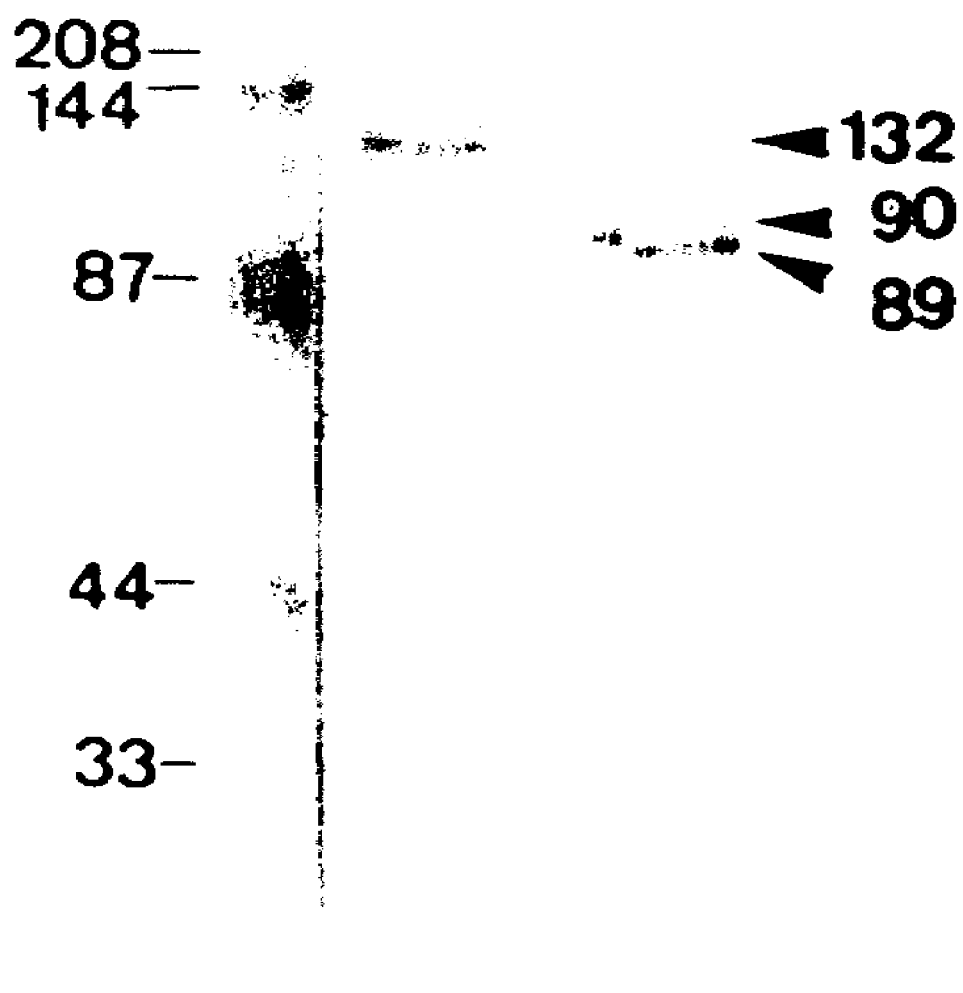

FIG. 19. Immunoblot showing expression of rFC (pHILD2/CrFC21; lane 1), rFCEE (pHILD2/CrFC21EE; lane 2) and rFCSN (pPIC9/CrFC26SN; lane3) in the crude supernatant. Arrows indicate the immunoreactive recombinant Factor C proteins: 132 kDa full-length rFC, 90 kDa truncated rFCEE and 89 kDa truncated rFCSN. The molecular weight markers (MW) are labeled in kDa.

Figure 20:
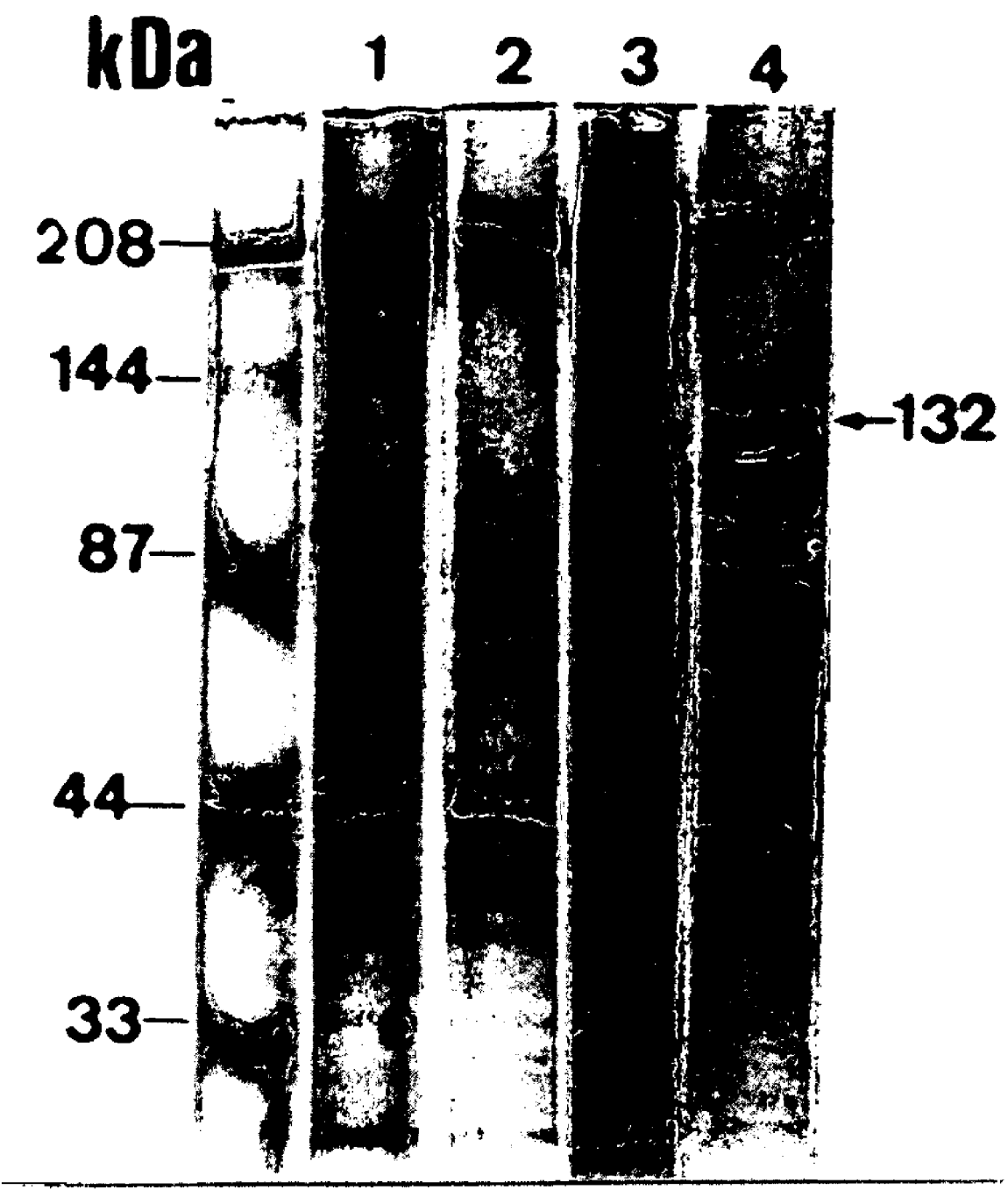

FIG. 20. SDS-PAGE analysis showing the protein profiles of the different preparations of rFC: crude supernatant (lane 1); $(NH_4)_2SO_4$ precipitated sample (lane 2); Biomax™-50 enriched rFC (lane 3); and Sephadex™ G-100 purified sample (lane 4). Ten micrograms of each protein sample were loaded. Arrow indicates the 132 kDa full-length rFC. The molecular weight markers (MW) are labeled in kDa.

Figure 21A:
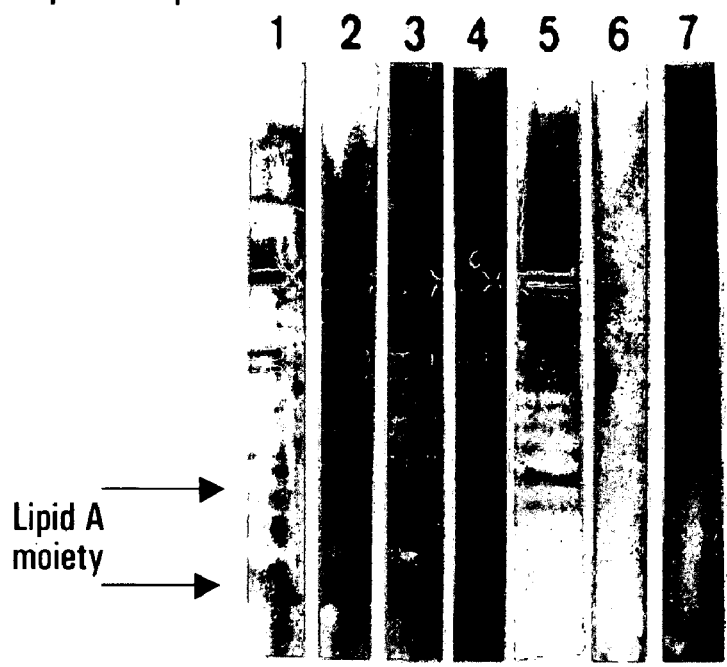
Figure 21B:
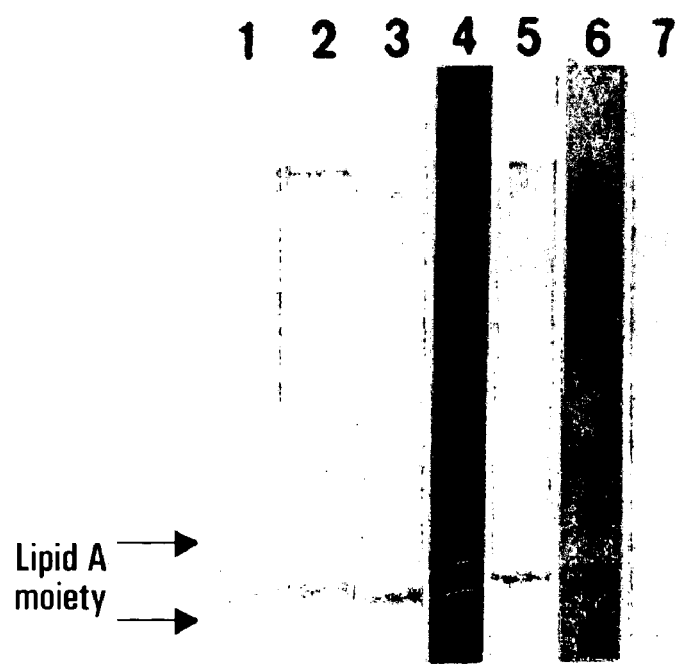

FIGS. 21A and 21B. Modified Western blot to show binding of Factor C to LPS strips (FIG. 21A) and lipid A strips (FIG. 21B). Lanes 1: crude rFC; 2: $(NH_4)_2SO_4$ precipitated rFC; 3: Biomax™-50 purified rFC; 4: Sephadex™ G-100 purified rFC; 5: Biomax™-50 purified rFCEE; 6: Biomax™-50 purified rFCSN; 7: pHILD2/151 supernatant. The 7-20 kDa lipid A bands are indicated between the 2 arrows.

Figure 22A:
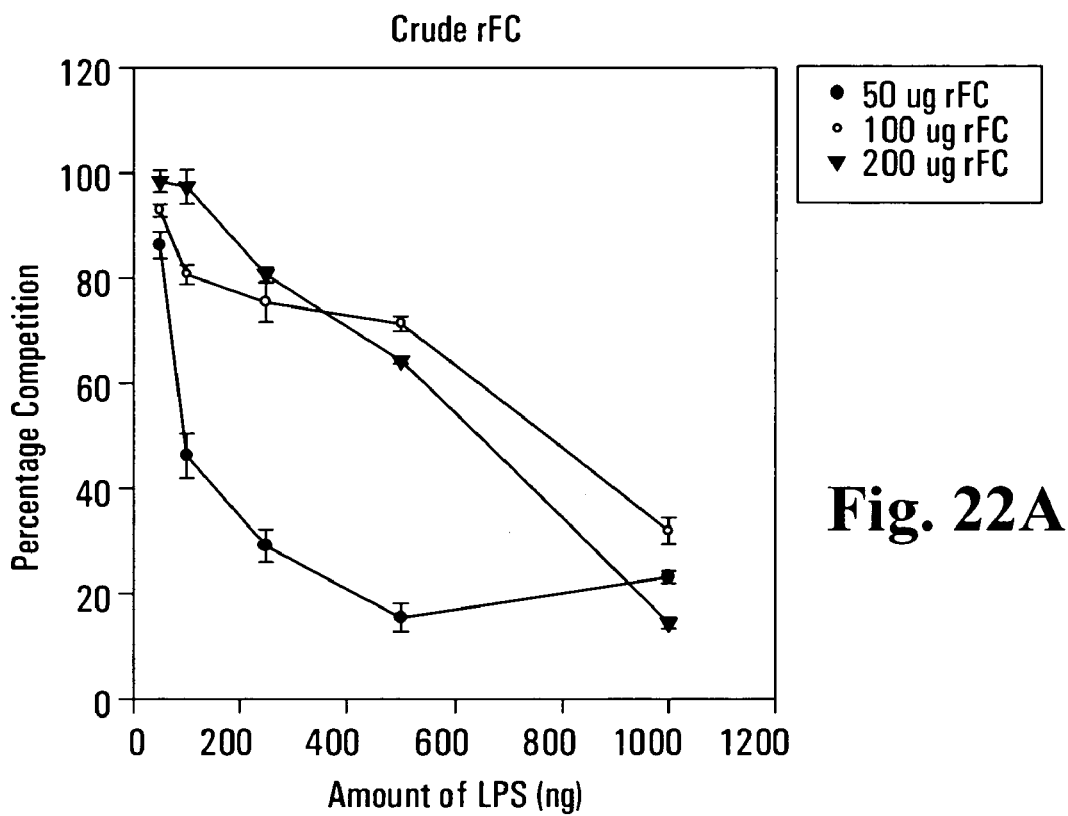

FIG. 22A. Competitive effects of 50, 100 and 200 µg total protein of crude rFC on LPS-mediated activity of CAL Factor C enzyme activity. Dashed line illustrates the ratio of crude rFC to LPS (1000:1) for a percentage competition of >80%. Results are the means±S.D. of three independent experiments.

Figure 22B:
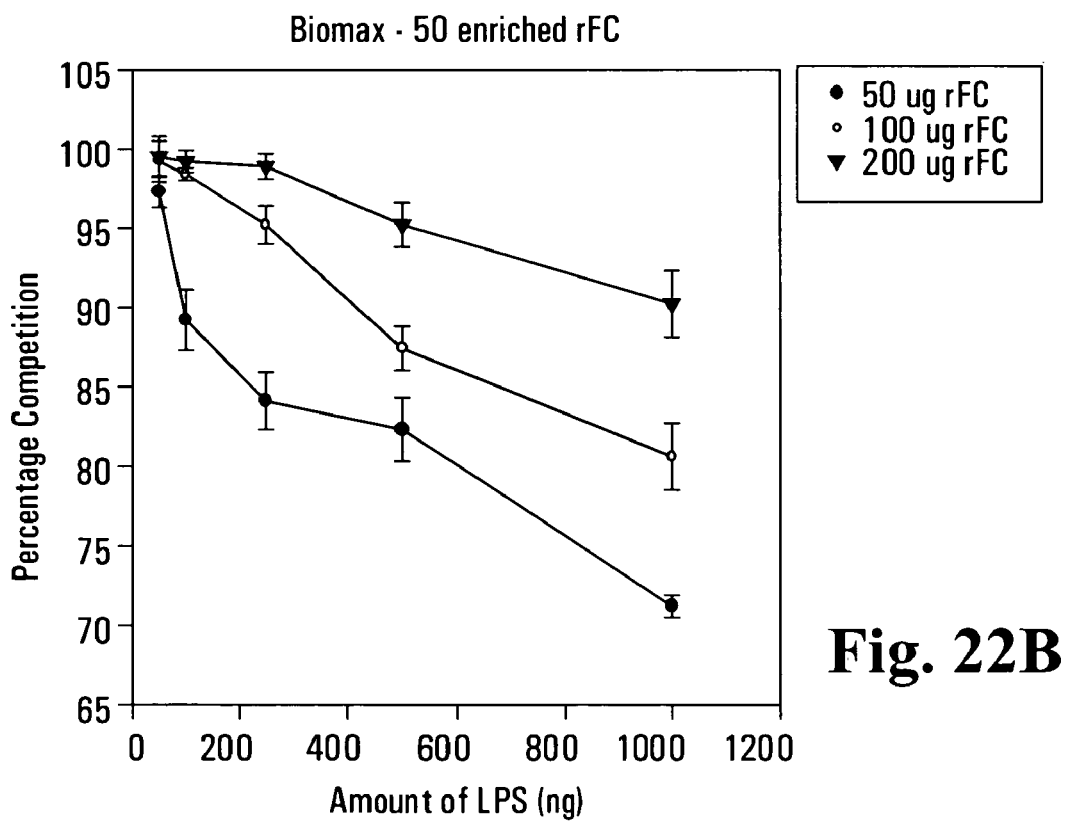

FIG. 22B. Competitive effects of 50, 100 and 200 µg Biomax™-50 enriched rFC on LPS-mediated activity of CAL Factor C enzyme activity. Dashed line illustrates the ratio of rFC to LPS (100:1) for a percentage competition of >80%. Results are the means±S.D. of three independent experiments.

Figure 23:
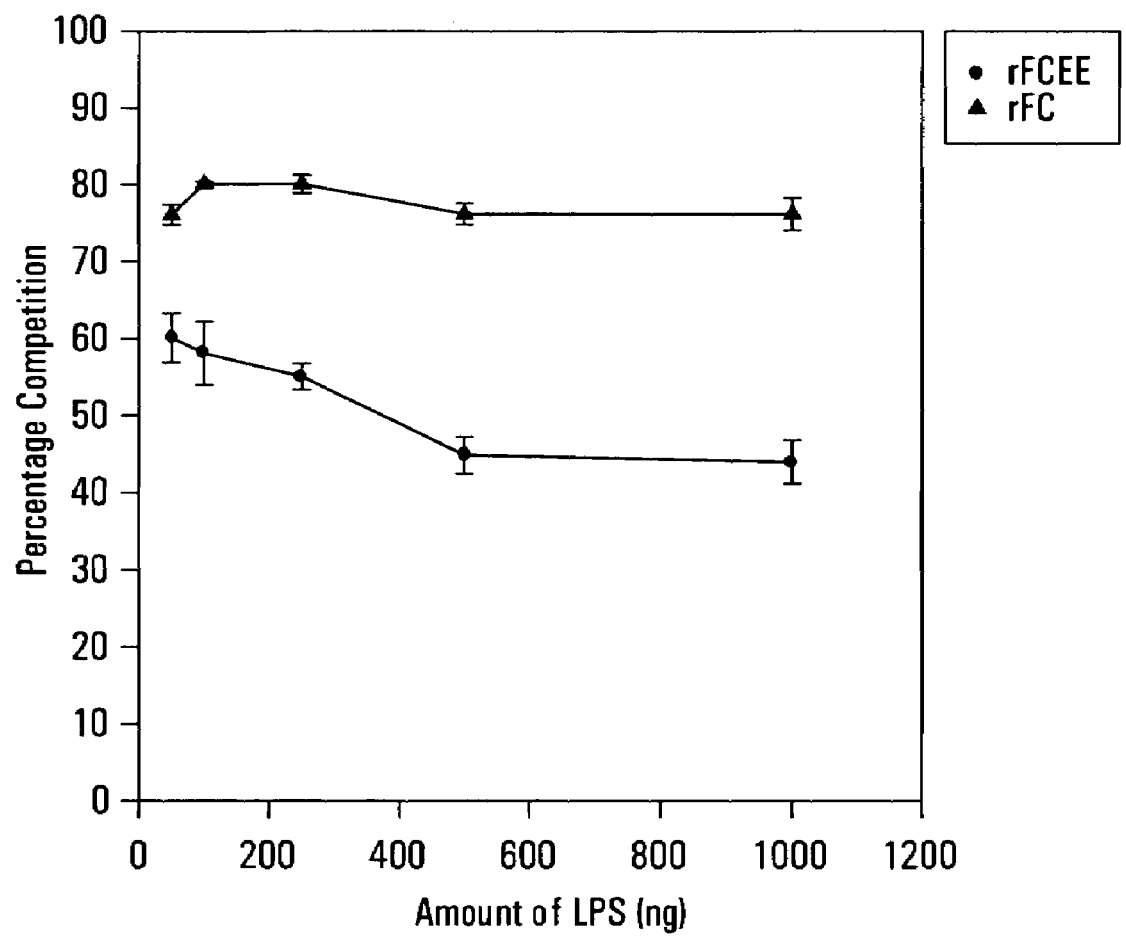

FIG. 23. Comparison of the competitive efficiencies of full-length rFC and truncated rFCEE on LPS-mediated enzymatic activity of CAL Factor C. Each protein sample (rFC or rFCEE) was enriched by Biomax™-50 ultrafiltration, and 100 µg was used in the competition assay. The percentage competition was obtained after normalization with the background competition by rFCSN. Results are the means±S.D. of three independent experiments.

Figure 24:
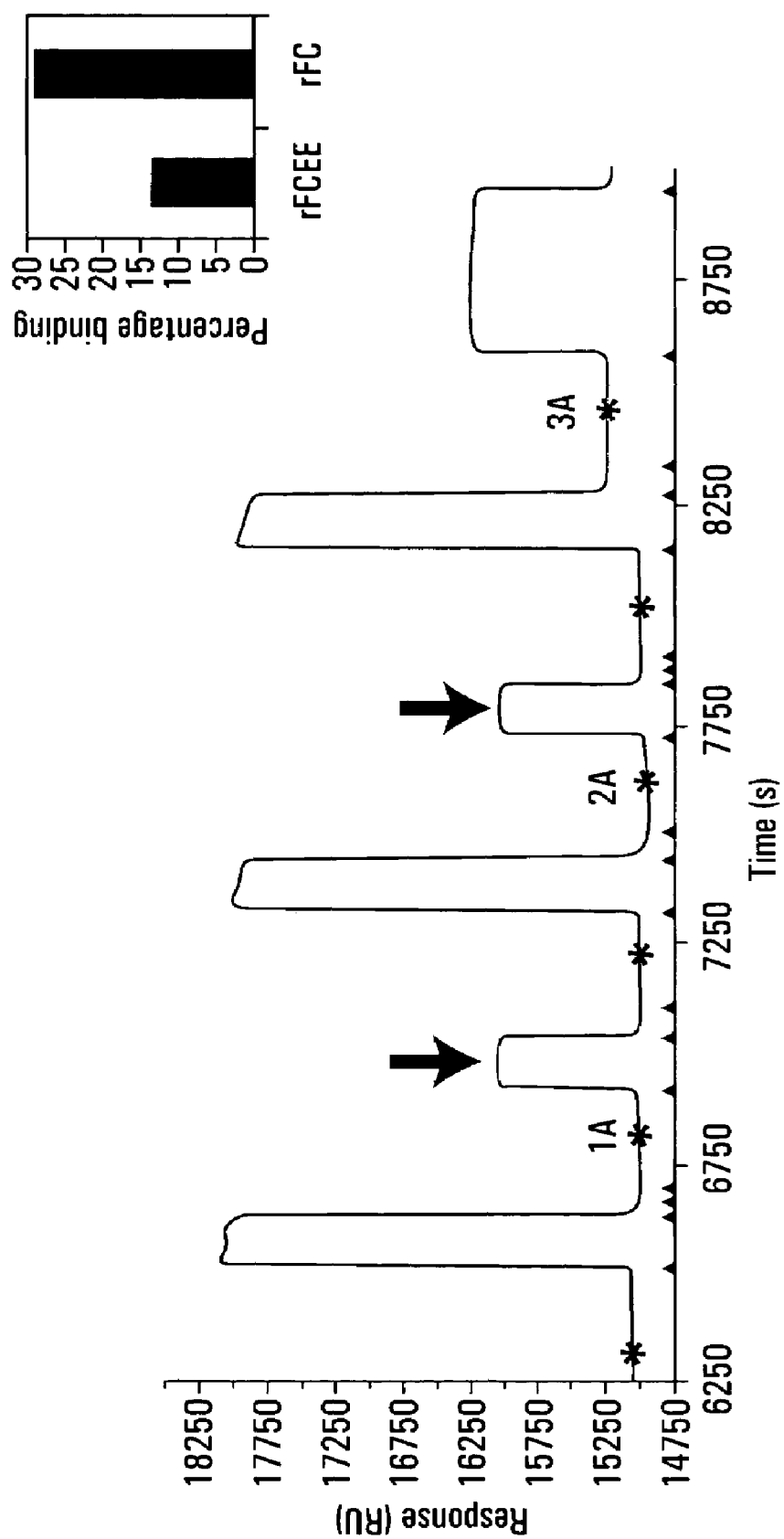

FIG. 24. Interactive binding of rFC to immobilized lipid A in a BIACORE X™ sensor. Lipid A (100 µg/ml) was immobilized on the sensor chip. The respective protein samples were flowed through and relative responses recorded in response units (RU) by the BIACORE X™ instrument. Plateaus 1A, 2A and 3A on the sensorgram represent the relative responses of Biomax™-50 enriched rFCSN, rFCEE and rFC, respectively, to immobilized lipid A. Arrows show the RU due to regeneration with 0.1M NaOH. Inset shows the net percentage RU of rFC and rFCEE to immobilized lipid A. The percentage RU of each protein sample was calculated based on the relative RU of the protein sample and that of immobilized lipid A. The net RUs of rFC and rFCEE were obtained after normalizing their relative RUs with that of rFCSN.

Figure 25:
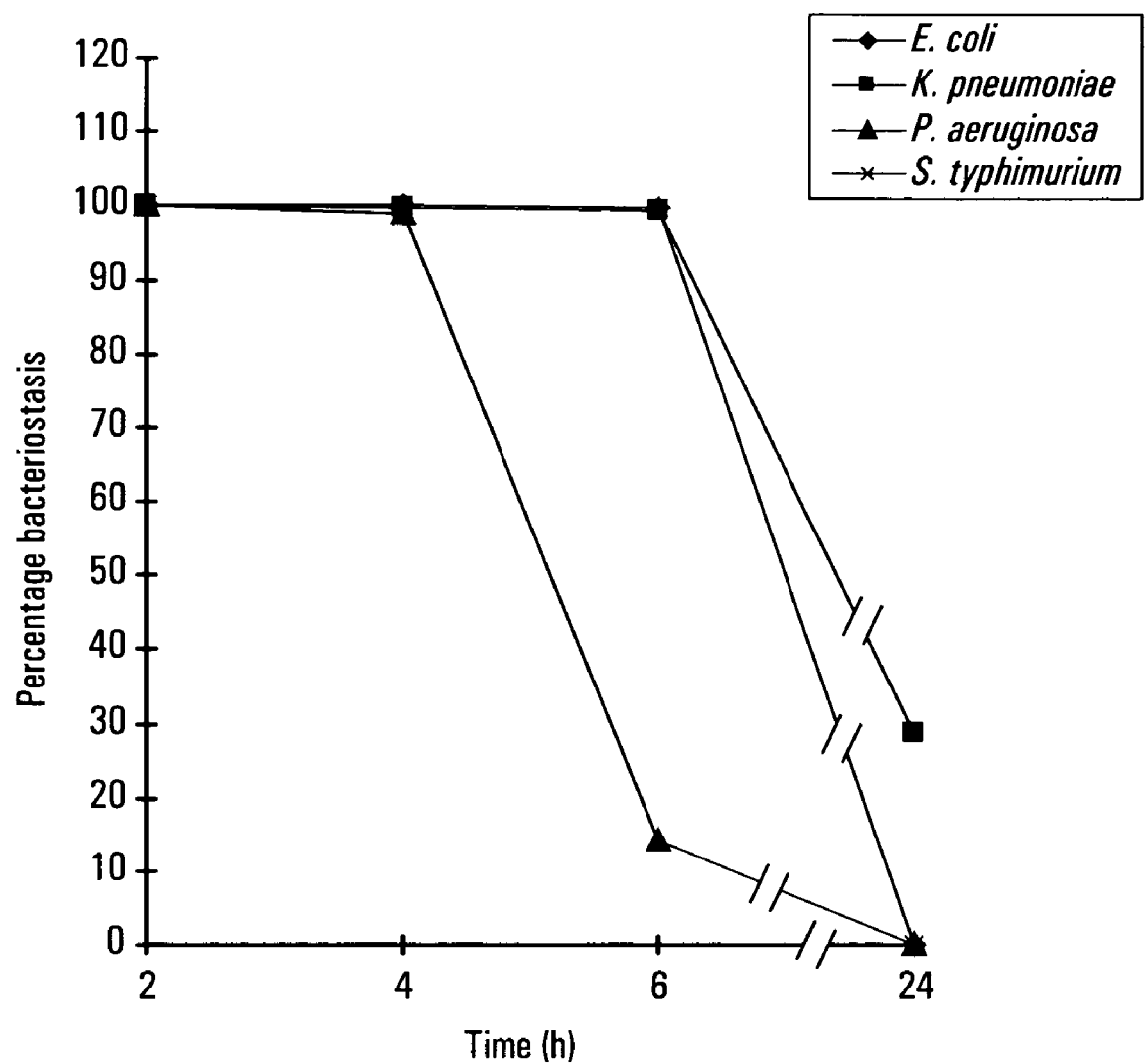

FIG. 25. The bacteriostatic effects of Sephadex™ G-100 purified rFC on the growth of the Gram-negative bacteria: *E. coli*, *K. pneumoniae*, *P. aeruginosa*, and *S. typhimurium*. rFC was most efficacious against *K. pneumoniae* whereas the bacteriostatic activity against *P. aeruginosa* declined rapidly after 4 h.

Figure 26A:
Figure 26B:
Figure 26C:
Figure 26D:
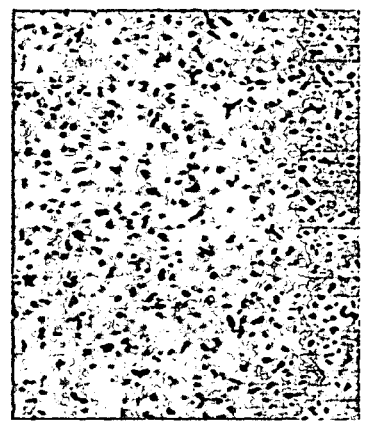
Figure 26E:
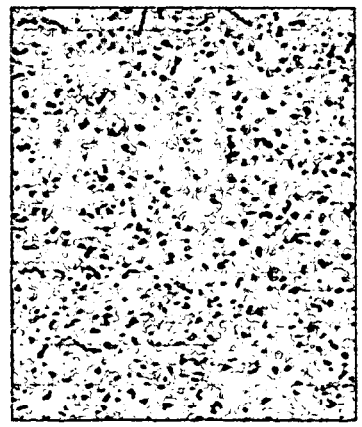

FIGS. 26A-26E. Agglutination of *E. coli* by rFC (FIG. 26A) and rFCEE (FIG. 26B). Observations were made with a Nikon MICROPHOT™-FXA microscope (400× magnification). No agglutination was seen with rFCSN (FIG. 26C), pHILD2/151 (FIG. 26D) and 0.85% saline (FIG. 26E).

Figure 27:
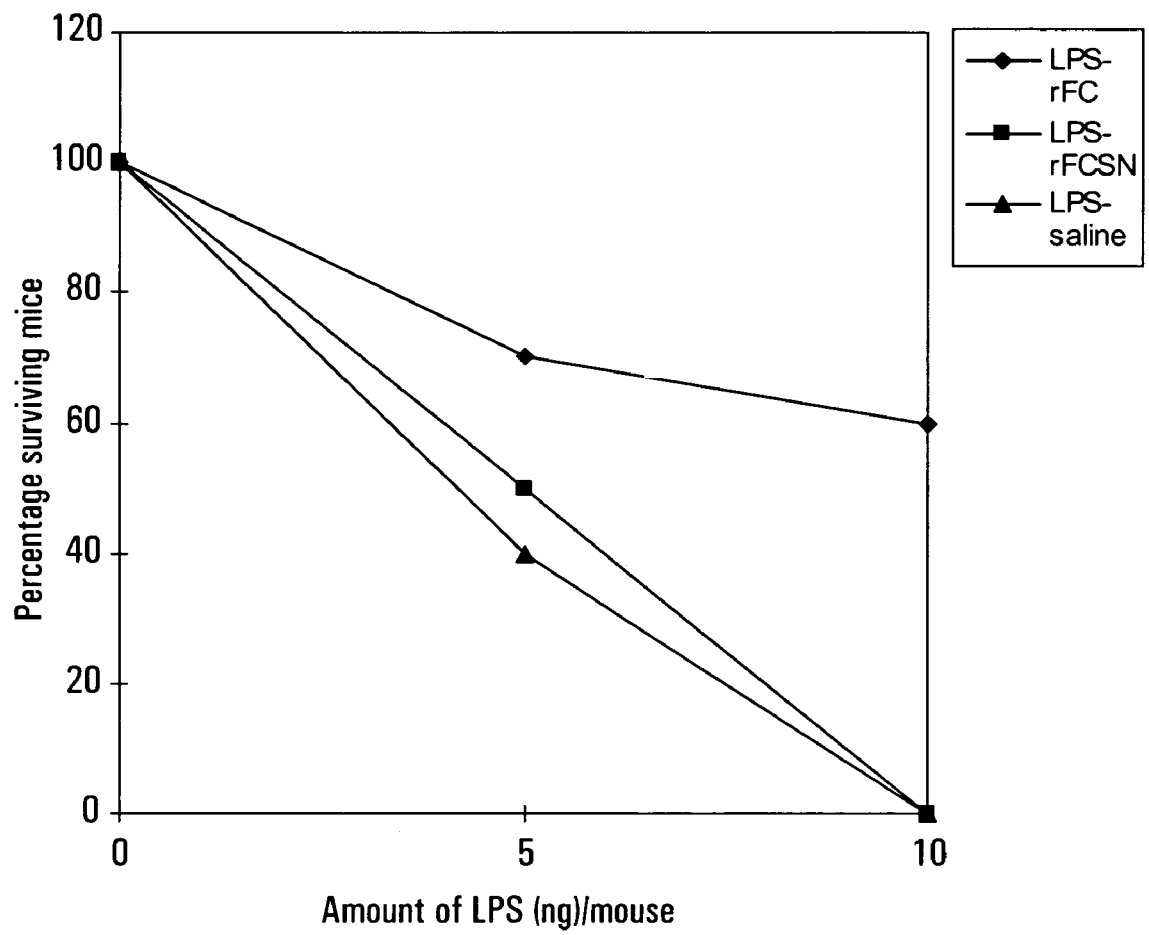

FIG. 27. The protective effect of 10 µg rFC purified through Sephadex™ G-100 on actinomycin D sensitized/ LPS-challenged mice. Pre-incubation of LPS with rFCSN did not confer protection of mice against the endotoxic effects of LPS. For comparison, rFC conferred 60-70% protection.

Figure 28:
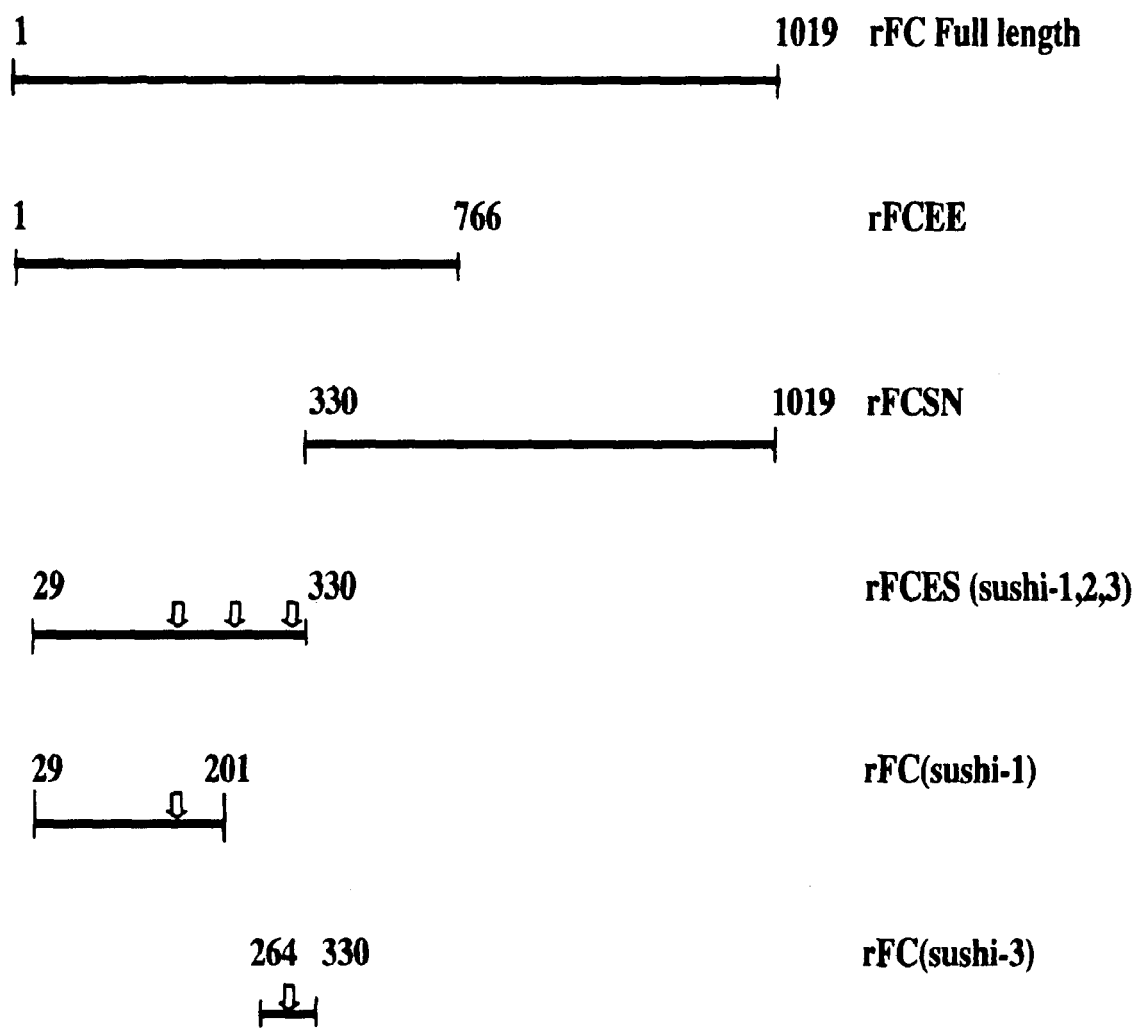

FIG. 28. Line drawings of rFC (full length) and its deletion homologues, given with their corresponding start and end amino acid positions based on the CrFC21 clone (SEQ. ID. NOs. 3 and 4, U.S. Pat. No. 5,716,834). Amino acid residues are numbered as in SEQ. ID. NO. 4. rFC, rFCEE, rFCES(sushi-1,2,3), rFC(sushi-1) and rFC(sushi-3) have endotoxin-binding site(s). Sushi (⇩) domains 1, 2, and 3 denote secondary structures in Factor C, with 'sushi-like' folding patterns. rFCSN does not contain any endotoxin-binding site. The lines are not drawn to scale.

Figure 29:
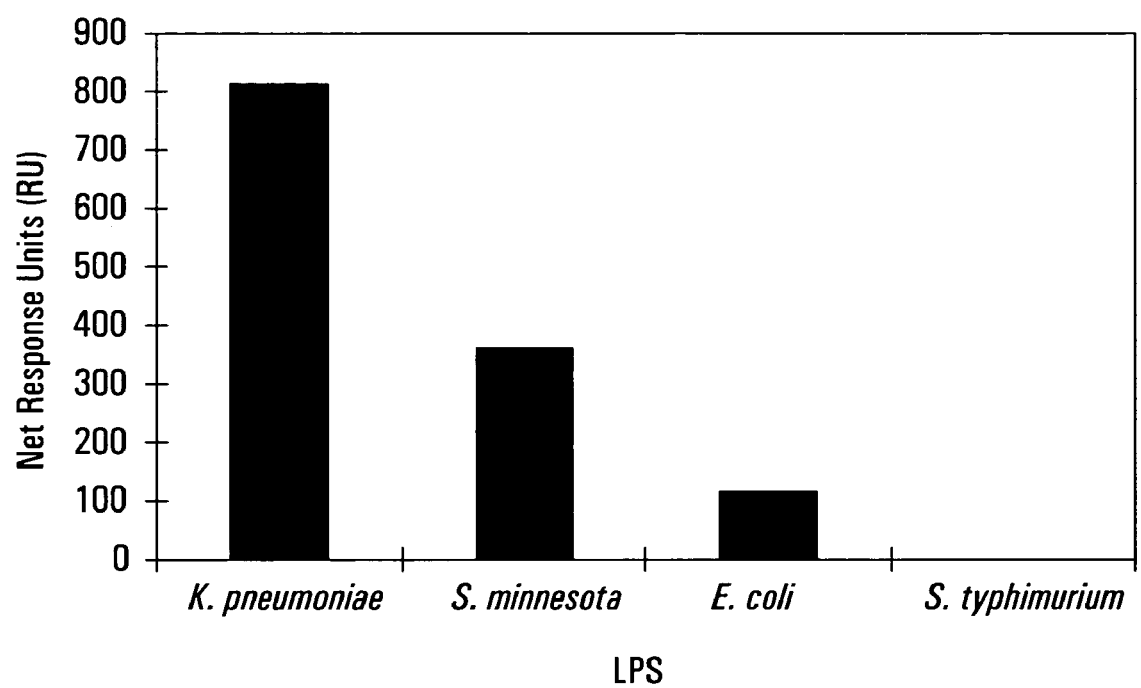

FIG. 29. Binding of rFC produced in baculovirus-infected Sf9 cells to LPS from various bacteria.

Figure 30:
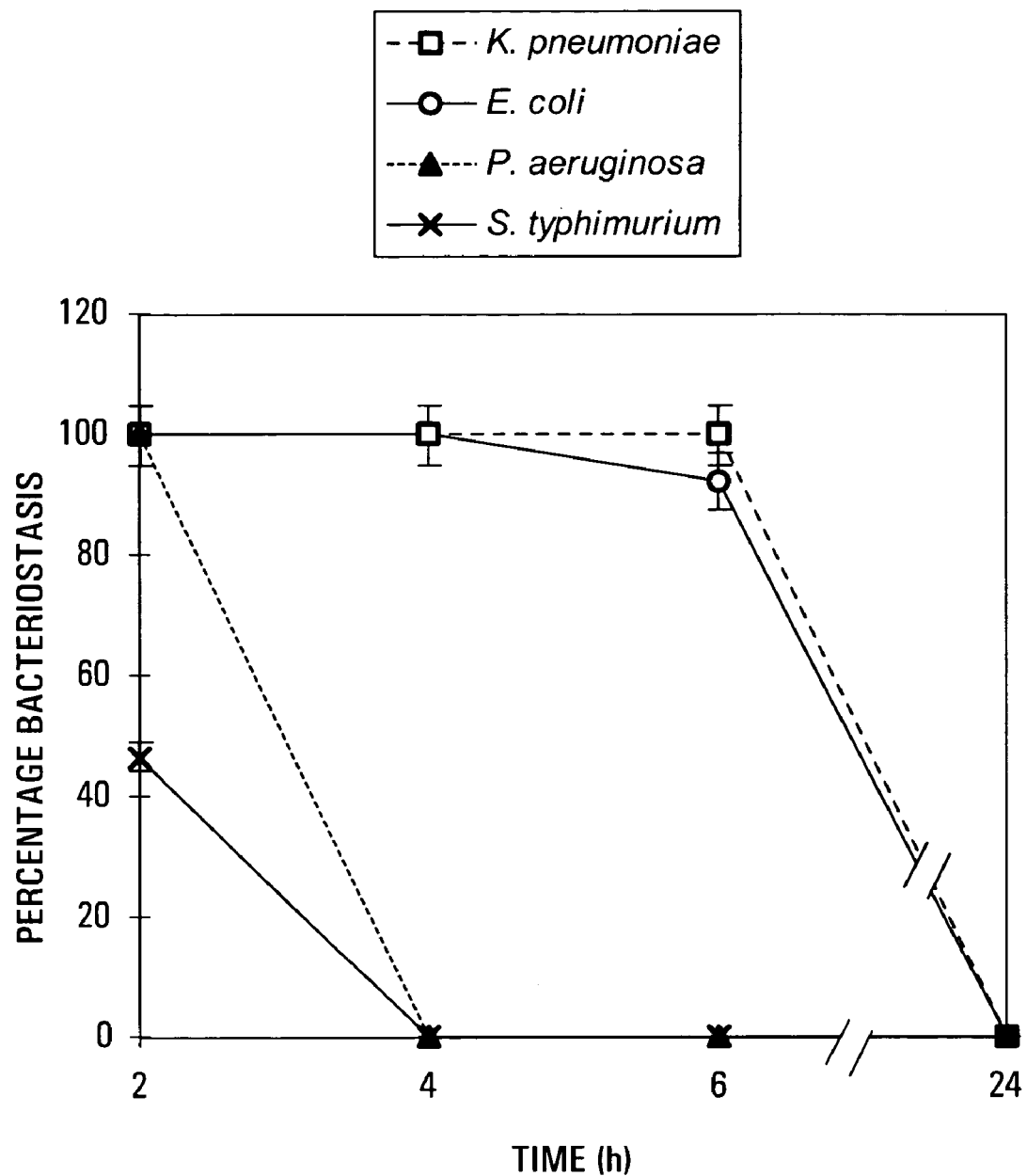

FIG. 30. Bacteriostasis induced by rFC produced in baculovirus-infected Sf9 cells in cultures of different Gram-negative bacteria.

Figure 31:
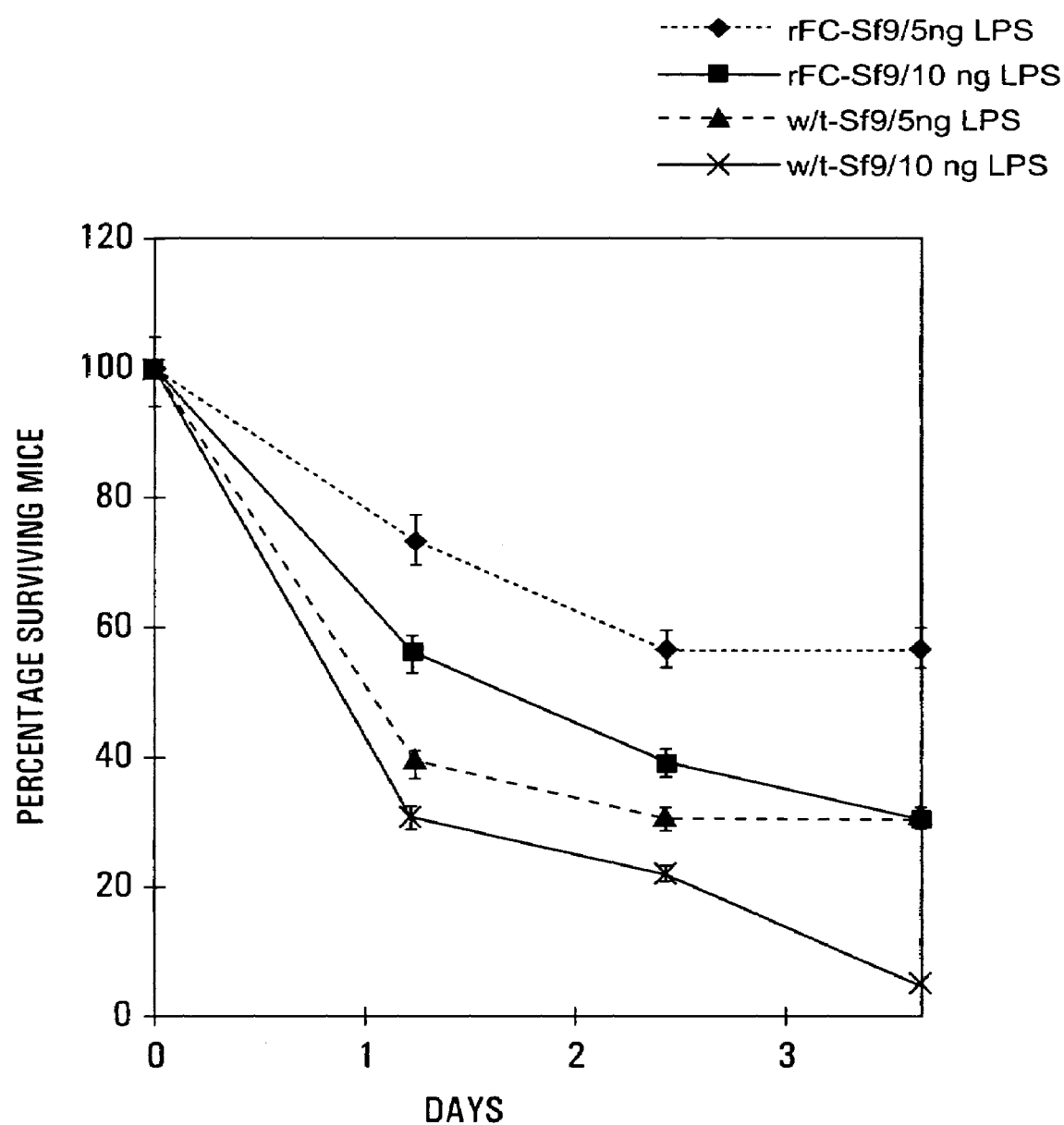

FIG. 31. Protection of mice from LPS lethality by administration of rFC produced in baculovirus-infected Sf9 cells.

BRIEF DESCRIPTION OF TABLES

Table 1 presents a comparison between binding affinity for lipid A of Factor C-derived sushi proteins and other LPS-binding proteins.

Table 2 presents a comparison of $MBC_{50}$, $MBC_{90}$, hemolytic activity, and cytotoxic activity of sushi and other cationic peptides on test microorganisms.

Table 3 provides indicators of LPS-binding, anti-LPS, and antimicrobial activities of Factor C and various peptides. In Table 3, column I shows affinity for LPS binding of peptide to Lipid A immobilized on an HPA chip, column II shows Hill's Coefficient—the stoichiometry of binding of the number of peptide molecules to 1 LPS molecule, column III shows Circular Dichroism (CD) analysis of peptide structures in the presence of 0.75 nM lipid A (α-H: α-helical; β: β-sheet; T: turn; R: random), column IV shows neutralization ($EC_{50}$)—µM of peptide needed to neutralize 50% of 200 EU/ml of LPS-induced LAL reaction, column V shows the amount of peptide needed to cause 50% suppresion of LPS-induced cytokine release (TNF-α), column VI shows mouse protection assays—2 ng LPS pre-incubated with peptide for 30 minutes before injection into C57/BL, column VII shows cytotoxicity (cell lysis) assays—for S4-S9:

$EC_{50}$=[peptide] to cause 50% lysis cytotoxicity, column VIII shows hemolytic activity at 100 µg peptide, and column IX shows $MBC_{90}$ (microbicidal concentration of peptide that kills 90% of bacteria) or $MIC_{90}$ (minimal inhibitory concentration of peptide that inhibits 90% of bacteria).

DETAILED DESCRIPTION OF THE INVENTION

The present invention provides efficient, high affinity recombinant proteins and peptides for gram-negative bacterial endotoxin. These molecules can be used, among other things, for: (a) anti-microbial, anti-endotoxin, anti-sepsis therapeutics; (b) tracing and detection or localization of gram-negative bacteria via, for example, the GFP component of SSCrFCsushi-GFP fusion proteins; and (c) development of LPS-specific affinity chromatography systems to purify endotoxin-contaminated samples or biological fluids.

The present invention lies in part in methods for treating bacteremia using proteins that bind to bacterial endotoxin as a therapeutic agent. A particularly effective protein is a recombinant Factor C protein, or any portion thereof that retains the biological activity of binding to lipid A.

cDNAs encoding Factor C proteins from *Carcinoscorpius rotundicauda* have been previously described (10,73). Recombinant Factor C from *Carcinoscorpius rotundicauda* (rCrFC) has been produced in vitro by coupled transcription/translation systems. However, the present invention resides partly in the development of in vivo systems, especially using insect cells as the host cell, for efficient production of rFC by expression of cloned DNA.

Also, the protection of rFC from activation and subsequent self-proteolysis by binding of endotoxin which may be present in solutions used in isolation of the protein is described in U.S. Pat. No. 5,716,834, the entire disclosure of which is hereby incorporated by reference. Basically, dimethylsulfoxide ($Me_2SO$ or DMSO) is added to solutions which are used during the purification process. Even greater protection of the rFC is achieved by also adding an agent effective for chelating divalent metal ions to the purification solutions.

cDNAs appropriate for expression in the presently-described system can be cDNAs encoding Factor C of any horseshoe crab. Two representative nucleotide sequences are presented as SEQ ID NO:1 and SEQ ID NO:3 (encoding the amino acid sequences of SEQ ID NOs:2 and 4). A composite DNA sequence, assembled from incomplete cDNA fragments, encoding the Factor C of *Tachypleus tridentatus* is disclosed by Muta et al (49).

Factor C appropriate for use in the present invention can be produced by any method typical in the art, but is preferably made in a eukaryotic host cell. Production of rFC in yeast host-vector systems is described in reference 75. Recombinant Factor C produced in yeast is found to lack serine protease activity, but, as shown in the working examples below, protein produced in yeast is still effective in both lipid A and endotoxin binding and in inducing bacteriostasis. Production of rFC in yeast host-vector systems is described in detail in co-pending U.S. Pat. No. 5,985,590. Recombinant Factor C for use in the invention can also be produced by a baculovirus host-vector system or in another suitable insect cell host-vector system, such as one for *Drosophila* cells. Co-pending U.S. patent applications Ser. Nos. 09/081,767 (now abandoned, a countinuation-in-part application of which issued to U.S. Pat. No. 6,645,724), 60/106,426 (the applicaton from which U.S. Pat. No. 6,733,997 claims priority) and 09/201,786 (now abandoned, a continuation-in-part application of which issued to U.S. Pat. No. 6,645,724) provide detailed description of production of rFC in such systems.

The endotoxin/lipid A-binding domain of Factor C lies within the amino terminal portion of the protein encompassed by rFCES; that is, the first 350 amino acids, numbered as in SEQ. ID. NO. 4. Referring to FIG. 28, endotoxin/lipid A binding activity is found in the truncated rFCEE (amino acids 1-766), rFCES (amino acids 29-330), rFC (sushi-1) (amino adds 29-201) and rFC (sushi-3) (amino acids 264-330). Molecular modeling studies suggest that the contacts are made by portions of the protein lying in the cysteine-rich domain, especially amino acids 60-70, in the sushi-1 domain, especially amino acids 170-185 and in the sushi2 domain, especially amino acids 270-280. Thus, a protein having at least these three portions of Factor C, which can be joined by a random amino acid sequence or by other chemical linkage, is expected to be useful in the method of the present invention.

As noted above, naturally-occurring Factor C proteins, and rFC that is full-length and produced in baculovirus-infected or other insect cell lines, possesses a serine protease activity. That activity is activated by endotoxin or lipid A binding. It might be found that the serine protease activity of the rFC produces undesired side effects when treating a subject with rFC according to the invention. Thus, in preferred embodiments of the present invention, the serine protease activity of the rFC is inactivated, either chemically or by mutation, or the domain providing that activity is deleted from the protein.

The portion of Factor C from horseshoe crab that constitutes the serine protease domain is approximately from amino acid 760 to the carboxy terminus of the protein, numbered as in SEQ. ID. NO.:4. Furthermore, the particular amino acids that constitute the catalytic residues are His809, Asp865, and Ser966. Thus, inactivation of these residues by chemical modification or by site-specific mutation can be used to provide rFC that will bind to lipid A, but lacks serine protease activity.

Chemical modifications to inactivate serine protease activity are well-known in the art. Methods for introducing site-specific mutations into any particular polypeptide are also well-known in the art.

Colorimetric and fluorescent assays for the serine protease activity of rFC are described in detail in co-pending application Ser. No. 09/081,767 (now abandoned, a continuation-in-part application of which issued to U.S. Pat. No. 6,645,724), the entire disclosure of which is hereby incorporated by reference. These assays are appropriate for screening mutant forms of rFC for serine protease activity. Assays for lipid A and endotoxin binding is also described in co-pending application Ser. No. 09/081,767 (now abandoned, a continuation-in-part application of which issued to U.S. Pat. No. 6,645,724) that can be used to ascertain that the serine protease-deficient mutant retains the lipid A/endotoxin binding activity required if the protein is to be used in the present invention.

"Stringent conditions" for hybridization are those that provide for hybridization of sequences having less than 15% mismatch, preferably less than 10% mismatch, most preferably 0% to 5% mismatch. Exemplary of such conditions, using probes of 50 bases or longer, are an aqueous solution of 0.9 M NaCl at 65° C.; an aqueous solution of 0.98 M NaCl, 20% formamide at 42-45° C. The conditions will vary according to the length of the probe, its G+C content and other variables as known to the skilled practitioner (54).

Exemplary wash conditions following hybridization are an aqueous solution of 0.9 M NaCl at 45-65° C., preferably 55-65° C. Lower salt, or addition of an organic solvent such as formamide, in the wash buffer will increase the stringency of the condition as known in the art.

A preferred hybridization condition is at 42° C. in 50% formamide, 5×SSC, 1× Denhardt's solution, 20 mM phosphate buffer, pH 6.5, 50 μg/ml calf thymus DNA, 0.1% SDS. Salt and temperature conditions equivalent to the hybridization conditions employed can be calculated from the following equation:

$$T_m=81.5° C.-16.6(\log_{10}[Na^+])+0.41(\% G+C)-0.63(\% \text{ formamide})-(600/l)$$

where l=the length of the hybrid in base pairs.

A preferred washing condition is in 1×SSC, 0.1% SDS washing solution at room temperature, followed by washing at high stringency with 0.1×SSC, 0.1% SDS at 42° C. and 2× with 0.1×SSC/0.1% SDS for 15 min. each at 42° C.

Preferred versions of rFC for use in the method of the invention are those encoded by polynucleotides that will hybridize to a nucleic acid having the sequence of SEQ. ID. NO. 1 or SEQ. ID. NO. 3 under stringent conditions. Most preferred versions of rFC are those having the amino acid sequence of SEQ. ID. NO. 2 or SEQ. ID. NO. 4.

For administration to a subject for treatment of bacterial infection or to induce bacteriostasis, the rFC is formulated with pharmaceutically acceptable carriers appropriate for the route of administration. Formulation of polypeptides for administration is known in the art; the practitioner is referred, for example, to reference 79. The route of administration is not particularly limiting of the invention, but preferred routes are intraperitoneal, intravenous and topical administration.

The proteins for administration are preferably formulated in pharmaceutical saline solutions such as 0.9% saline, phosphate buffered saline and the like. The polypeptides can be provided in lyophilized form and reconstituted for administration. The final concentration of the protein in the formulation administered is one that would provide a suitable dosage as described below.

Polypeptide therapeutic agents are known to be susceptible to degradation in the body, usually due to the action of proteolytic enzymes. Thus, the rFC administered according to the present invention might desirably be derivatized to inhibit such degradation. For example, carboxy-terminal amidation of the protein is known in the art to inhibit degradation by proteases present in serum. Particular derivations of proteins to improve their resistance to degradation in vivo and methods for accomplishing them are well-known in the art.

The dosage to be administered will of course be tailored to the particular form of rFC administered and the route of administration. Tailoring of dosage is considered within the skill of the routine practitioner. A dosage within the range 0.01 to 3 mg/kg body weight is acceptable; preferably the dosage will be within the range of 0.1 to 3 mg/kg, most preferably in the range of 0.3 to 0.4 mg/kg.

Doses may be administered either by bolus or by infusion. The particular rate of administration will be determined partly by the half-life of the protein in the body, which will be influenced by the particular structure of the protein and also by the route of administration. Assessment of pharmacokinetics necessary to determine the precise rate and dosage of the particular protein to be administered is considered within the skill of the practitioner.

The following exemplary embodiments of the invention serve to illustrate the invention. The examples are not to be considered limiting of the scope of the invention, which is defined only by the claims following.

EXAMPLE 1

Purification of Stably Expressed and Secreted Recombinant SSCrFCES

Stable cell lines of *Drosophila* S2 clones expressing SSCrFCES (U.S. Pat. No. 6,733,997) were routinely cultured in serum-free DES Expression medium and maintained at 25° C. in a humidified incubator.

The medium containing SSCrFCES was initially concentrated and desalted via 3 rounds of ultrafiltration using a 10 kDa cutoff membrane in an Amicon stirred cell (Millipore). Affinity chromatography purification under denaturing conditions yielded a 38 kDa protein of interest, in addition to a 67 kDa protein. Western blot analysis indicated that the 67 kDa protein does not contain the carboxyl poly-His tag. Thus this larger protein is likely due to non-specific adsorption to the resin.

(b) Purification of SSCrFCES by Preparative Isoelectric Membrane Electrophoresis Typically, 2 liters of conditioned medium were initially subjected to successive ultrafiltration using a 100 kDa and 10 kDa molecular weight cutoff with the Pellicon system (Millipore). The medium was concentrated seven-fold. The enriched SSCrFCES was purified to isoelectric homogeneity using Preparative Isoelectric Membrane Electrophoresis (Hoefer IsoPrime™, Pharmacia). The pI of the SSCrFCES was determined to be 7.1 at 4° C. A set of four membranes were made, with pHs of 6.5, 7.0, 7.25, and 7.5. The concentration of acrylamido buffers used for the membranes were calculated based on information in Righetti and Giaffreda (17). The four membranes were assembled in order, from acidic to basic, to delimit five chambers. Each sample reservoir vessel was filled with 30 ml of pyrogen-free water and pre-run at 4° C. at 4 Watts constant power (3000 V limiting, 20 mA maximum) for two hours.

After removing the pre-run water, the protein sample was placed in sample reservoir vessel corresponding to the chamber delimited by pH 7.0 and 7.25. The IsoPrime was conducted under the same conditions for 3-4 days without detrimental effect on the protein, and the content from each chamber was analyzed on a 12% SDS-PAGE. The scheme reported here has been found to be reproducible in our laboratory throughout the course of approximately two years. The overall recovery of SSCrFCES binding capacity is nearly 90%. This is attributable to its extreme stability conferred by the presence of 9 disulfide bonds.

(c) Analysis of the Purified SSCrFCES

Figure 1A:
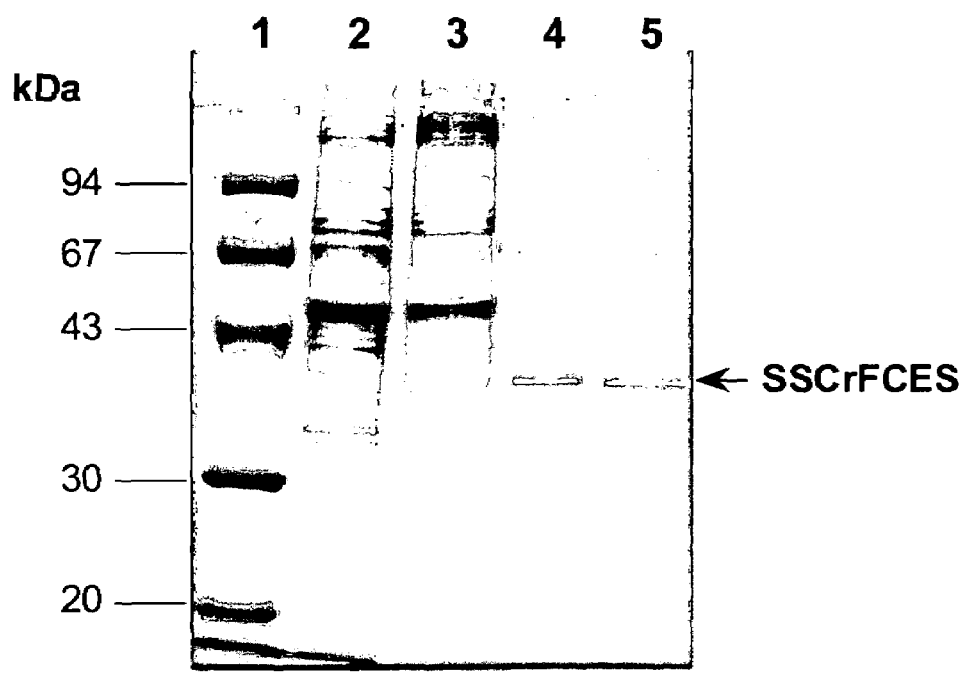
Figure 1B:
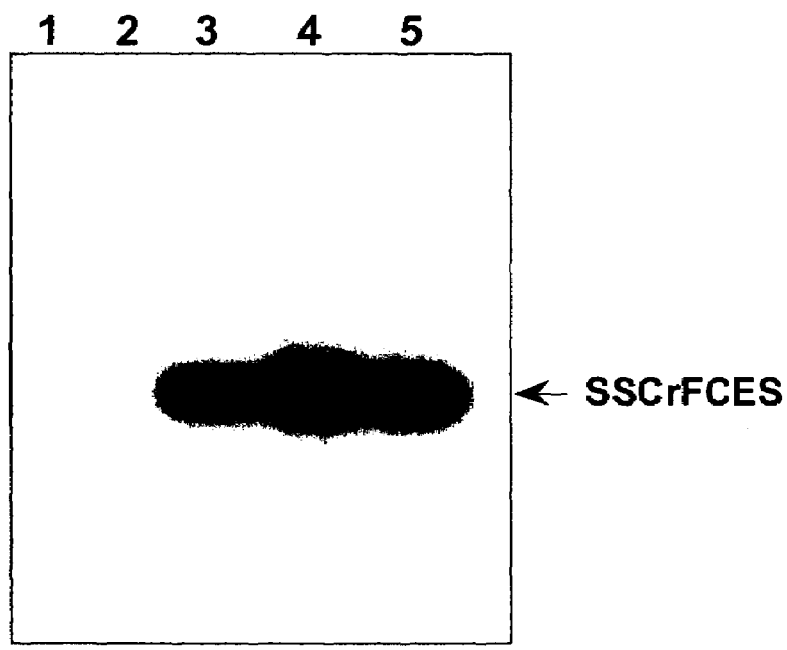

The distribution of the protein was identified using Chemiluminescent Western blot. SDS-PAGE analysis of *Drosophila* cells transformed with the recombinant vector is shown in FIG. 1A. The Western blot revealed the presence of a protein with an apparent molecular weight of ~38 kDa (FIG. 1B). SSCrFCES in medium represented >90% of the total recombinant protein expression. When stable cell line was cultured in serum-free medium without hygromycin for a week in a 1 L-Bellco spinner flask, a typical yield ~1.6 mg/L of SSCrFCES was achieved.

The presence of SSCrFCES in the culture medium thus contributes to the ease of batch-continuous culture and purification. Most significantly, SSCrFCES expressed and secreted from insect cells was biologically active.

EXAMPLE 2

ELISA-Based Lipid A Binding Assay

A Polysorp™ 96-well plate (Nunc) was first coated with 100 μl per well of various concentrations of lipid A diluted in pyrogen-free PBS. The plate was sealed and allowed to incubate overnight at room temperature. The wells were aspirated and washed 6 times with 200 μl per wash solution (PBS containing 0.01% Tween-20 and 0.01% thimerosal). Blocking of unoccupied sites was achieved using wash solution containing 0.2% BSA for 1 hour at room temperature. Subsequently, blocking solution was removed and the wells washed as described above. Varying concentrations of SSCrFCES were allowed to interact with bound lipid A at room temperature for 2 hours.

Bound SSCrFCES was detected by sequential incubation with rabbit anti-SSCrFCES antibody (1:1000 dilution) and goat anti-rabbit antibody conjugated with HRP (1:2000 dilution) (Dako). Incubation with each antibody was for 1 h at 37° C. with washing between incubations as described above. In the final step, 100 μl of peroxide substrate ABTS (Boehringer Mannheim) was added. Using a microtiter plate reader, the absorbance of the samples was determined at 405 nm with reference wavelength at 490 nm. The values were correlated to the amount of LPS bound and SSCrFCES present. Quantitation of SSCrFCES was achieved from a standard curve derived by immobilizing known amount of purified SSCrFCES onto a Maxisorp plate.

Figure 2A:
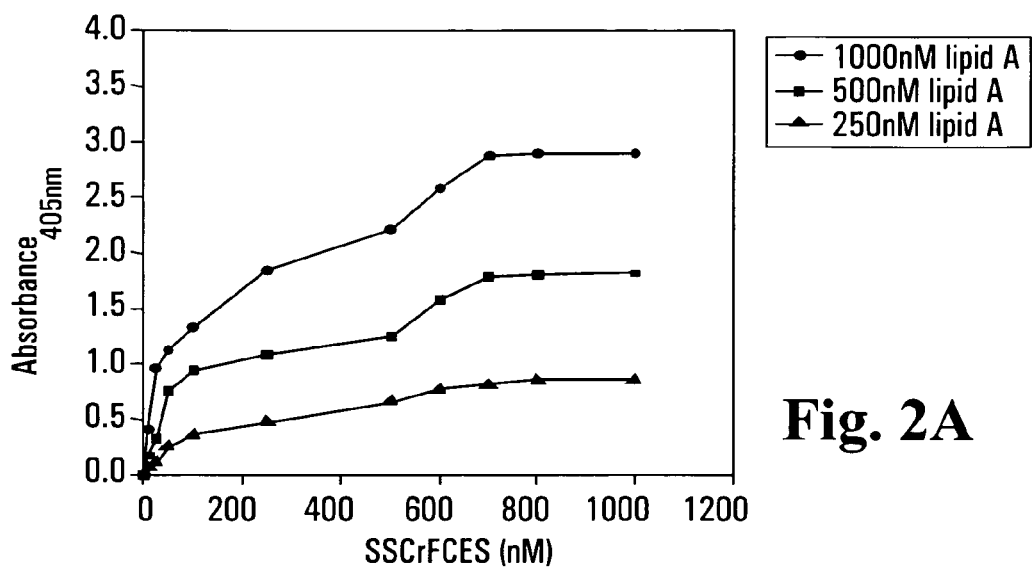
Figure 2B:
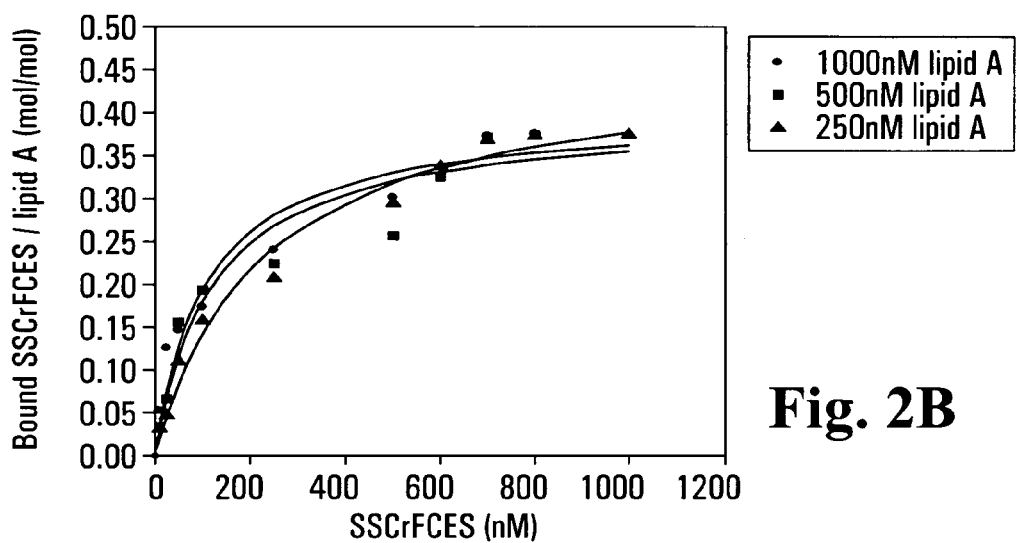
Figure 2C:
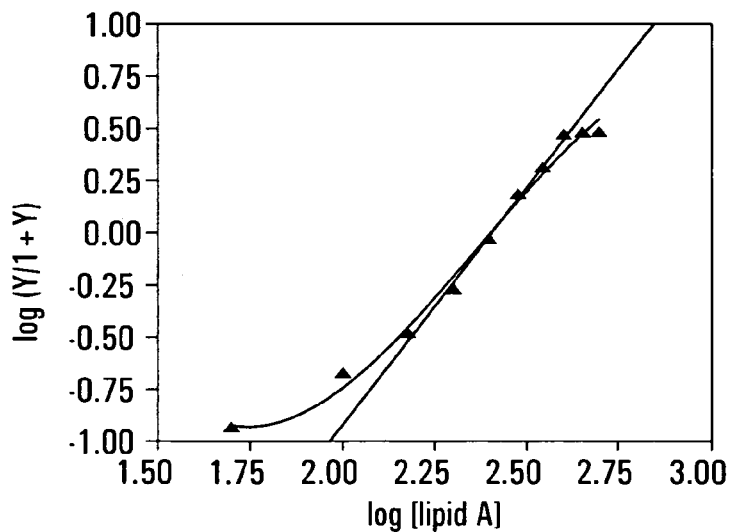

Results from the ELISA-based lipid A binding assay displayed a biphasic curve (FIG. 2A). Unlike other LPS-binding proteins (18-21), SSCrFCES has multiple binding sites for the ligand. SSCrFCES binds co-operatively to lipid A with a stoichiometry of one SSCrFCES to ~3 lipid A molecules at saturation (FIG. 2B). Scatchard plots of the binding data are very convex, indicating that the binding of SSCrFCES to lipid A is highly cooperative, being comparable to haemoglobin for oxygen (22). This is confirmed by the slope of the line obtained from plotting the data (FIG. 2C) according to the Hill's equation (23), which gave a coefficient of 2.2. While bactericidal/permeability-increasing protein (BPI) (18) was reported to bind >1 lipid A molecule, it was not reported to exhibit cooperativity in binding. This homotropic cooperativity for binding to lipid A is thus novel and unique to SSCrFCES.

The presence of multiple lipid A binding sites that showed cooperativity assuredly confirm the LPS-binding domain of Factor C, as well as full-length Factor C, to be the best candidate for removal and detection of endotoxin in solution, and supports its use as an anti-endotoxin therapeutic. Cooperative binding also contributed to Factor C's ability to detect sub-picogram level of endotoxin (U.S. patent application Ser. No. 09/081,767, now abandoned, a continuation-in-part application of which issued to U.S. Pat. No. 6,645,724) as well as a competitive binding advantage over Limulus Anti-LPS Binding Factor (LALF).

Retrospectively, the degranulation of amoebocytes in the presence of LPS would release a battery of anti-bacterial/LPS binding factors e.g. LALF, thus significantly reducing the amount of free LPS. Nonetheless, Factor C is capable of capturing trace LPS to activate the coagulation cascade. Such capability is attributed to its homotropic cooperativity as demonstrated by SSCrFCES, that is to say, its LPS-binding domain.

EXAMPLE 3

Surface Plasmon Resonance (SPR) Studies on Biospecific Binding Kinetics Between Lipid A and: CrFCES; SSCrFCsushi-1,2,3-GFP; SSCrFCsushi-1-GFP; SSCrFCsushi-3-GFP; and Synthetic Peptides Recognition of lipid A by the abovenamed secreted recombinant proteins and peptides was, performed with a BIAcore X™ biosensor instrument and an HPA sensor chip. Briefly, lipid A at 0.5 mg/ml in PBS was immobilized to a HPA sensor chip (Pharmacia) according to the manufacturer's specification. In all experiments, pyrogen-free PBS was used as the running buffer at a flow rate of 10 μl/min.

With purified SSCrFCES, 4 μg/ml was injected into the flow cell at a rate of 10 μl/min, and the binding response was measured as a function of time. Following injection of SSCrFCES, a solution of INDIA™ HisProbe™-HRP antibody, diluted in PBS to 400 μg/ml, was also injected to cause a shift in SPR in order to further confirm that SSCrFCES binds to lipid A. For regeneration, 100 mM of NaOH solution was injected for 5 minutes. Similar lipid A binding analysis was carried out with SSCrFCsushi-GFP fusion proteins.

Figure 3A:
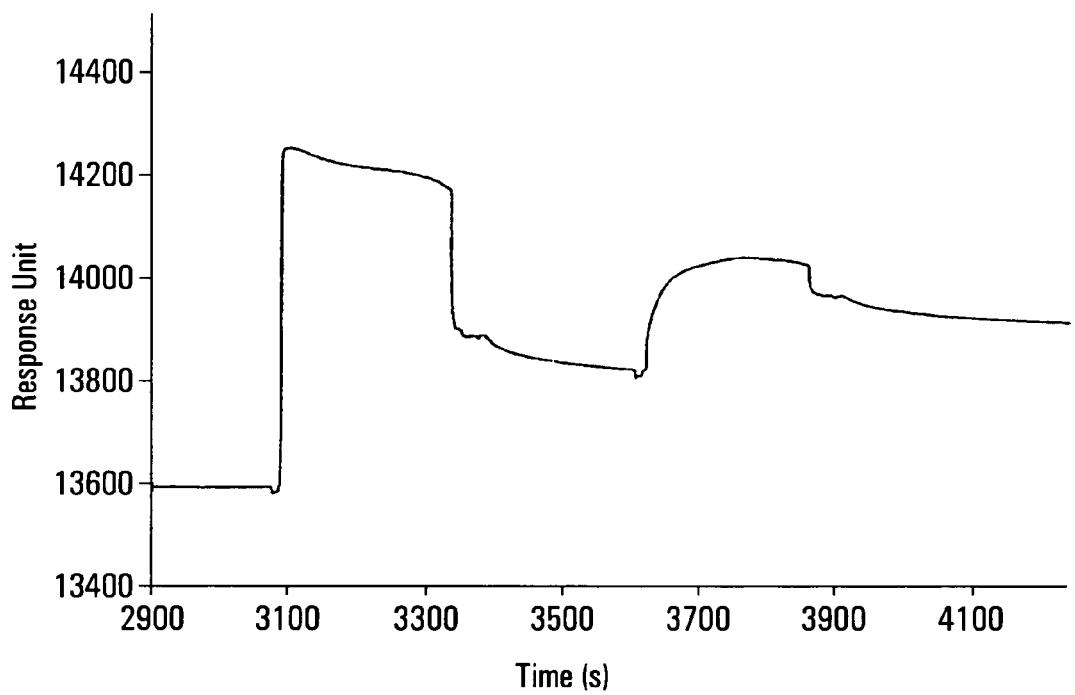
FIG. 3(B) is a sensogram depicting the interaction of SSCrFCsushi-1,2,3-GFP with immobilized lipid A.
FIG. 3(C) is a sensogram depicting the interaction of SSCrFCsushi-1-GFP with immobilized lipid A.
FIG. 3(D) is a sensogram depicting the interaction of SSCrFCsushi-3-GFP with immobilized lipid A.
FIG. 3(E) is a sensogram depicting the interaction of certain synthetic peptides with immobilized lipid A. The table (inset to E) shows the binding properties of the synthetic peptides to lipid A.

FIG. 3A shows that injection of 400 ng/100 ul of SSCrFCES over immobilized lipid A resulted in an increase of ~200 relative response unit. This represents a 92% saturation of lipid A. Subsequently, injection of antibody (INDIA™ His-HRP Ab) against the poly-His tag of SSCrFCES resulted in a further increase of relative response unit. The binding of INDIA™ His-HRP Ab further confirms that only SSCrFCES was bound to the immobilized lipid A.

Figure 3B:
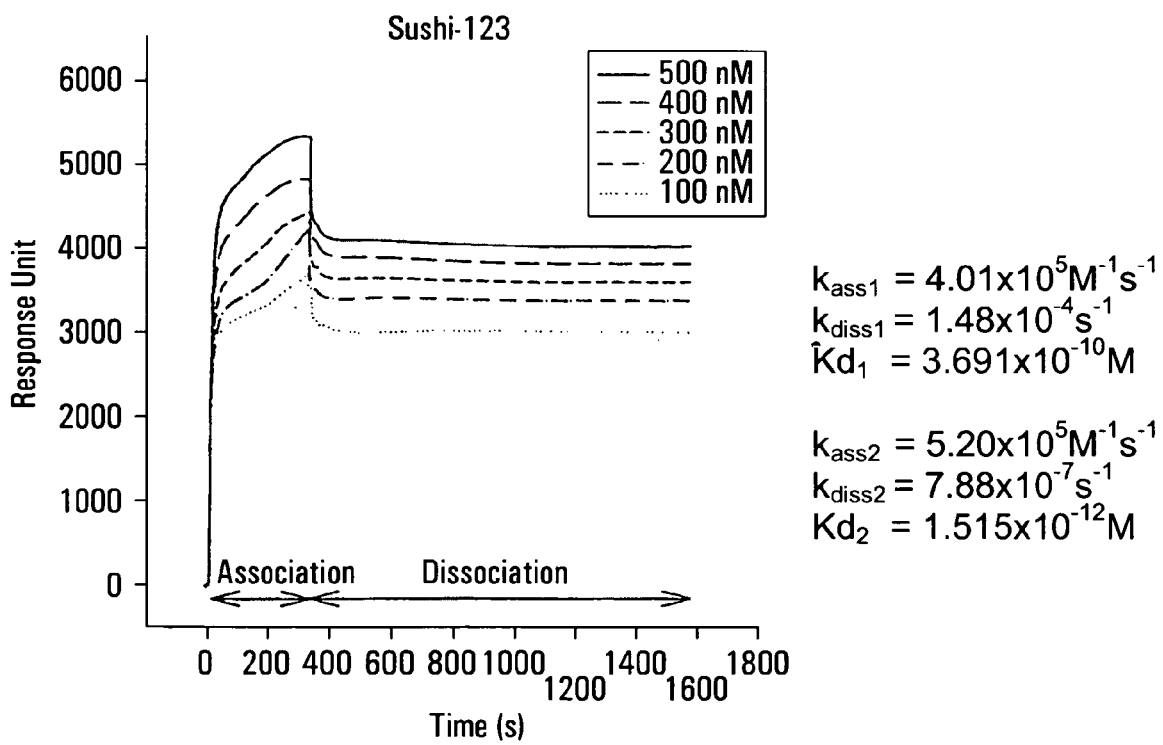
Figure 3C:
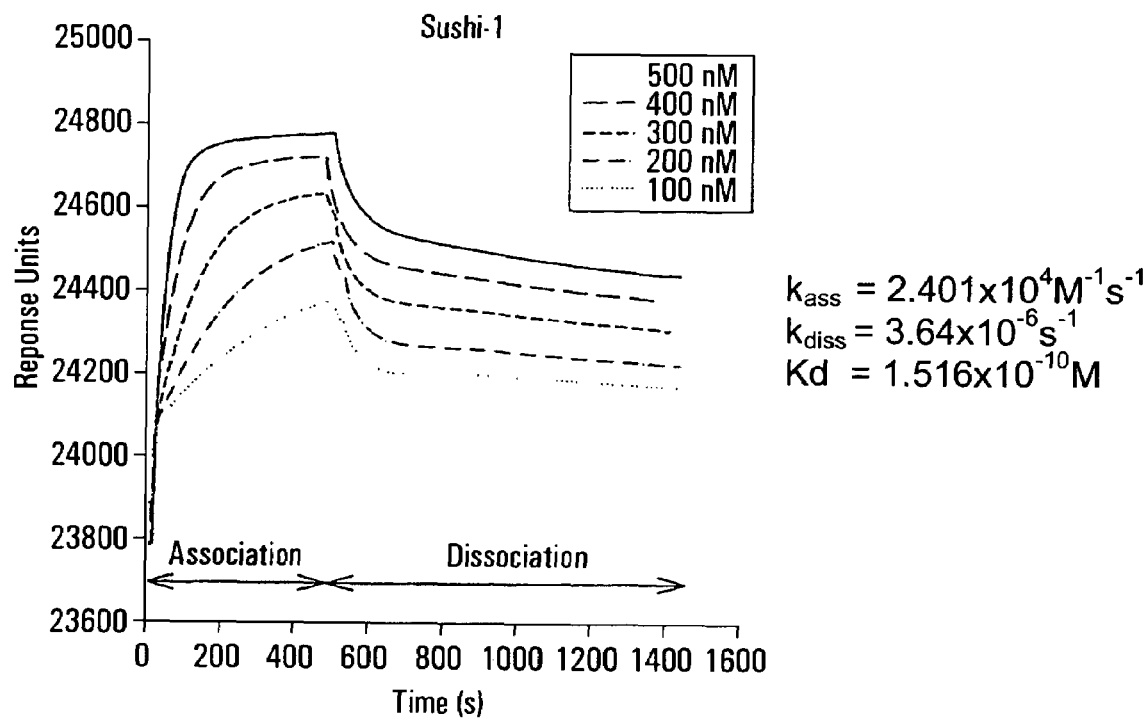
Figure 3D:
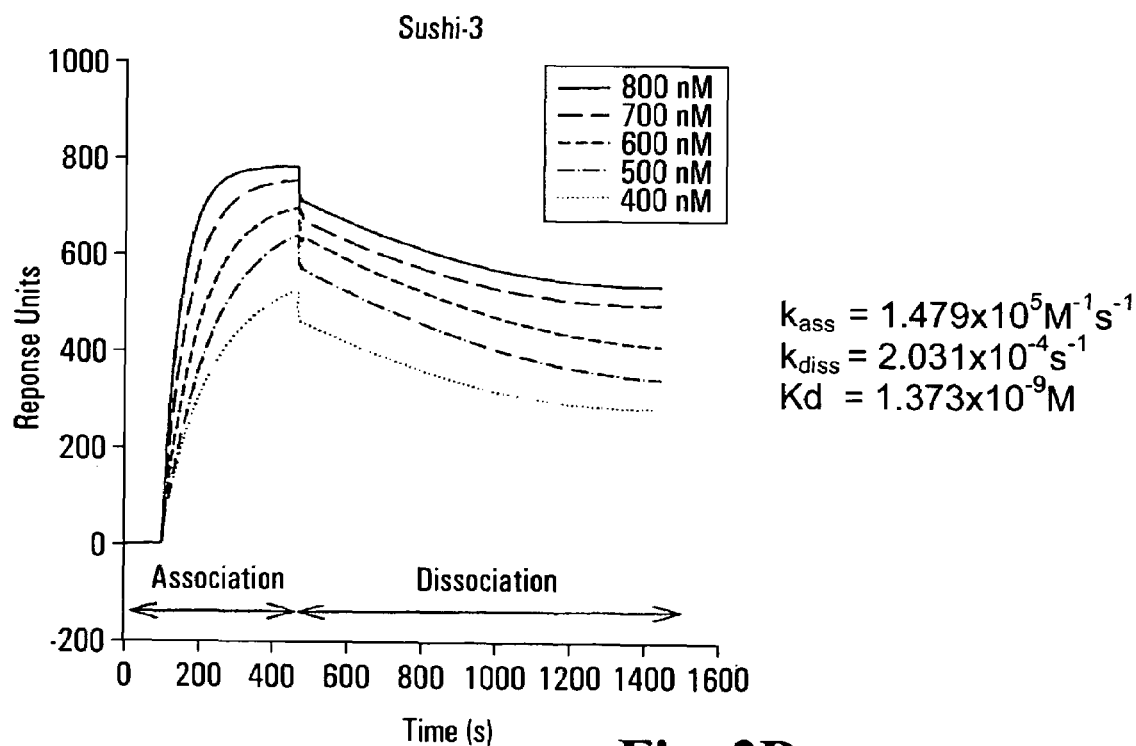
Figure 3E:
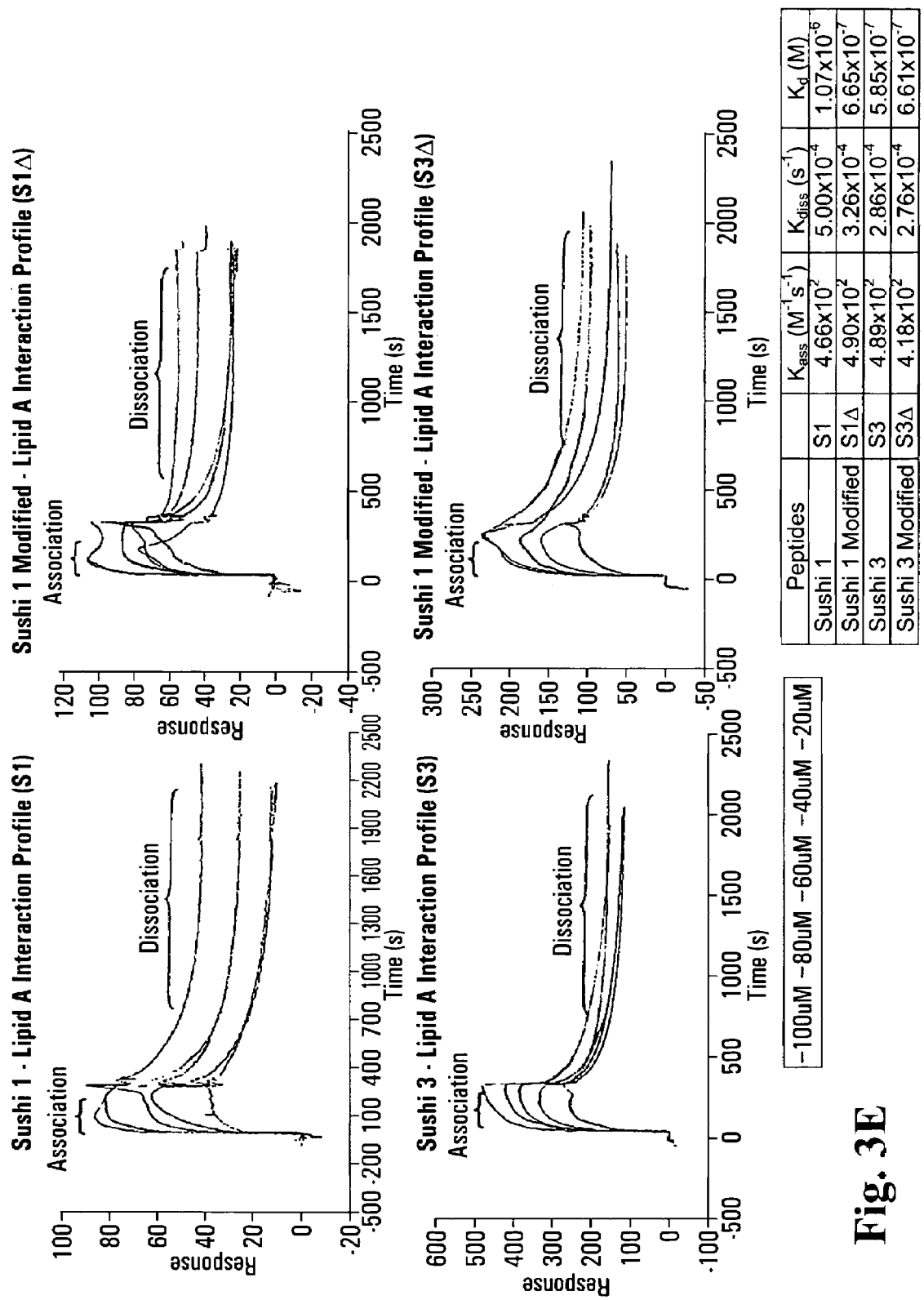

FIGS. 3B, 3C, and 3D show SPR (in response units) of the realtime binding interactions between SSCrFCsushi-1,2,3, SSCrFCsushi-1, and SSCrFCsushi-3-GFP fusion proteins, respectively, to the immobilized lipid A on the biochip. FIG. 3E shows the same binding interaction analysis of four examples of synthetic peptides derived from sushi-1 and sushi-3 of Factor C.

EXAMPLE 4

SSCrFCES and Synthetic Peptides Are Potent Anti-endotoxin Molecules—(Inhibition of Endotoxin-induced LAL Reaction)

The *Limulus* Kinetic-QCL is a quantitative, kinetic assay for the detection of gram-negative bacterial endotoxin. This assay utilizes the initial part of LAL endotoxin reaction to activate an enzyme, which in turn releases p-nitroaniline from a synthetic substrate, producing a yellow color. The time required before the appearance of a yellow color is inversely proportional to the amount of endotoxin present. Throughout the assay, the absorbance at 405 nm of each well of the microplate was monitored. Using the initial absorbance reading of each well as its own blank, the time required for the absorbance to increase 0.200 absorbance units were calculated as Reaction Time. The 50% endotoxin-neutralizlng concentration ($ENC_{50}$) reflects the potency of SSCrFCES or the synthetic peptides; a low $ENC_{50}$ indicates high anti-endotoxin potency.

Briefly, 25 μl of endotoxin solution (LPS, *E. coli* 055:B5) at 200 EU/ml was mixed with an equal volume of SSCrFCES at 1 μM, in a series of 2-fold dilutions in LAL reagent water in disposable endotoxin-free glass dilution tubes (BioWhittaker) and incubated at 37° C. for one hour. The reaction mixtures were each diluted 1000-fold with LAL reagent water. The endotoxin activity was then quantified with *Limulus* Kinetic-QCL. One hundred µl of the diluted test mixture was carefully dispensed into the appropriate wells of an endotoxin-free microtitre plate (Costar). The plate was then pre-incubated for >10 minutes in a temperature-controlled ELISA plate reader. Near the end of the pre-incubation period, 100 µl of freshly reconstituted Kinetic-QCL reagent was dispensed into the wells using an 8-channel multipipettor. The absorbance at 405 nm of each well of the microtitre plate was monitored at time intervals of 5 minutes over a period of 2 hours. A 5 second automix was activated prior to reading. In the *Limulus* Kinetic-QCL, the assay was activated by 0.005 EU/ml of endotoxin.

The high sensitivity of the assay allowed for very low levels of endotoxin to be detected. Following incubation of endotoxin with SSCrFCES, a 1000-fold dilution was introduced to eliminate any potential effects of the SSCrFCES on the LAL enzyme system. A sigmoidal curve is usually expected between relative reaction time and the logarithmic concentration of the SSCrFCES. The best fit curve was derived using SigmaPlot and the concentration corresponding to 50% relative increase in reaction time was designated $ENC_{50}$. The mean values were obtained from 3 independent experiments.

The time that is required before the appearance of a yellow color (Reaction Time) is inversely proportional to the amount of endotoxin present. A low $ENC_{50}$ indicates high potency of endotoxin neutralization. The $ENC_{50}$ is taken as the concentration of SSCrFCES that reduces the mean reaction time by 50%. A sigmoidal curve was obtained between relative reaction time and the logarithmic concentration of SSCrFCES (FIG. 4). $ENC_{50}$ of SSCrFCES was determined to be 0.069±0.014 µM. Comparatively, this value is 28- and 7.5-fold less than $ENC_{50}$ of polymyxin B and LF-33 (33-mer peptide derived from lactoferrin) (24), respectively. This shows that on a molar basis, much less SSCrFCES is required to neutralize the same amount of LPS. Consequently, it also indicates that SSCrFCES is a potent anti-pyrogenic recombinant protein.

The $ENC_{50}$ of the synthetic sushi peptides were comparable to other reported peptides, e.g.: S1=2.25 µM; S1Δ=0.875 µM; S3=1 µM; A3=0.625 µM. For the designed peptides, the $ENC_{50}$ values were: V1=0.47 µM and V2=0.89 µM.

Hill's plot for the interaction between synthetic peptides and lipid A shows that S1 exhibited high positive co-operativity of n=2.42, indicating that more than two S1 peptides interact with one LPS molecule.

EXAMPLE 5

The Anti-sepsis Activities of SSCrFCES and Synthetic Peptides: Inhibition of the LPS-induced TNF-α and IL-8 by (a) THP-1 Cells (b) Human Peripheral Blood Mononuclear Cells (PBMC)

During gram-negative bacterial septicaemia, the high concentration of LPS in the blood leads to multiple organ failure syndromes. These adverse effects are dependent on the generation of endogenous mediators. A multitude of mediators have been implicated, including arachidonic acid metabolites, PAF, cytokines such as TNF-α, interferons, and various interleukins (e.g. IL-1, IL-8, etc.), reactive oxygen metabolites, and components of the coagulation cascade (1-3). Consequently, the biological potential of SSCrFCES to bind and neutralize LPS-stimulated production of cytokines in human promonomyelocytic cell line THP-1 and normal human PBMC were investigated.

Results from our in vitro binding studies suggested that SSCrFCES would be a potent inhibitor of the LPS activation of monocytes. To test this prediction, we measured the ability of SSCrFCES to inhibit hTNF-α and hIL-8 production by THP-1 cells incubated with 25 ng/ml and 100 ng/ml of LPS in a serum-free system containing various concentrations of SSCrFCES. THP-1 cells were grown in RPMI 1640 medium supplemented with 10% FBS, penicillin (100 U/ml) and streptomycin (0.1 mg/ml), at 37° C. in a humidified environment in the presence of 5% $CO_2$. The cells were maintained at a density between $2.5 \times 10^5$ and $2.5 \times 10^6$ cells/ml.

THP-1 cells were prepared for experiment by addition of a concentrated stock solution of phorbol myristate acetate (PMA, 0.3. mg/ml in dimethyl sulfoxide) to cell suspension to give a final concentration of 30 ng/ml PMA and 0.01% dimethyl sulfoxide (25). PMA-treated cell suspensions were immediately plated into 96-well microtitre plate at a density of $4 \times 10^5$ cells/ml and allowed to differentiate for 48 hours at 37° C. Immediately before stimulation by 25 ng/ml LPS or LPS pre-incubated with various concentrations of SSCrFCES, the culture medium was removed, and the cells were washed twice with serum-free RPMI 1640 and incubated at 37° C. At indicated times, the culture medium was collected. Human TNF-α and IL-8 concentrations in the supernatants were assayed using ELISA as suggested by the manufacturer.

Heparinised venous blood drawn from healthy donors was subjected to fractionation using Ficoll-Paque PWS (Pharmacia) to obtain peripheral blood mononuclear cells (PBMC). PBMC were washed with PBS and suspended at a cell density of $1.5 \times 10^6$ cell/ml with RPMI 1640 medium supplemented with 10% FBS. PBMC were incubated at 37° C. for 24 h at a density of $1.5 \times 10^5$ per well. LPS stimulation and immunoassay of hTNF-α and hIL-8 were performed as described for THP-1 cells. In addition, the suppressive effect of SSCrFCES on LPS-induced cytokine release was investigated in the presence of 10% human serum. The difference between the test and control groups was subjected to Student's t-test. The values were obtained from at least three independent experiments.

FIG. 5 shows that with THP-1 cells, 0.5 µM of SSCrFCES potently inhibited >90% LPS-induced production of TNF-α and IL-8 in the presence of high level of endotoxin. At 25 ng/ml LPS concentration tested, 0.7 µM of SSCrFCES is sufficient to completely prevent LPS-induced TNF-α production (FIG. 5A). At 100 ng/ml LPS, 1 µM of SSCrFCES reduced 90% IL-8 production as compared to control (FIG. 5B).

Our findings indicate that 1 µM of SSCrFCES effectively prevent the LPS-mediated induction of hTNF-α and hIL-8 production by THP-1 when these cells were incubated in the presence of high endotoxin levels. It is important to note that the concentrations of LPS (25 ng/ml and 100 ng/ml) used in these studies are among the highest known concentrations reported for LPS-induced cytokine production. On molar basis, SSCrFCES appears to be more potent than polymyxin B and LF-33 at suppressing LPS-induced LAL coagulation and hTNF-α or hIL-8 secretion by THP-1 cells under serum-free conditions (24). This suggests that SSCrFCES has a much greater intrinsic capacity to neutralize endotoxin than polymyxin B. Again, it is attributable to its cooperative binding of LPS.

Purified human PBMC were used to test the suppression of endotoxin-induced TNF-α and IL-8 secretion by SSCr- FCES under normal physiological conditions. In the absence of human serum, addition of only 0.1 µM of SSCrFCES completely inhibited TNF-α and IL-8 response to 10 ng/ml LPS by 50% (FIGS. 6A and 6B). When SSCrFCES was added to human serum (final concentration, 10%) before the addition of endotoxin, the suppressive effect of SSCrFCES was attenuated. It required 17 fold more SSCrFCES to suppress TNF-α and IL-8 secretion by 50%. A similar effect of human serum has also been observed with other cationic anti-endotoxin proteins such as LF-33 (24) and LALF (26). This is due to the interaction of these factors with serum proteins that effectively reduce their availability for binding to endotoxin. However, if the SSCrFCES was mixed with endotoxin 5 min before the addition of serum, the effect of the serum on the neutralization of endotoxin by SSCrFCES was greatly reduced, requiring only 4 fold more SSCrFCES for 50% inhibition (FIGS. 6A and 6B).

Results from the in vitro binding studies suggested that the 4 Factor C-based sushi peptides would be potent inhibitors of the LPS-induced cytokine release by monocytes. To test this prediction, we measured the ability of S1, S1Δ, S3, and S3Δ to inhibit hTNF-α production by THP-1 cells incubated with 10 ng/ml of LPS in a serum-free system containing various concentrations of peptides.

As shown in FIG. 6C, both modified peptides, S1Δ and S3Δ, are more potent inhibitors, giving 50% inhibition at 53.3 and 45.8 µM, respectively, as compared to the S1 and S3 peptides.

With the designed peptides (V1 and V2) 50% inhibition of LPS-induced TNF-α release were 27 and 35 µM, respectively.

EXAMPLE 6

SSCrFCES and Synthetic Peptides Are Not Cytotoxic to Eukaryotic Cells

In addition to high specific LPS binding, an important feature when using proteins for in vivo application to treat Gram-negative bacterial septic shock, are their physico-chemical properties in biological systems. Problems that often arise in animal experiments are due to toxicity, as in the case of polymyxin B, or a very short half-life in the circulating system, for example BPI. To assess these features, we investigated SSCrFCES for their ability to permeabilize cultured cells.

Two×$10^4$ THP-1 monocytes in 50 µl of RPMI 1640 were mixed in a microtitre plate with 50 µl of increasing amount of 2-fold serial dilutions of SSCrFCES (0.004-4.0 mg/ml in PBS) and incubated for 60 min at 37° C. To determine cytotoxicity induced by the SSCrFCES, 20 µl of CellTiter96™ AQ$_{ueous}$ One Solution Reagent (Promega) was added into each well for 90 min at 37° C. [3-(4,5-dimethylthiazol-2-yl)-5-(3-carboxymethoxyphenyl)-2-(4-sulfophenyl)-2H-tetrazolium (MTS) is bioreduced by metabolically active cells into a colored formazan product that is soluble in tissue culture medium (27, 28). For detection, the absorbance was measured at 490 nm. To determine the ratio of cell lysis induced by SSCrFCES, two controls were used. Complete lysis (100%) was achieved by incubating cells in phosphate buffer saline containing 0.2% Tween-20 instead of medium only. This absorbance value corresponded to the background, as those cells could not metabolize MTS. The second control representing 0% lysis was determined by incubating cells in medium only. The $LD_{50}$ was calculated as the concentration of SSCrFCES necessary to lyse 50% of the cells. The experiment was done in triplicate.

SSCrFCES had minimal effect on cell permeabilization (FIG. 7). At the highest concentration of 4 mg/ml or 109 µM, only 20% cell lysis was observed. Compared to polymixin B where 50% cell lysis occurred with 0.51 mg/ml (29), this clearly indicates that SSCrFCES is a non-toxic anti-endotoxin protein. The synthetic peptides are non-cytotoxic.

EXAMPLE 7

Pharmacokinetic Analysis of SSCrFCES—Clearance Rate in Mice

600 µg of SSCrFCES was labeled with biotin using EZ-Link™ PEO-Maleimide Activated Biotin (Pierce) according to the manufacturer's instructions. The excess biotin was subsequently removed via ultrafiltration through Microcon-10 (Millipore). Three C57BL/6J mice were given a single i.v. bolus injection of 200 µg biotin-labeled SSCrFCES. Blood was collected from each of the 3 mice at time intervals over a 5-h period. The blood was immediately treated with SDS-PAGE loading dye and boiled for 5 minutes. The mixture was resolved in a 12% SDS-PAGE and electroblotted onto a PVDF membrane. Immunoblotting and hybridisation were carried out as described above except NeutrAvidin™-HRP antibody (Pierce) was used. Exposure time for chemiluminescence detection was extended to 1 hour. The signal on the X-ray film was quantitated via densitometric scan. The clearance rate of biotin-labeled SSCrFCES was analyzed using NCOMP, which is a WINDOWS-based program for noncompartmental analysis of pharmacokinetic data (30).

Densitometric scan revealed that significant amounts of circulating half-life of SSCrFCES is sufficiently long to allow easy detection during the first 90 minutes post-injection. NCOMP, which provides an interactive graphical environment for noncompartmental analysis of pharmacokinetics data by facilitating estimation of the zero and first moments of concentration-time data, was used for analysis. The calculated clearance rate of biotin-labeled SSCrFCES in C57BL/6J mice is 4.7 ml/min (FIG. 8). The clearance rate is 2.7 fold slower than BPI. Therefore, a lower dose of SSCrFCES would be adequate to maintain high enough circulating levels to compete with LBP for LPS.

EXAMPLE 8

SSCrFCES and Synthetic Peptides Neutralize LPS-induced Lethality in Mice

The anti-endotoxin potency of SSCrFCES was investigated in C57BL/6J mice. Mice are typically resistant to endotoxin. However, the sensitivity of mice to endotoxin can be enhanced >1,000-fold by co-injection with a liver-specific inhibitor, galactosamine (31). In our study, intraperitoneal (i.p.) injection of 2.5 ng of E. coli 055:B5 LPS together with 15 mg of galactosamine hydrochloride in 0.2 ml of saline induced nearly 100% lethality in 18-25 g C57BL/6J mice within 7 hours. Various concentrations of SSCrFCES (1, 2, and 4 µM) and synthetic peptides (25 and 75 µg) were injected intravenously (i.v.) through tail vein 10 minutes after i.p. injection of the LPS-galactosamine mixture. Lethality was observed over 3 days after injection. Statistical analysis were performed using the Kaplan-Meier test (32) and log rank pairwise test.

As shown in FIG. 9A, the LPS-induced lethality was reduced by 20% when 1 µM of SSCrFCES was injected i.v.

10 min after the i.p. injection of LPS. Higher concentrations of SSCrFCES of 2 and 4 μM conferred 90% and 100% protection, respectively.

A protective role of SSCrFCES viz LPS-binding domain of Factor C is thus shown in an intraperitoneal murine sepsis model. The mechanism by which SSCrFCES protects mice from LPS-induced sepsis is presumably mediated through its high affinity association to lipid A moiety of LPS, which consequently reduces the secretion of cytokines like TNF-α and IL-8. FIG. 9B shows that S1, S1Δ, and S3 conferred 22-100% protection, whereas at 75 μg, S3Δ was most efficacious, giving 100% protection against LPS-induced toxicity.

EXAMPLE 9

Antimicrobial Action

Recently, the concept of eradication via targeted disruption of bacterial LPS by cationic peptides/proteins was introduced (33). For an effective antimicrobial therapy, such peptides need to satisfy several important criteria, including potent antimicrobial activity over a wide range of pH, fast killing rate, low toxicity, and low hemolytic activity. While numerous antimicrobial peptides/proteins, like FALL-39 (34), SMAP-29 (35), lepidopteran cecropin (36), and CAP-18 (37) have been reported, few display all the above mentioned attributes. Thus, the search for new, more powerful and yet safe antimicrobial peptides continues to enrich the therapeutic armamentarium.

Further analysis of the sushi peptides showed them to have low cytotoxicity and to be capable of neutralizing LPS-biotoxicity (See Examples 4, 5, and 6 above). This property provides a vital advantage over other antimicrobial peptides in suppressing adverse effects of LPS-induced septic shock during or after treatment.

Septic shock is characterized by a drastic fall in blood pressure, cardiovascular collapse, and multiple organ failure. Septic shock is responsible for over 100,000 deaths a year in the US alone. The septic shock condition (38, 39) often creates more complication than the actual infection itself when a massive amount of LPS is released by bacteria disintegrated by antibiotics. This problem is especially pronounced in children, in the elderly, and in immuno-compromised patients.

The present invention demonstrates novel and hitherto unsurpassed antimicrobial action of Factor C sushi peptides against clinical isolates of *P. aeruginosa*. Although the sushi peptides are demonstrated to be efficacious against this microorganism, antimicrobial potency is not limited to *P. aeruginosa* but should extend to any bacterium producing LPS bound by Factor C.

Antimicrobial action of SSCrFCES, SSCrFCsushi-GFP proteins and synthetic peptides (e.g., S1, S1Δ, S3, S3Δ, and V peptides), examined by microbiocidal concentrations ($MBC_{90}$) assays, show that these recombinant proteins and synthetic peptides have potent antimicrobial activities. Antimicrobial activity is expressly demonstrated against *Pseudomonas aeruginosa* and *Klebsiella pneumoniae* and *Helicobacter pylori*. However, the antimicrobial activity of these proteins and peptides is not limited to only these three species of bacteria.

Peptides of 34 amino acids were synthesized based on the sequence of two regions of Factor C: sushi 1 and sushi 3, as well as their corresponding mutants (sushi 1Δ and sushi 3Δ), were found to harbour strong antimicrobial activities. Collectively, all four peptides (named S1, S1Δ, S3, and S3Δ) demonstrated exceptionally effective bactericidal activity against gram-negative bacteria, represented by *Pseudomonas aeruginosa*.

At 0.03-0.25 μg/ml (8-63 nM), the $MBC_{90}$ values of the peptides, are of the lowest ever reported against *Pseudomonads*. Viable bacteria were reduced by 90% after 7 minutes and were totally eradicated within 30-40 minutes. These peptides were minimally hemolytic against both rabbit and human erythrocytes (30%) at concentrations of 100 μg/ml (25 μM), which is up to 3333 times their effective MBC concentration.

These findings demonstrate the unprecedented therapeutic value of the sushi peptides and their mutants for treatment of *Pseudomonas* infections. Other sushi peptide derivatives (S4, S5) were also found to have variable antimicrobial activities. Thus, these results are given by way of example, and the present invention should not be deemed to be limited to only these representative peptides.

Test strains cultured on Mueller-Hinton agar (MHA, Becton Dickinson, USA) were inoculated into 10 ml Mueller-Hinton broth (MHB, Becton Dickinson, USA) and grown overnight at 37° C. in a shaker incubator (Model 4536, Forma Scientific, Inc., USA) at 230 rpm. Overnight broth cultures were diluted to give a final cell density of $10^5$ colony forming units/ml (cfu/ml). One hundred microliters of the bacterial suspension was dispensed into sterile polypropylene 8-strip PCR-tubes (Quality Scientific Plastics, USA). Eleven microliters of serially diluted sushi peptides, ranging in final concentrations of 0.03-4 μg/ml, were then added. The peptides were constituted at 10 times the required test concentrations in 0.01% acetic acid and 0.2% bovine serum albumin (BSA). Positive controls were cultures without test peptides. Uninoculated MHB was used as negative control. All tests were carried out in triplicate.

Cultures were incubated at 37° C. for 18-24 h, with the PCR-tubes held in horizontal position and shaken at 230 rpm. Cell counts were determined by standard drop-count method. The killing efficiency for the four sushi peptides were calculated based on standard drop-count method. All four peptides (S1, SΔ1, S3, and SΔ3) showed potent bactericidal activity of <0.03-0.25 μg/ml against the 30 clinical strains of *P. aeruginosa* (Table 2).

The $MBC_{50}$ determined for all the 4 peptides was <0.03 μg/ml (<7.5-8.0 nM). The $MBC_{90}$ for the peptides were: <0.03 μg/ml (8 nM) for S1; 0.06 μg/ml (16 nM) for SΔ1; <0.03 μg/ml (8 nM) for S3; and 0.25 μg/ml (63 nM) for SΔ3. These $MBC_{90}$ values are unsurpassed by any known antimicrobial peptides reported for *P. aeruginosa*. The $MBC_{90}$ for the control strain of *P. aeruginosa* ATCC 27853 was 0.03 μg/ml (7.5-8.0 nM) for all the 4 peptides (FIG. 12).

The antimicrobial therapeutic value of sushi peptides is exhibited by their exceptional bactericidal activity against gram-negative bacteria, e.g.: 30 clinical isolates and a control strain of *P. aeruginosa* ATCC 27853. The resistance pattern of these strains gave a close representation of the resistant strains of *P. aeruginosa* found in Singapore (Table 2).

The remarkably low $MBC_{90}$ values of <0.03-0.25 μg/ml (<8.0-63 nM) obtained for the peptides are unsurpassed by any known antibiotics of metabolite or peptide origin. Comparatively, sushi peptides are 1-3 orders of magnitude more effective against *P. aeruginosa* than are other reported antimicrobial peptides. Owing to their high affinity for LPS, the sushi peptides probably exert anti-*n Pseudomonas* effect through disruption of the LPS-lamellar organization.

Although, the peptides are targeted at the conserved lipid A domain, different MBCs were observed over the 30 clinical isolates. This is most likely due to differential permeability of the peptides into the variable polysaccharide components in the different *Pseudomonas* strains. This is supported by the different binding affinities of the sushi peptides for *Escherichia coli* B5:055 lipid A (See Example 3 of the present application).

The killing rate assay was adapted from the MBC test above, with different contact time of peptides with the bacteria arrested at regular intervals and plated for colony count. An initial density of $10^9$ cfu/ml was used. FIG. 13 shows that sushi peptides exhibit rapid bactericidal action. This is one of the important features of an effective therapeutic agent.

With an effectively low $MBC_{90}$ concentration, we proceeded to investigate the killing time for the sushi peptides. At 0.06 μg/ml, all four peptides achieved $MBC_{90}$ within 7 minutes. Within 30 minutes, the peptides totally eradicated an initial cell population of $1 \times 10^9$ cfu/ml (FIGS. 13 and 14). *P. aeruginosa* is a fast-replicating bacteria, which displays a short lag phase and doubling time. Hence, a rapid bactericidal action is an extremely important factor especially with an infection that occur near or in vital organs like cornea (contact lens contamination in the eye), lung (in cystic fibrosis), and acute bacteraemia in AIDS patients. At a concentration of 0.06 ug/ml, the sushi peptides were able to eradicate 90% of viable cells within 7 min of incubation (FIG. 13).

Complete eradication is assured to occur within the first two generations of bacteria which reduces the possibility of mutation. Thus, this rapid killing rate reduces the chance/opportunity for the development of resistance. Resistance will be remote as it will require several precise mutations occurring at multiple enzymes along the LPS synthesis pathway to ultimately yield a modified LPS structure that is sufficiently different to evade sushi peptide recognition. However, the possibility of developed or acquired resistance cannot be precluded if some of these strains are allowed to mutate at sub-lethal peptide concentrations.

FIG. 15 shows electron micrographs illustrating how some multiple antibiotic-resistant strains of bacteria are killed by these peptides.

Human and rabbit erythrocytes were both used to test the hemolytic activities of the peptides. Whole blood was collected in heparinized sterile syringe, transferred to sterile borosilicate tube and centrifuged at 1200 g for 5 minutes at 4° C. The supernatant including the leukocytes above the erythrocyte pellet was discarded. The erythrocytes were washed 3 times using three volumes of prechilled pyrogen-free saline (PFS). An erythrocyte suspension at 0.4% was prepared for the hemolysis assay. Serial two-fold dilutions of the peptides was prepared in PFS and 100 μl aliquots were added to equal volumes of 0.4% erythrocyte solution in a 96-well microtiter plate (Nunclon™ Δ surface, Nunc) to give final peptide concentrations ranging from 6 to 100 μg/ml. The mixtures were incubated at 37° C. for 1 h. The intact erythrocytes were then pelleted by centrifuging at 1000 g for 5 min. One hundred μl of the supernatant was transferred to a new 96-well microtiter plate and the amount of hemoglobin released into the supernatant was determined by reading the absorbance at 414 nm using a SPECTRAmax™ 340 plate reader with SOFTmax PRO™ version 1.2.0. A positive control with 100 μl of 0.4% erythrocyte lysed in 1% Triton-X 100 was taken as 100% lysis. The negative control was the erythrocytes in PFS alone, which gave minimal lysis. This was taken as 0%.

FIG. 16 shows that sushi peptides have low hemolytic activity. This is crucial to the applicability of an antimicrobial agent for therapeutic use in humans and animals. Even at concentrations of 100 μg/ml (25 μM), up to 400-3333 fold of their $MBC_{90}$, the sushi peptides showed minimal hemolytic activity (FIG. 16). On a separate assay, the hemolytic activity of sushi peptides was tested on rabbit erythrocytes. At the same concentration, the peptides showed hemolytic activity below 6%. For purposes of the present application, the language "substantially free of hemolytic activity" means showing hemolytic activity below 6%.

Thus, the ability of sushi peptides to: (a) cause effective LPS-neutralization (see Examples 4 and 5); (b) confer crucial protection against LPS-induced lethality in mice (see Example 8); (c) possess low $MBC_{90}$ values; (d) induce rapid killing rate; and (e) exhibit lack of hemolytic activity, are features that indicate that these peptides will provide great advantages over currently available antibiotics.

With this invention, the LPS toxicity during the course of treatment will be dramatically reduced. The sushi peptides will provide highly effective and potentially useful therapeutics for the treatment of *P. aeruginosa* infections. It leaves very little doubt that these peptides will be equally effective against other members of *Pseudomonads*.

EXAMPLE 10

SSCrFCsushi-GFP Proteins Bind LPS and Gram-negative Bacteria

The recombinant SSCrFCESsushi-GFP proteins were able to bind/tag gram-negative bacteria, showing as green fluorescent tagged organisms. This makes a convenient detection tag for displaying such microogranisms in samples.

EXAMPLE 11

LPS-affinity Chromatography (for Removal of Endotoxin from Liquid Samples)

By way of an example, S3Δ peptide (with Kd of $10^{-7 \text{ to}}$ $_{-8}$ M) was chosen from amongst the sushi peptides to create an affinity chromatography system to display the power of binding of LPS from liquid samples. Thus, a solution of 4 mg/ml of S3Δ (in conjugation buffer: 0.1 M MES [2-(N-Morpholino)ethanesulfonic acid], 0.9% NaCl, pH 4.7) was immobilized via EDC [1-ethyl-3-(3-dimethylaminopropyl) cardiimide]/DADPA (Diaminodipropylamine), obtained from Pierce Chemicals, USA). After 3 hours of conjugation to DADPA-Agarose CL-6B in a small column, the flowthrough was collected and the absorption of fractions at 280 nm was measured to calculate the total amount of peptide immobilized to the matrix (by substraction from the unbound S3Δ found in the flowthrough).

It was found that binding efficiency of S3Δ to the EDC-activated resin was 50%. After regeneration of the column with 5 column volumes of 1% sodium deocycholate (DOC)—to ensure the removal of any exogenous LPS that may be bound to the resin, and washing the resin with pyrogen-free water, the column was ready for LPS absorption.

Again, by way of example, two 50 ml volumes of LPS solution (either LPS from Sigma, or FITC-labelled LPS from List Biologicals) containing 1 and 0.05 EU/ml were loaded onto the column. In each case, the flowthrough was subjected to LPS measurement by either LAL kinetic-QCL kit (BioWhittaker) or spectrofluorimetry, depending of the type of LPS solution that was used. In each case, the level of unbound LPS remaining in the flowthrough was below the detection limit (0.005 EU/ml) of the LAL kinetic-QCL assay. The affinity column was re-usable repeatedly, using 1% DOC as a regenerating agent.

LPS-affinity chromatography was also demonstrated by batchwise chromatography using 0.5 ml of 0.5 ug/ml FITC-LPS solution (in different buffers). The resin suspension was rotated for 3 h at room temperature, briefly spun at 1000 rpm for 1 min and the supernatant was reclarified at 12000 rpm for 10 minutes. The resultant supernatant was measured for unbound FITC-LPS by spectrofluorimetry. FIG. 17 shows S3Δ peptide-FITC-LPS coupled agarose beads seen under UV-fluorescence microscope.

The optimal binding of LPS to S3Δ was tested under different pH conditions and ionic strengths. Binding decreases with increase in ionic strength, and increases with increase in pH (FIG. 18). Thus, the best condition for binding of LPS to the affinity resin is basic and low ionic strength conditions. The optimal condition is expected to vary with different protein solutions.

Purified SSCrFCsushi-GFP proteins can also be chemically-linked to activated resins via their C-terminus GFP region, to allow N-terminal LPS-binding domain to be exposed for capturing endotoxin when an LPS-contaminated solution or biological fluid is passed through the resin.

EXAMPLE 12

Production of rFC in *P. pastoris*

In this study, the cloned Factor C cDNA of the Singapore horseshoe crab, *Carcinoscorpius rotundicauda* (10), was expressed in a methylotrophic yeast, *Pichia pastoris*. The full-length rFC so produced was found to lack serine protease activity, yet possess a functional endotoxin-binding domain. The full-length rFC from *P. pastoris* is able to bind free or bound LPS. Deletion proteins rFCEE and rFCSN containing the 5' and 3' regions, respectively, of Factor C were also produced and assayed for lipid A binding activity. The presence of a fully functional endotoxin-binding domain on the full-length rFC, and a slightly reduced endotoxin-binding capacity in rFCEE was demonstrated by two modified qualitative and quantitative LPS binding assays.

A. Materials and Methods (1) Glassware and Buffers

All glassware was rendered pyrogen-free by baking at 200° C. for 4 h. Buffers were prepared using pyrogen-free water (Baxter) and autoclaved at 121° C. for 2 h. Sterile disposable plasticware was used whenever possible. Other non-heat resistant apparatus was soaked in 3% hydrogen peroxide before rinsing with pyrogen-free water and drying in an oven.

(2) Recombinant Factor C Constructs

Three recombinant Factor C constructs—pHILD2CrFC21, pHILD2/CrFC21EE, and pPIC9/CrFC26SN (10,12,75)—were used for the study. As a control, pHILD2/151, an isolate of *P. pastoris* containing only the parent vector, pHILD2, was also included. pHILD2/CrFC21 contains the full-length CrFC21 cDNA (GenBank Database Accession No. S77063) of 3.4 kb together with its native translational start and signal sequence while pHILD2/CrFC21EE contains the 2.3 kb 5' EcoRI fragment isolated from CrFC21 cDNA. This construct contains the 762 amino acid fragment encompassing the heavy chain of CrFC21 along with its endotoxin-binding domain. The pPIC9/CrFC26SN construct contains the 2.4 kb 3' SalI-NotI fragment of CrFC26 (GenBank Database Accession No. S77064) cloned as a fusion fragment, in-frame and downstream of the pPIC9 vector start site and secretion signal. CrFC26SN contains sequence similar to the corresponding fragment in CrFC21 (10). This is a truncated construct lacking the putative LPS-binding domain and therefore, serves as a useful negative control in LPS-binding assays. The recombinant Factor C proteins from pHILD2/CrFC21, pHILD2/CrFC21EE, and pPIC9/CrFC21SN are referred to as rFC, rFCEE, and rFCSN, respectively.

(3) Growth Conditions

Recombinant *Pichia* clones of pHILD2/CrFC21, pHILD2/CrFC21EE and pPIC9/CrFC26SN as well as the negative control, pHILD2/151 were grown overnight in shake flasks at 300 rpm and 30° C. in 1 L MGY growth medium containing 1.34% yeast nitrogen base (Difco), 1% glycerol and $4 \times 10^{-5}$% biotin. At the mid-log phase of growth ($OD_{600}$ 2.0), the yeast cells were harvested aseptically at 3,000×g for 10 min and transferred to 2 L MM induction medium, containing 1.34% yeast nitrogen base (Difco), 0.5% methanol and $4 \times 10^{-5}$% biotin. Induction was carried out at 30° C. for 8 h. Induced cells were harvested by centrifugation at 3,000×g for 10 min.

(4) Preparation of rFC Samples from Recombinant Yeast Clones

Induced yeast cells were disrupted by 10 cycles of nebulization (Glas-Col™ BioNeb) at 200 psi using purified $N_2$. Soluble and insoluble fractions were separated by centrifugation at 13,200×g for 12 min. The supernatant containing soluble proteins was partially purified by ammonium sulfate precipitation at 20% saturation and resuspended in 50 mM Tris-Cl buffer, pH 8. The mixture was desalted through a Sephadex™ G-25 column (Pharmacia) equilibrated in the same buffer. In a separate preparation, the crude yeast supernatant was subjected to ultrafiltration through a Biomax™-50 (Millipore) membrane. The Biomax™-50 enriched rFC was further purified by chromatography through a Sephadex™G-100 column (1×25 cm; Pharmacia). Total protein was measured by Bradford assay (62).

(5) Western Analysis of rFC Protein rFC samples were electrophoresed on denaturing 10% SDS-polyacrylamide gel (63) and electroblotted onto Immobilon™ PVDF membrane. The respective rFC was immunolocalized by incubating the blot with rabbit anti-Factor C primary antibody and visualizing with horseradish peroxidase-conjugated secondary goat anti-rabbit antibody (Dako) using 4-chloro-1-naphthol and $H_2O_2$ as substrate.

(6) LPS-Binding Assay of rFC

LPS from *E. coli* 055:B5 (Sigma) was reconstituted to 2 μg/μl, and diphosphoryl lipid A from *E. coli* K12, D31m4 LPS (List Biologicals, Inc., USA) was made up to 1 μg/μl. The LPS-binding assay was based on modifications of earlier described protocols (45,61). Briefly, 10 μg aliquots of LPS/lipid A were electrophoresed on a denaturing 15% SDS-polyacrylamide gel and electroblotted onto Immobilon™ PVDF membrane. The membrane was cut into strips and each LPS/lipid A strip was subsequently incubated with 300 μg of proteins containing rFC. Detection of rFC binding to lipid A was accomplished by incubation with anti-Factor C antibody followed by alkaline phosphatase-conjugated secondary goat anti-rabbit antibody (Dako) and BCIP/NBT colorimetric substrate (Moss, Inc., USA).

(7) Assay for Competition Between rFC and CAL Factor C for LPS

*Carcinoscorpius* amoebocyte lysate (CAL) containing native Factor C was used in an assay in which rFC competed with CAL Factor C for LPS. Because the rFC produced in *P. pastoris* lacks serine protease activity, the competition can be monitored by measuring the reduced enzymatic activity of CAL in a fluorimetric assay. Mixtures of 100 μl each of increasing concentrations of LPS or rFC, in fluorimetric assay buffer (50 mM Tris HCl pH 8, containing 0.1 M NaCl and 0.01 M $CaCl_2$) were incubated at 37° C. for 1 h. Aliquots of 20 μg CAL were added to each mixture and the total volumes were made up to 2 ml with fluorimetric assay buffer. The reaction was continued at 37° C. for 1 h and the fluorimetric assay protocol (64) was followed. This involved the addition of 15 μl of 2 mM fluorimetric substrate N-t-Boc-Val-Pro-Arg-7-amido-4-methylcoumarin (Sigma) and incubation at 37° C. for 30 min. The reaction was terminated by the addition of 0.1 ml of glacial acetic acid (Merck). The product, amino methylcoumarin, was measured in fluorescence units (FU) on a Luminescence Spectrometer LS-5 (Perkin-Elmer) with excitation light at 380 nm and emission at 460 nm.

(8) Binding Interactions Between rFC and its Immobilized Ligand, Lipid A

The binding interactions between rFC and immobilized lipid A were monitored using the BIACORE X™ biosensor (Pharmacia Biotech). The BIACORE X™ sensor chip features a flat hydrophobic surface that allows the immobilization of ligand molecules. Thirty microliters of lipid A at 100 μg/ml were immobilized on each sensor chip to form a ligand surface. Biomax™-50 enriched samples of rFC, rFCEE and rFCSN, each at 1 mg/ml were injected at 10 μl/min for 3 min over the ligand surface. After each injection of the recombinant protein samples, the lipid A ligand surface was regenerated using 0.1 M NaOH. The ligand-binding was measured in relative response units (RU) for each sample, and calculated from the difference in RU at the baseline, viz., before injection of sample, and final experimental reading taken after sample injection and a 2-min wash. The percentage binding was thus determined.

B. Results and Discussion

Nebulization of *P. pastoris* Clones Released Soluble and Bioactive rFC.

After nebulization, the supernatant derived from clarification at 13,200 xg of the *P. pastoris* cell lysate contained soluble forms of rFC and rFCSN of 132 and 89 kDa protein bands, respectively (FIG. 19). Compared to glass bead treatment (61), nebulization enhanced the breakage efficiency of *P. pastoris*. Furthermore, the rFC was fractionated into the soluble phase, thus enabling its direct use for functional analysis, as well as ease of purification. This is a significant improvement over the earlier rFC preparations from glass-bead breakage where insoluble rFC had to be solubilized by treatment with detergents (12). Detergent-solubilization, in particular, with Triton X-100 has been reported to inhibit Factor C binding of LPS (68). We have also shown that SDS at >0.5% also inhibits the activity of Factor C in CAL. Removal of SDS using potassium chloride (69) restores the LPS binding activity of solubilized rFC. However, care must be taken to avoid pyrogenation. Thus, it is best to obtain soluble rFC under pyrogen-free conditions via physical methods and not chemical means.

Using either $(NH_4)_2SO_4$ precipitation or Biomax™-50 ultrafiltration, the rFC preparation was enriched in total protein content. Chromatography of Biomax™-50 rFC through a Sephadex™ G-100 molecular sieve further purified rFC from other yeast proteins (FIG. 20).

In the modified Western blot of LPS, rFC was shown to bind to the lipid A moiety displaying specific bands in the range of 7-20 kDa (FIG. 21A) which is consistent with previous findings (43,70). Subsequently, when the modified Western blot of diphosphoryl lipid A was used, the specificity of rFC for lipid A was further confirmed (FIG. 21B). Recombinant Factor C samples derived from $(NH_4)_2SO_4$ precipitation; Biomax™-50 ultrafiltration and Sephadex™ G-100 gel filtration displayed increasing affinity for lipid A (FIGS. 21A and 21B: Lanes 3 & 4). No binding to the 7-20 kDa bands was observed with rFCSN and pHILD2/151. Biomax™-50 enriched rFCEE, the truncated Factor C, was also able to bind specifically to lipid A moiety of LPS, albeit less strongly (FIGS. 21A and 21B).

The presence of a functional LPS-binding domain demonstrates that rFC expressed in yeast folds properly, or at least its endotoxin-binding domain does so. The postulated endotoxin-binding region of the *C. rotundicauda* Factor C (61) is located in the amino terminus of the heavy chain, which comprises the cysteine-rich EGF-like domain and one or two sushi domains (16,71). Recombinant Factor C specifically binds to the lipid A moiety showing the ability of rFC to recognize and bind the biologically-potent moiety of LPS. That the binding of LPS to Factor C requires the presence of an endotoxin-binding domain was confirmed using the rFCSN where the lack of 5'-terminal LPS-binding domain in this deletion homolog resulted in its inability to bind lipid A. The observable reduction in intensity of binding of rFCEE to lipid A as compared to that of rFC indicates that although the binding of lipid A requires the presence of the LPS-binding domain, sequences of Factor C further downstream may mediate the strength of the binding. It has been reported that binding of endotoxin triggers a conformational change in the Factor C molecule (58) where downstream sushi domains are involved in protein-protein interaction.

Recombinant Factor C competes for LPS, causing reduction in enzymatic activity of CAL Factor C. The yeast rFC, lacking serine protease activity, but capable of binding to LPS, was observed to compete with CAL native Factor C for the LPS. This resulted in the depletion of LPS available to bind native Factor C, thus causing a reduction in its enzymatic activity (55).

The percentage competition by rFC of the native Factor C enzyme activity of CAL was calculated based on comparison of enzyme activity with the negative control of pHILD2/151. The following formula was employed:

$$\frac{(FU \text{ of } LPS \text{ in } pHILD2/151 + CAL) - (FU \text{ of } LPS \text{ in } rFC + CAL) \times 100\%}{FU \text{ of } LPS \text{ in } pHILD2/151 + CAL}$$

where FU represents fluorescence units.

The competitive effect of crude rFC on LPS-activated CAL Factor C enzymatic activity was compared with the two partially purified rFC samples based on the above formula. Partial purification of rFC using $(NH_4)_2SO_4$ precipitation improved its competitive effect from 30% to 60%. Enrichment of rFC through Biomax™-50 improved its inhibitory efficiency to 81%.

A checkerboard analysis of fixed amount of rFC with variable concentrations of LPS was used to investigate binding efficacy and the ratio of interaction between rFC and LPS molecules. A comparison was made between the binding efficacy of crude rFC and Biomax™-50 rFC to LPS. FIG. 4A shows that increasing amounts of rFC resulted in greater depletion of LPS, leading to an increase in the percentage loss of CAL Factor C activity. On the other hand, regardless of any fixed amount of rFC in the reaction mixture, increasing levels of LPS increased CAL Factor C activity. This indicates that excess LPS was again able to activate CAL Factor C enzyme activity. Even without purification, the crude rFC was able to effectively reduce Factor C activity in CAL by >80%, equivalent to a ratio of 1000:1 molecules of rFC to LPS (FIG. 22A, dashed line).

With increasing amounts of LPS used over a fixed amount of Biomax™-50 enriched rFC sample, the percentage loss of CAL Factor C activity was effectively maintained at >80% (FIG. 22B). For a >80% reduction in CAL Factor C activity, a ten-fold increase in the binding efficacy was observed between enriched rFC and LPS at a ratio of 100:1 (FIG. 22B, dashed line).

The Biomax™-50 rFCSN which served as the internal negative control showed little or no effect on the enzymatic activity of CAL Factor C. The rFCEE, having a lower binding affinity of LPS, displayed a markedly lower competitive effect on the enzymatic activity of native Factor C (FIG. 23).

Only micrograms of the total crude rFC were needed to remove nanograms of LPS, as reflected by ≧80% loss in CAL activity. With partial purification and concentration using Biomax™-50 membrane, the ratio of rFC to LPS for maximal LPS removal improved by ten-fold.

Interactive binding between rFC and immobilized lipid A using the BIACORE X™ sensor indicates that although background binding was attributed to rFCSN, the overall binding of partially-purified rFC to lipid A gave a net response of approximately 30% of the total immobilized lipid A. Thus, the full-length rFC has an affinity for lipid A such that 30% of lipid A is bound by the partially-purified rFC when the ratio of partially-pure rFC to lipid A is 10:1 on a mass basis. This shows that rFC has affinity for bound lipid A. rFCEE also gave a binding response but again, displayed at a lower affinity of 15% (FIG. 24). For purposes of this application, the terminology "retains lipid A binding activity" indicates an affinity of $10^{-6}$ M or lower. Preferably peptides will have a binding affinity of $10^{-7}$ M or lower.

In experiments described in reference 77, rFCES produced in Drosophila cells and purified to homogeneity shows 92% saturation of immobilized lipid A in a BIACORE X™ apparatus under conditions similar to those decribed above, except that the concentration of rFCES was 8 ng/μl. Thus, under these conditions 240 ng of rFCES binds 2.8 μg lipid A giving a ratio of about 1:12 rFCES to lipid A on a mass basis.

EXAMPLE 13 rFC Has Bacteriostatic Activity

The rFC and deletion proteins expressed in *P. pastoris* in Example 12 were examined for bacteriostatic activity in in vitro cultures.

The bacteria used for the assay were *Escherichia coli* ATCC#25922, *Salmonella typhimurium* ATCC#14028, *Pseudomonas aeruginosa* ATCC#27853, *Klebsiella pneumoniae* ATCC#13883 and *Staphylococcus aureus* ATCC#25923. A colony of each Gram-negative bacterium was inoculated into nutrient broth (Gibco, BRL) and grown at 37° C. until it reached the logarithmic phase of growth. The culture was diluted with nutrient broth to give $1-5 \times 10^5$ cells/ml. Aliquots of 2 ml culture were incubated with 1 mg rFC/ml of culture. Incubation was carried out at 37° C. At time intervals of 0, 2, 4, 6, and 24 h, the bacterial culture was vortexed to break up any agglutinated clumps. After vortexing, each culture was examined under the microscope to ensure homogeneity of bacteria. The culture was serially diluted with 0.85% saline, plated on nutrient agar (Oxoid) and incubated overnight at 37° C. for colony counting.

Crude full-length rFC and Sephadex™ G-100 enriched rFC truncates rFCEE and rFCSN did not have any inhibitory effect on the growth of the various bacteria used. However, enrichment of full-length rFC by Biomax™-50 ultrafiltration followed by chromatography through Sephadex™ G-100 yielded rFC which inhibited the growth of Gram-negative bacteria such as *E. coli, K. pneumoniae, P. aeruginosa,* and *S. typhimurium* (FIG. 25). The enriched rFC sample showed a particularly potent bacteriostatic on *K. pneumoniae*. This appears consistent with the antibacterial activity found in the cell-free hemolymph of *C. rotundicauda* (72). Further purification of rFC is expected to improve its bactericidal potential. The bacteriostatic effect was maintained at 100% for 2 h but the effect started to decline at 6 h of incubation, and was completely lost after 24 h. *S. aureus,* a Gram-positive bacterium, was not inhibited at all by rFC.

Agglutination of the bacteria was observed within 2 h of incubation with rFC. FIGS. 26A-26E show a typical agglutination reaction exemplified by *E. coli* This could be attributed to the bacteriostasis of the bacteria because interestingly, there was no agglutination observed with the *S. aureus* culture which similarly did not show any inhibited growth. Indirectly, the agglutination effect of rFC could be utilized as a rapid detection method and/or for the removal of Gram-negative bacteria from a sample.

Since LPS is required for reproduction of Gram-negative bacteria (40), it could be envisaged that rFC binds to the lipid A portion of LPS to neutralize its biological activities, causing agglutination which leads to bacteriostasis. This specific binding of rFC to LPS was confirmed by the observation that growth of Gram-positive *S. aureus,* which does not possess LPS on its outer wall, was not affected by rFC.

EXAMPLE 14 rFC Protects Actinomycin D-sensitized Mice from LPS Lethality

Actinomycin D (Sigma) was used to sensitize mice to submicrogram amounts of LPS (65,66). The protective effect of rFC on the mortality of actinomycin D-sensitized/LPS-challenged mice was studied according to protocols previously described (19,67,21). In this in vivo experiment, 500 μl aliquots containing 25 or 50 ng LPS from *E. coli* 055:B5 (Sigma) and 50 μg rFC produced as in Example 12, or saline, were preincubated at 37° C. for 60 min. The LPS-rFC or LPS-saline mix was combined 1:1 with 250 μg/ml actinomycin D immediately prior to injection. A 0.2 ml volume of this solution containing 25 μg actinomycin D, 5 or 10 ng LPS and 10 μg rFC was injected intraperitoneally into each outbred male Swiss albino (20-25 g) mouse. Groups of 10 mice were used for each replicate set of experiment. The percentage of surviving mice was determined at 72 h.

An earlier experiment determined that the 50% lethal dose of LPS on Swiss albino mice is 3.16 ng. Amounts of 5 and 10 ng of LPS were therefore used in this in vivo experiment. The protective effect of Sephadex™ G-100 enriched rFC on actinomycin D-sensitized/LPS-challenged mice is shown in FIG. 27. Recombinant Factor C was able to attenuate the toxic effect of LPS, and this resulted in the decreased mortality of the sensitized mice challenged with the rFC-LPS mix. On the other hand, rFCSN that lacks the endotoxin-binding domain did not confer any protection on the LPS-challenged mice. This observation suggests that like LALF (19,67) and human cationic antimicrobial protein CAP18 (21), rFC binds specifically to the biological moiety of LPS to neutralize its lethal effect on mice.

EXAMPLE 15

LPS Binding by rFC Produced in a Baculovirus Host-vector System

Recombinant Factor C was produced in Sf9 cells infected with a recombinant baculovirus comprising the CrFC21 cDNA encoding full-length rFC. The recombinant protein was expressed and partially purified by Biomax™ ultrafiltration and gel filtration chromatography over Sephadex™ G-100 as described in reference 76. The recombinant rFC exhibits its normal serine protease activity as shown in that reference.

The partially purified, full-length rFC was assayed for activity in binding the LPS obtained from *K. pneumoniae*, *S. minnesota*, *E. coli* and *S. typhimurium* using the BIACORE X™ system and the experimental conditions indicated in Example 12(8). The data of FIG. 29 show that the rFC binds much more strongly to the LPS from *K. pneumoniae* then to the LPS from *E. coli*.

EXAMPLE 16 rFC Produced in Baculovirus-infected Cells Induces Bacteriostasis and Protects Mice from LPS Lethality The rFC produced in the baculovirus-infected Sf9 cells described in Example 15 was assayed for its activity in inducing bacteriostasis and for protective effect in the LPS challenge experiment.

The bacteriostatic activity of the rFC from Sf9 cells was assessed in the manner described in Example 13. The data in FIG. 30 show that the bacteriostatic effect is observed and that, for *E. coli* and *K. pneumoniae*, it shows similar kinetics to that shown for the rFC obtained from yeast. The bacteriostasis induced for *S. typhimurium* and *P. aeruginosa*, on the other hand, was of much shorter duration when rFC produced in the Sf9 cells is used.

The ability of the rFC produced in recombinant baculovirus-infected Sf9 cells to protect mice from lethal LPS challenge was also tested. The experiment was conducted in the same manner as described in Example 14, except that only 10 μg of the partially purified rFC was administered. In FIG. 31, rFC-Sf9 indicates administration of recombinant rFC together with the indicated amount of LPS; wt-Sf9 indicates that supernatants from Sf9 cells harboring only wild type baculorvirus were used. Consistent with the bacteriostatic effect observed in cultured bacteria, the rFC produced in recombinant baculovirus-infected Sf9 cells was able to protect a significant proportion of the challenged mice from LPS lethality.

The invention being thus described, various modifications of the materials and methods used in the practice of the invention will be readily apparent to one of ordinary skill in the art. Such modifications are considered to be encompassed by the scope of the invention as described in the claims below.

TABLE 1

A Comparison between binding affinity of Factor C-derived sushi proteins and other LPS-binding proteins to lipid A.

| Proteins | Ligand | Association constant ($M^{-1}s^{-1}$) | Dissociation constant ($s^{-1}$) | Equilibrium constant (M) | References |
|---|---|---|---|---|---|
| Sushi-123 | Lipid A *E. coli* K12 | $4.01 \times 10^5$ | $1.48 \times 10^{-4}$ | $3.691 \times 10^{-10}$ | |
| | | $5.20 \times 10^5$ | $7.88 \times 10^{-7}$ | $1.515 \times 10^{-12}$ | |
| Sushi-1 | Lipid A *E. coli* K12 | $2.401 \times 10^4$ | $3.64\ 10^{-4}$ | $1.516 \times 10^{-10}$ | |
| Sushi-3 | Lipid A *E. coli* K12 | $1.479 \times 10^5$ | $2.031 \times 10^{-4}$ | $1.373 \times 10^{-9}$ | |
| Native LALF | Lipid A *E. coli* K12 | $3.124 \times 10^4$ | $1.154 \times 10^{-4}$ | $3.694 \times 10^{-9}$ | |
| Calionic protein 18 (CAP18) | LPS *S. minnesota* Re595 | | | $5.8 \times 10^{-10}$ | de Haas et al., 1998 |
| Bacterial/Permeability-Increasing Protein (BPI) | Lipid A *E. coli* J5 | | | $4.1 \times 10^{-9}$ | Gazzano-Santoro et al., 1992 |
| Recombinant BPI$_{23}$ | Lipid A *E. coli* J5 | | | $2.6\text{-}4.3 \times 10^{-9}$ | Gazzano-Santoro et al., 1992; 1994 |
| Recombinant BPI$_{21}$ (rBPI21) | LPS *S. minnesota* Re595 | | | $3.75 \times 10^{-9}$ | de Haas et al., 1998 |
| BPI pep85-99 (15 mer) | | | | $1.76 \times 10^{-6}$ | de Haas et al., 1998 |
| Serum amyloid P component (SAP) | LPS *S. minnesota* Re595 | | | $3.9 \times 10^{-9}$ | de Haas et al., 1998 |
| SAP pep186-200 | LPS *S. minnesota* Re595 | | | $1 \times 10^{-5}$ | de Haas et al., 1998 |
| Native LBP | LPS *S. minnesota* Re595 | | | $3.5 \times 10^{-9}$ | Tobias et al., 1995 |
| Recombinant LPS-binding protein (LBP) | Lipid A *E. coli* J5 | | | $5.8 \times 10^{-8}$ | Gazzano-Santoro et al., 1994 |
| NH-LBP (aa 1-197) | | | | $5.1 \times 10^{-8}$ | Han et al., 1994 |
| Recombinant soluble human CD14 | LPS *S. minnesota* Re595 | | | $2.9 \times 10^{-8}$ | Tobias et al., 1995 |
| Polymixin B | | | | $3.3 \times 10^{-7}$ | Vaara M., 1992 |
| Polymixin nonapeptides | | | | $1.1\text{-}1.3 \times 10^{-6}$ | Vaara and Vijanen, 1985 |
| Limulus endotoxin-binding protein-protease inhibitor | LPS *E. coli* O55:85 | | | $6 \times 10^{-6}$ | Minett et al., 1991 |

TABLE 2

Comparison of MBC$_{50}$, MBC$_{90}$, hemolytic and cytotoxic activities of Sushi and other cationic peptides on *P. aeruginosa*.

| Test peptides | MBC$_{50}$ (μg/ml) | MBC$_{90}$ (μg/ml) | Strains tested (n) | Killing rate* (min) | Hemolytic activity |
|---|---|---|---|---|---|
| S1 | ≦0.03 | ≦0.03 | 30 | 7 | 0% at 100 μg/ml |
| SΔ1 | ≦0.03 | 0.06 | 30 | 7 | 0% at 100 μg/ml |
| S3 | ≦0.03 | ≦0.03 | 30 | 7 | 5% at 100 μg/ml |
| SΔ3 | ≦0.03 | 0.25 | 30 | 7 | 35% at 100 μg/ml |
| SMAP-29 | NA | 0.38-6.4[b] | 2 | NA | 67% at 255 μg/ml[c] |
| Buforin II | 32 | 64 | 10 | 30[d] | NA |
| Cecropin I | 32 | 128 | 10 | 30[d] | NA |
| Indolicin | 64 | >128 | 10 | 60[d] | NA |
| Magainin II | 64 | NA | 10 | 60[d] | NA |
| Nisin | 128 | NA | 10 | 60[d] | NA |
| Ranalexin | >128 | NA | 10 | >60[d] | NA |

[a]Killing rate for concentration achieving MBC$_{90}$.
[b]Only MIC value was reported.
[c]Hemolysis was done on human erythrocytes. Values were converted from its MW of 3198.
[d]Time-kill kinetics were tested on *Escherichia coli*.
NA Data not available
MBC$_{50}$ Concentration of peptide required to kill 50% of the strains.
MBC$_{90}$ Concentration of peptide required to kill 90% of the strains.

TABLE 3

Indicators of LPS-binding, anti-LPS and antimicrobial activities of Factor C & peptides

| Factor C fragments & peptides | Affinity for LPS (BIAcore) K$_o$ (M) | Stoichlometry of Binding Cooperativity Hill's Co-efficient | CD + lip A | LPS-Neutralisation ENC$_{10}$ (μM) | Suppression of LPS-Induced cytokine TNF-α (50%) | Mouse Protection Assay % | Cytotoxicity (Cell lysis) % | Haemolytic Activity at 100 μg/ml peptide (hu RBC) % lysis | Anti-microbial Potency *P. aeruginosa* MBC$_{90}$ μg/ml (n/a) or MIC$_{\infty}$ |
|---|---|---|---|---|---|---|---|---|---|
| SSCrFCES | | 2.2 | | 0.069 | 8.5 nM | 90% at 2 μM (76 μg) | 20% lysis at 109 μM (4 mg/ml) | | |
| Sushi 123 | 3.7 × 10$^{-10}$ 1.5 × 10$^{-22}$ | | | | | | | | |
| Sushi 1 | 1.5 × 10$^{-10}$ | — | | — | | | | | |
| Sushi 3 | 1.4 × 10$^{-9}$ | — | | — | | | | | |
| S1 | 1.07 × 10$^{-4}$ | 2.42 | 43% α-H 57% T | 2.25 | — | 22% at 75 μg (20 nmol) | | 0 | 0.03 μg/ml (8 nM) |
| S1Δ | 6.65 × 10$^{-7}$ | 1.06 | 16% α-H 10.8% β 38.2% T | 0.875 | 53 μM | 40% at 75 μg (6.7 nmol) | 5-10% lysis at 4 mg/ml | 0 | 0.06 μg/ml (16 nM) |
| S3 | 5.85 × 10$^{-7}$ | 0.99 | 90.6% β 9.4% α-H | 1 | 94 μM | 58% at 75 μg (10 nmol) | | 5 | ≦0.03 μg/ml (8 nm) |

MBC (bracketing S1, S1Δ, S3 rows)

TABLE 3-continued

Indicators of LPS-binding, anti-LPS and antimicrobial activities of Factor C & peptides

| Factor C fragments & peptides | Affinity for LPS (BIAcore $K_o$) (M) | Stoichiometry of Binding Cooperativity Hill's Co-efficient | CD + lip A | LPS-Neutralisation $ENC_{10}$ (µM) | Suppression of LPS-Induced cytokine TNF-α (50%) | Mouse Protection Assay % | Cytotoxicity (Cell lysis) % | Haemolytic Activity at 100 µg/ml peptide (hu RBC) % lysis | Anti-microbial Potency *P. aeruginosa* $MBC_{90}$ µg/ml (n/a) or $MIC_{oo}$ |
|---|---|---|---|---|---|---|---|---|---|
| S3Δ | $6.61 \times 10^{-2}$ | 0.91 | 46.5% α-H 52.5% T | 0.625 | 40 µM | 100% at 75 µg (19 nmol) | 25-30% lysis at 4 mg/ml | 35 | 0.25 µg/ml (63 nm) |
| S4 | $1.02 \times 10^{-5}$ | 0.3 | 100% Random | 0.01 | 20 µM | — | 3.8 µM | 20% | ≦0.01 µg/ml } MIC |
| S5 | $6.31 \times 10^{-4}$ | 2.1 | 100% R Random | >0.25 | >200 µM | — | 33 µM | 0% | ≦0.01 µg/ml |
| S6-vg1 | $1.39 \times 10^{-5}$ | 1.0 | 3.3% α Helical | >0.25 | 37.5 µM | — | 26 µM | 5% | ≦0.01 µg/ml |
| S7-vg2 | $2.71 \times 10^{-8}$ | 1.1 | 100% R Random | >0.25 | 30 µM | — | 400 µM $BC_{50}$ | 5% | ≦0.01 µg/ml } MBC |
| S8-vg3 | $2.5 \times 10^{-5}$ | 0.9 | 100% α Helical | 0.03 | 20 µM | — | 22 µM | 100% | ≦0.01 µg/ml |
| S9-vg4 | $1.73 \times 10^{-5}$ | 1.0 | 100% α Helical | >0.25 | 25 µM | — | 35 µM | 75% | ≦0.01 µg/ml |

REFERENCES

Articles of the patent and scientific periodical literature have been cited throughout this document. Each such article is hereby incorporated in its entirety by reference by such citation.

1. Karima R., Matsumoto, S., Higashi, H. and Matsushima, K. (1999) The molecular pathogenesis of endotoxic shock and organ failure. Mol. Med. Today 5(3) 123-132.
2. Kreutz, M., Ackermann, U., Hauschildt, S., Krause, S. W., Riedel, D., Bessler, W. and Andreesen, R. (1997) A comparative analysis of cytokine production and tolerance induction by bacterial lipopeptides, lipopolysaccharides and *Staphyloccous aureus* in human monocytes. Immunology 92(3), 396-401.
3. Tracey, K. J. and Lowry, S. F. (1990) The role of cytokine mediators in septic shock. Adv. Surg. 23, 21-56.
4. Zahringer, U., Lindner, B. and Rietschel, E. T. (1994) Molecular structure of lipid A, the endotoxic center of bacterial lipopolysaccharides. Adv. Carbohydr. Chem. Biochem. 50, 211-76.
5. Armstrong, P. B. and Rickles, F. R. (1982) Endotoxin-induced degranulation of the *Limulus* amebocyte. Exp. Cell Res. 140, 15-24.
6. Levin, J., Tomasulo, P. A. and Oser, R. S. (1970) Detection of endotoxin in human blood and demonstration of an inhibitor. J. Lab. Clin. Med. 75, 903-911.
7. Novitsky, T. J. (1994) *Limulus* amoebocyte lysate (LAL) detection of endotoxin in human blood. J. Endotoxin Res. 1, 253-263.
8. Muta, T. and Iwanaga, S. (1996) Clotting and immune defense in Limulidae. Prog. Mol. Subcell. Biol. 15, 154-189.
9. Nakao, A., Tasul, M., Shen, S. and Takagi, H. (1995) Heparin effects on superoxide production by neutrophils. Eur. Surg. Res. 27(4), 216-221.
10. Ding, J. L., Navas, M. A. A. and Ho, B. (1925) Molecular cloning and sequence analysis of Factor C cDNA from the Singapore horseshoe crab, *Carcinoscorpius rotundicauda*. Mol. Marine Biol. Biotech. 4(1), 90-103.
11. Roopashree, S. D., Chai, C., Ho, B. and Ding, J. L. (1995) Expression of *Carcinoscorpius rotundicauda* Factor C cDNA. Biochem. Mol. Biol. Intl. 35(4), 841-849.
12. Roopashree, S. D., Ho, B. and Ding, J. L. (1996) Expression of *Carcinoscorpius rotundicauda* Factor C in *Pichia pastoris*. Mol. Marine Biol. Biotech. 5(3), 334-343.
13. Pui, A. W. M., Ho, B. and Ding, J. L. (1997) Yeast recombinant Factor C from horseshoe crab binds endotoxin and causes bacterostasis. J. Endotoxin Res. 4(6), 391-400.
14. Clare, J. J. et al. And Henwood, C. A. (1991) Production of mouse epidermal growth factor in yeast: high level secretion using *Pichia pastoris* strains containing multiple gene copies. Gene 105, 205-212.
15. Hussein, A. S., Chacon, M. R., Smith, A. M., Tosado-Acevedo, R., Selkirk, M. E. (1999) Cloning, expression, and properties of a nonneuronal secreted acetylcholinesterase from the parasitic nematode *Nippostrongylus brasiliensis*. J Biol. Chem. 274(14), 9312-9319.
16. Muta, T., Miyata, T., Misumi, Y., Tokunaga, F., Nakamura, T., Toh, Y., Ikehara, Y. and Iwanaga, S. (1991) *Limulus* factor C. An endotoxin-sensitive serine protease zymogen with a mosaic structure of complement-like, epidermal growth factor-like, and lectin-like domains. J. Biol. Chem. 266, 6554-6561.
17. Righetti, P. G. and Giaffreda, E. (1994) Immobilized buffers for isoelectric focusing: from gradient gels to membranes. Electrophoresis 15(8-9), 1040-1043.
18. Marra, M. N., Wilde, C. G., Griffith, I. E., Snable, J. L. and Scott R. W. (1990) Bactericidal/permeability-increasing protein has endotoxin-neutralizing activity. J. Immunol. 144, 662-666.
19. Warren H. S. Glennon, M. L., Wainwright, N., Amato, S. F., Black, K. M., Kirsch, S. J., Riveau, G. R., Whyte, R. I., Zapol, W. M. and Novitsky, T. J. (1992) Binding and neutralization of endotoxin by *Limulus* Antilipopolysaccharide Factor. Infect. Immun. 60(6), 2506-2513.
20. Appelemelk, B. J., An, Y. Q., Geerts, M. Thijs, B. G., DeBoer, H. A., MacLaren, D. M., DeGraaff, J. and Nuijens, J. H. (1994) Lactoferrin is a lipid A-binding protein. Infect. Immun. 62, 2628-2632.
21. Larrick, J. W., Hirata, M., Balint, R. F., Lee, J., Zhong, J. and Wright, S. C. (1995) Human CAP18: a novel antimicrobial lipopolysaccharide-binding protein. Infect. Immun. 63(4), 1291-1297.
22. O'Riordan, J. F., Goldstick, T. K., Ditzel, J. and Ernest, J. T. (1983) Characterization of oxygen-hemoglobin equilibrium curves using nonlinear regression of the Hill equation: parameter values for normal human adults. Adv Exp Med Biol 159, 435-444.
23. Hill, A. V. (1910) The combinations of haemoglobin with oxygen and with carbon monoxide. I. J. Physiol. (Lond.) 40, 4-8.
24. Zhang, G. H., Mann, D. M. and Tsai, C. M. (1999) Neutralization of endotoxin in vitro and in vivo by a human lactoferrin-derived peptide. Infect. Immun. 67(3), 1353-1358.
25. Tsuchiya, S., Kobayashi, Y., Goto, Y., Okumura, H., Nakae, S., Konno, T. and Tada, K. (1982) Induction of maturation in cultured human monocytic leukemia cells by a phorbol diester. Cancer Res. 42(4), 1530-1536.
26. Ried, C., Wahl, C., Miethke, T., Wellnhofer, G., Landgraft, C., Schneider-Mergener, J. and Hoess, A. (1996) High affinity endotoxin-binding and neutralizing peptides based on the crystal structure of recombinant *Limulus* Antilipopolysaccharide Factor. J. Biol. Chem. 45, 28120-28127.
27. Cory, A. H., Owen, T. C., Barltrop, J. A. and Cory, J. G. (1991) Use of an aqueous soluble tetrazolium/formazan assay for cell growth assays in culture. Cancer Commun. 3, 207-212.
28. Riss, T. L. and Moravec, R. A. (1992) Comparison of MTT, XTT, and a novel tetrazolium compound MTS for in vitro proliferation and chemosensitivity assays. Mol. Biol. Cell 3 (Suppl.), 184a.
29. Lehmann, V., Freudenberg, M. A. and Galanos, C. (1987) Lethal toxicity of lipopolysaccharide and tumor necrosis factor in normal and D-galactosamine-treated mice. J. Exp. Med. 165, 657-663.
30. Laub, P. B. and Gallo, J. M. (1996) NCOMP—a windows-based computer program for noncompartmental analysis of pharmacokinetic data. J Pharm. Sci. 85(4), 393-5.
31. Galanos, C., Freudenberg, M. A. and Reutter, W. (1979) Galactosamine-induced sensitization to the lethal effects of endotoxin. Proc. Natl. Acad. Sci. USA 76, 5939-5943.
32. Kaplan, E. L. and Meier, P. (1958) Nonparametric estimation from imcomplete observations. J. Am. Stat. Assoc. 53, 457-481.
33. Andrea, G., Cirioni, O., Barchiesi, F, Prete, M S D and Scalise G. (1999) Antimicrobial activity of polycationic peptides. Peptides. 20: 1265-1273.
34. Agerberth, B., Gunne, H., Odeberg, I., Kogner, P., Boman, H G and Gudmundsson, G (1995). FALL-39, a putative human peptide antibiotic is cysteine-free and expressed in bone marrow and testis. Proc. Natl. Acad. Sci. USA. 92: 195-199.
35. Barbara, S., Benincasa, M., Risso, A, Zanetti, M and Gennaro, R. (1999). SMAP-29: a potent antibacterial and antifungal peptide from sheep leukocytes. FEBS Letts. 463: 58-62.
36. Teshima, T., Ueky, Y., Nakai, T. and Shiba, T. (1986). Structure determination of lepidopteran, self-defense substance produced by silkworm. Tetrahedron. 42: 829-834.
37. Sawa, T., Kurahashi, K, Ohara, M., Gropper, M A., Doshi, V., Larrick, J W. And Wiener-Kronish, J P. (1998). Evaluation of antimicrobial and lipopolysaccharide-netralising effects of a synthetic CAP-18 fragment against *Pseudomonas aeruginosa* in a mouse model. Antimicrob. Agents Chemother. 42: 3269-3275.
38. Bone, R C. (1991). The pathogenesis of sepsis. Ann. Intern. Med. 115: 457-460.
39. Parrillo, J E., Parker, M M, Nathanson, C., Cunmnion, A F., Ognibene F P. (1990). Septic shock in humans. Advances in the understanding of pathjogenesis, cardiovascular, dysfunction and therapy. Ann. Intern. Med. 113: 227-237.
40. Rietschel E. T. et al., Sci Am Aug. 1992; 26-33.
41. Tobias P. S. et al., J Exp Med 1986; 164: 777-793.
42. Marra M. N. et al., J Immunol 1992; 148: 532-537.
43. Tobias P. S. et al., J Biol Chem 1989; 264: 10867-10871.
44. Elsbach P. et al., Curr Opin Immunol 1993; 5: 103-107.
45. Rogy M. A. et al., J Clin Immun 1994; 14: 120-133.
46. Tanaka S. et al., Biochem Biophys Res Commun 1982; 105: 717-723.
47. Morita T. S. et al., J Biochem 1985; 97: 1611-1620.
48. Aketagawa J. et al., J Biol Chem 1986; 261: 7357-7365.
49. Muta T. et al., J Biochem 1987; 101: 1321-1330.
50. Alpert G. et al., J Infect Dis 1992; 165: 494-500.
51. Fletcher M. A. et al., J Surg Res 1993; 55: 147-154.
52. Garcia C. et al., Crit Care Med 1994; 22: 1211-1218.
53. Nakamura T. et al., J Biol Chem 1988; 263: 16709-16713.
54. Miyata T. et al., J Biochem 1989; 106: 663-668.
55. Saito T. et al., J Biochem 1995; 117: 1131-1137.
56. Levin J. et al., Bull John Hopkins Hosp 1964; 115: 265-274.
57. Nakamura T. et al., Eur J Biochem 1986; 154: 511-521.
58. Tokunaga F. et al., Eur J Biochem 1987; 167: 405-416.
59. Ho B., Microbios Lett 1983; 24: 81-84.
60. Roopashree S. D. et al., Biochem Mol Biol Intl 1995; 35: 841-849.
61. Ding J. L. et al., J Endotoxin Res 1997; 4: 33-43.
62. Bradford M. M. et al., Anal Biochem 1976; 72: 248-254.
63. Laemmli U. K. et al., Nature 1970; 227: 680-684.
64. Iwanaga S. et al., Japan Patent Agency Official Bulletin 1980; 557-108018.
65. Pieroni R. E. et al., Proc Soc Exp Biol Med 1971; 133: 790-794.
66. Brown D. E. et al., J Infect Dis 1982; 146: 746-750.
67. Kloczewiak M. et al., J Infect Dis 1994; 170; 1490-1497.
68. Nakamura T. et al., J Biochem 1988; 103: 370-374.
69. Sandri M. et al., Anal Biochem 1993; 213: 34-39.
70. Tsai C. M. et al., Anal Biochem 1982; 119: 115-119.
71. Miura Y. et al., J Biochem 1992; 112: 476-481.
72. Yeo D. S. A. et al., Microbios 1993; 73: 45-58.
73. U.S. Pat. No. 5,716,834
74. U.S. Pat. No. 5,712,144
75. U.S. patent application Ser. No. 08/877,620
76. U.S. patent application Ser. No. 09/081,767
77. U.S. Patent Application No. 60/106,426
78. U.S. patent application Ser. No. 09/201,786
79. "Remington, the Science and Practice of Pharmacy", 19$^{th}$ Edition, c. 1995 by the Philadelphia College of Pharmacy and Science.

What is claimed is:

1. A method for purifying a liquid sample by removal of endotoxin, the method comprising immobilizing an isolated polypeptide on an insoluble matrix, contacting said sample with the immobilized polypeptide, and separating said sample from said immobilized polypeptide, wherein the polypeptide comprises a lipopolysaccharide binding domain comprising a peptide selected from the group consisting of: sushi-1Δ peptide (SEQ ID NO:6); sushi-3Δ peptide (SEQ ID NO:8); sushi-4 peptide (SEQ ID NO:9); sushi-5 peptide (SEQ ID NO:10); sushi-6-vg1 peptide (SEQ ID NO:11); sushi-7-vg2 peptide (SEQ ID NO:12); sushi-8-vg3 peptide (SEQ ID NO:13); and sushi-9-vg4 peptide (SEQ ID NO:14), thereby removing endotoxin from the sample.

2. The method according to claim 1 wherein the polypeptide further comprises a secretory signal sequence of a vitellogenin protein.

3. The method according to claim 1 wherein the polypeptide further comprises a reporter protein or an affinity tag.

4. The method according to claim 3 wherein the reporter protein is selected from the group consisting of green fluorescent protein (GFP), alkaline phosphatase, a peroxidase, and a luciferase.

5. The method according to claim 3 wherein the affinity tag is polyhistidine or biotin.

6. The method according to claim 1 wherein the polypeptide is substantially free of serine protease activity.

7. The method according to claim 6 wherein the polypeptide further comprises a secretory signal sequence of a vitellogenin protein.

8. The method according to claim 6 wherein the polypeptide further comprises a reporter protein or an affinity tag.

9. The method according to claim 1 wherein the polypeptide comprises sushi-1Δ peptide (SEQ ID NO:6).

10. The method according to claim 1 wherein the polypeptide comprises sushi-3Δ peptide (SEQ ID NO:8).

11. The method according to claim 1 wherein the sample is contacted with the immobilized polypeptide at basic pH or at low ionic strength conditions defined by 800 mM NaCl or less, or both.

12. The method according to claim 1 wherein the sample is separated from the immobilized polypeptide by column chromatography.

13. The method according to claim 1 wherein the sample is separated from the immobilized polypeptide by centrifugation.

14. The method according to claim 1 wherein the polypeptide is immobilized via EDC [1-ethyl-3-(3-dimethylaminopropyl) carbodiimide]/DADPA (diaminodipropylamine).

15. The method according to claim 1 wherein the insoluble matrix is an activated resin.

16. The method according to claim 15 wherein the resin is agarose.

17. A method for purifying a liquid sample by removal of endotoxin, the method comprising immobilizing an isolated polypeptide on an insoluble matrix, contacting said sample with the immobilized polypeptide, and separating said sample from said immobilized polypeptide, wherein the polypeptide comprises sushi-1 peptide (SEQ ID NO:5) or sushi-3 peptide (SEQ ID NO:7) or sushi-1 (SEQ ID NO:5) and sushi-3 (SEQ ID NO:7) peptides from the LPS-binding domain of Factor C, operably linked to a secretory signal sequence from a vitellogenin protein.

18. The method according to claim 17 wherein the polypeptide comprises the sushi-1 domain or sushi-3 domain of Factor C, operably linked to a secretory signal sequence from a vitellogenin protein.

19. The method according to claim 18 wherein the polypeptide is purified secretory signal sequence *Carcinoscorpius rotundicauda* Factor C EcoRI-SalI (SSCrFCLS).

20. The method according to claim 18 wherein the polypeptide further comprises a reporter protein or an affinity tag.

21. The method according to claim 20 wherein the reporter protein is selected from the group consisting of green fluorescent protein (GFP), alkaline phosphatase, a peroxidase, and a luciferase.

22. The method according to claim 20 wherein the affinity tag is polyhistidine or biotin.

23. The method according to claim 21 wherein the polypeptide is secretory signal sequence *Carcinoscorpius rotundicauda* Factor *C-sushi*-1-GFP (SSCrFC-sushi-1-GFP), secretory signal sequence *Carcinoscorpius rotundicauda* Factor C-sushi-3-GFP (SSCrFC-sushi-3-GFP), or secretory signal sequence *Carcinoscorpius rotundicauda* Factor C-sushi-1,2,3-GFP (S SCrFC-sushi-1,2,3-GFP).

24. The method according to claim 18 wherein the sample is contacted with the immobilized polypeptide at basic pH or at low ionic strength conditions defined by 800 mM NaCl or less, or both.

25. The method according to claim 18 wherein the sample is separated from the immobilized polypeptide by column chromatography.

26. The method according to claim 18 wherein the sample is separated from the immobilized polypeptide by centrifugation.

27. The method according to claim 18 wherein the polypeptide is immobilized via EDC [1-ethyl-3-(3-dimethylaminopropyl) carbodiimide]/DADPA (diaminodipropylamine).

28. The method according to claim 18 wherein the insoluble matrix is an activated resin.

29. The method according to claim 28 wherein the resin is agarose.

30. The method according to claim 17 wherein the sample is contacted with the immobilized polypeptide at basic pH or at low ionic strength conditions defined by 800 mM NaCl or less, or both.

31. The method according to claim 17 wherein the sample is separated from the immobilized polypeptide by column chromatography.

32. The method according to claim 17 wherein the sample is separated from the immobilized polypeptide by centrifugation.

33. The method according to claim 17 wherein the polypeptide is immobilized via EDC [1-ethyl-3-(3-dimethylaminopropyl) carbodiimide]/DADPA (diaminodipropylamine).

34. The method according to claim 17 wherein the insoluble matrix is an activated resin.

35. The method according to claim 34 wherein the resin is agarose.

36. A method for purifying a liquid sample by removal of endotoxin, the method comprising immobilizing an isolated polypeptide on an insoluble matrix, contacting said sample with the immobilized polypeptide, and separating said sample from said immobilized polypeptide, wherein the polypeptide consists of sushi-1 peptide (SEQ ID NO:5) or sushi-3 peptide (SEQ ID NO:7) from the LPS-binding domain of Factor C.

* * * * *

UNITED STATES PATENT AND TRADEMARK OFFICE
CERTIFICATE OF CORRECTION

| | | |
|---|---|---|
| PATENT NO. | : 7,297,551 B2 | Page 1 of 1 |
| APPLICATION NO. | : 10/638125 | |
| DATED | : November 20, 2007 | |
| INVENTOR(S) | : Ding et al. | |

It is certified that error appears in the above-identified patent and that said Letters Patent is hereby corrected as shown below:

At Column 9, lines 51-52 "typical in the art, but is preferably made in a eukaryotic host cell. Production" should read -- typical in the art. Production --.

At Column 12, line 15, insert the following heading: -- (a) Purification of SSCrFCES using a TALON column --.

At Column 63, line 52 (in claim 19), "(SSCrFCLS)" should read -- (SSCrFCES) --.

Signed and Sealed this

Nineteenth Day of August, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 4182
<212> TYPE: DNA
<213> ORGANISM: Carcinoscorpius rotundicauda
<220> FEATURE:
<221> NAME/KEY: CDS
<222> LOCATION: (569)..(3817)

<400> SEQUENCE: 1

```
gtatttaatg tctcaacggt aaaggtttca ttgtagctaa tatttaactt cctccctgtg      60
ccccaaatcg cgagtatgac gtcagttaag acttcgtatt ttaagagtta aacacgagcc     120
ttaaagagcg atatttttt tgttaaacac ttccaactta atacaattgg caaactttca     180
aaaataaagt ggaaaaggag gtaaaaaaga tgaaaaaaat tcgcatacaa tagaatacaa     240
taaaatgtgt tgtctttact gtcaacactt actgttcgtt cggtcacagc tgtgaatcgg     300
ggtgacttta tgtttgtagt ggtcttaaaa acgggtactt ggttgttttg aaaattttaa     360
aacctacata tgattctcct aaaattttgt ttataaatta gcaccatttg cgacctaaat     420
cttttttgta gtcttaagtt tagttgacat aaaaacaaaa tttgtaacaa cacacggtat     480
aaactaaata gcttcagatg ggtcgtatga caaggaaact tttaaataat tatgaaagtt     540
tttttaaaat ttgactaagg tttagatt atg tgg gtg aca tgc ttc gac acg       592
                                Met Trp Val Thr Cys Phe Asp Thr
                                  1               5 ttt ctt ttt gtt tgt gaa agt tca gtt ttc tgt ttg ttg tgt gtg tgg       640
Phe Leu Phe Val Cys Glu Ser Ser Val Phe Cys Leu Leu Cys Val Trp
       10                  15                  20 agg ttt ggt ttc tgt agg tgg cgt gtt ttc tac agt ttt cca ttc gtt       688
Arg Phe Gly Phe Cys Arg Trp Arg Val Phe Tyr Ser Phe Pro Phe Val
 25                  30                  35                  40 aag tca aca gtt gtt tta tta cag tgt tac cat tac tct ctc cac aat       736
Lys Ser Thr Val Val Leu Leu Gln Cys Tyr His Tyr Ser Leu His Asn
                 45                  50                  55 acc tca aag ttc tac tct gtg aat cct gac aag cca gag tac att ctt       784
Thr Ser Lys Phe Tyr Ser Val Asn Pro Asp Lys Pro Glu Tyr Ile Leu
             60                  65                  70 tca ggt tta gtt cta ggg cta cta gcc caa aaa atg cgc cca gtt cag       832
Ser Gly Leu Val Leu Gly Leu Leu Ala Gln Lys Met Arg Pro Val Gln
         75                  80                  85 tcc aaa gga gta gat cta ggc ttg tgt gat gaa acg agg ttc gag tgt       880
Ser Lys Gly Val Asp Leu Gly Leu Cys Asp Glu Thr Arg Phe Glu Cys
     90                  95                 100 aag tgt ggc gat cca ggc tat gtg ttc aac att cca gtg aaa caa tgt       928
Lys Cys Gly Asp Pro Gly Tyr Val Phe Asn Ile Pro Val Lys Gln Cys
105                 110                 115                 120 aca tac ttt tat cga tgg agg ccg tat tgt aaa cca tgt gat gac ctg       976
Thr Tyr Phe Tyr Arg Trp Arg Pro Tyr Cys Lys Pro Cys Asp Asp Leu
                125                 130                 135 gag gct aag gat att tgt cca aag tac aaa cga tgt caa gag tgt aag      1024
Glu Ala Lys Asp Ile Cys Pro Lys Tyr Lys Arg Cys Gln Glu Cys Lys
            140                 145                 150 gct ggt ctt gat agt tgt gtt act tgt cca cct aac aaa tat ggt act      1072
Ala Gly Leu Asp Ser Cys Val Thr Cys Pro Pro Asn Lys Tyr Gly Thr
        155                 160                 165 tgg tgt agc ggt gaa tgt cag tgt aag aat gga ggt atc tgt gac cag      1120
Trp Cys Ser Gly Glu Cys Gln Cys Lys Asn Gly Gly Ile Cys Asp Gln
```

```
                    170                 175                 180
agg aca gga gct tgt gca tgt cgt gac aga tat gaa ggg gtg cac tgt    1168
Arg Thr Gly Ala Cys Ala Cys Arg Asp Arg Tyr Glu Gly Val His Cys
185                 190                 195                 200 gaa att ctc aaa ggt tgt cct ctt ctt cca tcg gat tct cag gtt cag    1216
Glu Ile Leu Lys Gly Cys Pro Leu Leu Pro Ser Asp Ser Gln Val Gln
                205                 210                 215 gaa gtc aga aat cca cca gat aat ccc caa act att gac tac agc tgt    1264
Glu Val Arg Asn Pro Pro Asp Asn Pro Gln Thr Ile Asp Tyr Ser Cys
220                 225                 230 tca cca ggg ttc aag ctt aag ggt atg gca cga att agc tgt ctc cca    1312
Ser Pro Gly Phe Lys Leu Lys Gly Met Ala Arg Ile Ser Cys Leu Pro
        235                 240                 245 aat gga cag tgg agt aac ttt cca ccc aaa tgt att cga gaa tgt gcc    1360
Asn Gly Gln Trp Ser Asn Phe Pro Pro Lys Cys Ile Arg Glu Cys Ala
250                 255                 260 atg gtt tca tct cca gaa cat ggg aaa gtg aat gct ctt agt ggt gat    1408
Met Val Ser Ser Pro Glu His Gly Lys Val Asn Ala Leu Ser Gly Asp
265                 270                 275                 280 atg ata gaa ggg gct act tta cgg ttc tca tgt gat agt ccc tac tac    1456
Met Ile Glu Gly Ala Thr Leu Arg Phe Ser Cys Asp Ser Pro Tyr Tyr
                285                 290                 295 ttg att ggt caa gaa aca tta acc tgt cag ggt aat ggt cag tgg aat    1504
Leu Ile Gly Gln Glu Thr Leu Thr Cys Gln Gly Asn Gly Gln Trp Asn
                300                 305                 310 gga cag ata cca caa tgt aag aac tta gtc ttc tgt cct gac ctg gat    1552
Gly Gln Ile Pro Gln Cys Lys Asn Leu Val Phe Cys Pro Asp Leu Asp
        315                 320                 325 cct gta aac cat gct gaa cac aag gtt aaa att ggt gtg gaa caa aaa    1600
Pro Val Asn His Ala Glu His Lys Val Lys Ile Gly Val Glu Gln Lys
330                 335                 340 tat ggt cag ttt cct caa ggc act gaa gtg acc tat acg tgt tcg ggt    1648
Tyr Gly Gln Phe Pro Gln Gly Thr Glu Val Thr Tyr Thr Cys Ser Gly
345                 350                 355                 360 aac tac ttc ttg atg ggt ttt gac acc tta aaa tgt aac cct gat ggg    1696
Asn Tyr Phe Leu Met Gly Phe Asp Thr Leu Lys Cys Asn Pro Asp Gly
                365                 370                 375 tct tgg tca gga tca cag cca tcc tgt gtt aaa gtg gca gac aga gag    1744
Ser Trp Ser Gly Ser Gln Pro Ser Cys Val Lys Val Ala Asp Arg Glu
        380                 385                 390 gtc gac tgt gac agt aaa gct gta gac ttc ttg gat gat gtt ggt gaa    1792
Val Asp Cys Asp Ser Lys Ala Val Asp Phe Leu Asp Asp Val Gly Glu
                395                 400                 405 cct gtc agg atc cac tgt cct gct ggc tgt tct ttg aca gct ggt act    1840
Pro Val Arg Ile His Cys Pro Ala Gly Cys Ser Leu Thr Ala Gly Thr
410                 415                 420 gtg tgg ggt aca gcc ata tac cat gaa ctt tca tca gtg tgt cgt gca    1888
Val Trp Gly Thr Ala Ile Tyr His Glu Leu Ser Ser Val Cys Arg Ala
425                 430                 435                 440 gcc atc cat gct ggc aag ctt cca aac tct gga gga gcg gtg cat gtt    1936
Ala Ile His Ala Gly Lys Leu Pro Asn Ser Gly Gly Ala Val His Val
                445                 450                 455 gtg aac aat ggc ccc tac tcg gac ttt ctg ggt agt gac ctg aat ggg    1984
Val Asn Asn Gly Pro Tyr Ser Asp Phe Leu Gly Ser Asp Leu Asn Gly
                460                 465                 470 ata aaa tcc gaa gag ttg aag tct ctt gcc cgg agt ttc cga ttc gat    2032
Ile Lys Ser Glu Glu Leu Lys Ser Leu Ala Arg Ser Phe Arg Phe Asp
        475                 480                 485 tat gtc agt tcc tcc aca gca ggt aaa tca gga tgt cct gat gga tgg    2080
```

```
                    Tyr Val Ser Ser Ser Thr Ala Gly Lys Ser Gly Cys Pro Asp Gly Trp
                        490                 495                 500 ttt gag gta gac gag aac tgt gtg tac gtt aca tca aaa cag aga gcc        2128
Phe Glu Val Asp Glu Asn Cys Val Tyr Val Thr Ser Lys Gln Arg Ala
505                 510                 515                 520 tgg gaa aga gct caa ggt gtg tgt acc aat atg gct gct cgt ctt gct        2176
Trp Glu Arg Ala Gln Gly Val Cys Thr Asn Met Ala Ala Arg Leu Ala
                525                 530                 535 gtg ctg gac aaa gat gta att cca aat tca ttg act gag act cta cga        2224
Val Leu Asp Lys Asp Val Ile Pro Asn Ser Leu Thr Glu Thr Leu Arg
            540                 545                 550 ggg aaa ggg tta aca acc acg tgg ata gga ttg cac aga cta gat gct        2272
Gly Lys Gly Leu Thr Thr Thr Trp Ile Gly Leu His Arg Leu Asp Ala
        555                 560                 565 gag aag ccc ttt att tgg gag tta atg gat cgt agt aat gtg gtt ctg        2320
Glu Lys Pro Phe Ile Trp Glu Leu Met Asp Arg Ser Asn Val Val Leu
    570                 575                 580 aat gat aac cta aca ttc tgg gcc tct ggc gaa cct gga aat gaa act        2368
Asn Asp Asn Leu Thr Phe Trp Ala Ser Gly Glu Pro Gly Asn Glu Thr
585                 590                 595                 600 aac tgt gta tat atg gac atc caa gat cag ttg cag tct gtg tgg aaa        2416
Asn Cys Val Tyr Met Asp Ile Gln Asp Gln Leu Gln Ser Val Trp Lys
                605                 610                 615 acc aag tca tgt ttt cag ccc tca agt ttt gct tgc atg atg gat ctg        2464
Thr Lys Ser Cys Phe Gln Pro Ser Ser Phe Ala Cys Met Met Asp Leu
                620                 625                 630 tca gac aga aat aaa gcc aaa tgc gat gat cct gga tca ctg gaa aat        2512
Ser Asp Arg Asn Lys Ala Lys Cys Asp Asp Pro Gly Ser Leu Glu Asn
            635                 640                 645 gga cac gcc aca ctt cat gga caa agt att gat ggg ttc tat gct ggt        2560
Gly His Ala Thr Leu His Gly Gln Ser Ile Asp Gly Phe Tyr Ala Gly
        650                 655                 660 tct tct ata agg tac agc tgt gag gtt ctc cac tac ctc agt gga act        2608
Ser Ser Ile Arg Tyr Ser Cys Glu Val Leu His Tyr Leu Ser Gly Thr
665                 670                 675                 680 gaa acc gta act tgt aca aca aat ggc aca tgg agt gct cct aaa cct        2656
Glu Thr Val Thr Cys Thr Thr Asn Gly Thr Trp Ser Ala Pro Lys Pro
                685                 690                 695 cga tgt atc aaa gtc atc acc tgc caa aac ccc cct gta cca tca tat        2704
Arg Cys Ile Lys Val Ile Thr Cys Gln Asn Pro Pro Val Pro Ser Tyr
                700                 705                 710 ggt tct gtg gaa atc aaa ccc cca agt cgg aca aac tcg ata agt cgt        2752
Gly Ser Val Glu Ile Lys Pro Pro Ser Arg Thr Asn Ser Ile Ser Arg
            715                 720                 725 gtt ggg tca cct ttc ttg agg ttg cca cgg tta ccc ctc cca tta gcc        2800
Val Gly Ser Pro Phe Leu Arg Leu Pro Arg Leu Pro Leu Pro Leu Ala
        730                 735                 740 aga gca gcc aaa cct cct cca aaa cct aga tcc tca caa ccc tct act        2848
Arg Ala Ala Lys Pro Pro Pro Lys Pro Arg Ser Ser Gln Pro Ser Thr
745                 750                 755                 760 gtg gac ttg gct tct aaa gtt aaa cta cct gaa ggt cat tac cgg gta        2896
Val Asp Leu Ala Ser Lys Val Lys Leu Pro Glu Gly His Tyr Arg Val
                765                 770                 775 ggg tct cga gcc att tac acg tgc gag tcg aga tac tac gaa cta ctt        2944
Gly Ser Arg Ala Ile Tyr Thr Cys Glu Ser Arg Tyr Tyr Glu Leu Leu
                780                 785                 790 gga tct caa ggc aga aga tgt gac tct aat gga aac tgg agt ggt cgg        2992
Gly Ser Gln Gly Arg Arg Cys Asp Ser Asn Gly Asn Trp Ser Gly Arg
            795                 800                 805
```

| | |
|---|---|
| cca gcg agc tgt att cca gtt tgt gga cgg tca gac tct cct cgt tct<br>Pro Ala Ser Cys Ile Pro Val Cys Gly Arg Ser Asp Ser Pro Arg Ser<br>810                          815                         820 | 3040 |
| cct ttt atc tgg aat ggg aat tct aca gaa ata ggt cag tgg ccg tgg<br>Pro Phe Ile Trp Asn Gly Asn Ser Thr Glu Ile Gly Gln Trp Pro Trp<br>825                          830                         835                     840 | 3088 |
| cag gca gga atc tct aga tgg ctt gca gac cac aat atg tgg ttt ctc<br>Gln Ala Gly Ile Ser Arg Trp Leu Ala Asp His Asn Met Trp Phe Leu<br>                      845                         850                         855 | 3136 |
| cag tgt gga gga tct cta ttg aat gag aaa tgg atc gtc act gct gcc<br>Gln Cys Gly Gly Ser Leu Leu Asn Glu Lys Trp Ile Val Thr Ala Ala<br>                      860                         865                         870 | 3184 |
| cac tgt gtc acc tac tct gct act gct gag att att gac ccc aat cag<br>His Cys Val Thr Tyr Ser Ala Thr Ala Glu Ile Ile Asp Pro Asn Gln<br>                      875                         880                         885 | 3232 |
| ttt aaa atg tat ctg ggc aag tac tac cgt gat gac agt aga gac gat<br>Phe Lys Met Tyr Leu Gly Lys Tyr Tyr Arg Asp Asp Ser Arg Asp Asp<br>890                          895                         900 | 3280 |
| gac tat gta caa gta aga gag gct ctt gag atc cac gtg aat cct aac<br>Asp Tyr Val Gln Val Arg Glu Ala Leu Glu Ile His Val Asn Pro Asn<br>905                          910                         915                     920 | 3328 |
| tac gac ccc ggc aat ctc aac ttt gac ata gcc cta att caa ctg aaa<br>Tyr Asp Pro Gly Asn Leu Asn Phe Asp Ile Ala Leu Ile Gln Leu Lys<br>                      925                         930                         935 | 3376 |
| act cct gtt act ttg aca aca cga gtc caa cca atc tgt ctg cct act<br>Thr Pro Val Thr Leu Thr Thr Arg Val Gln Pro Ile Cys Leu Pro Thr<br>                      940                         945                         950 | 3424 |
| gac atc aca aca aga gaa cac ttg aag gag gga aca tta gca gtg gtg<br>Asp Ile Thr Thr Arg Glu His Leu Lys Glu Gly Thr Leu Ala Val Val<br>                      955                         960                         965 | 3472 |
| aca ggt tgg ggt ttg aat gaa aac aac acc tat tca gag acg att caa<br>Thr Gly Trp Gly Leu Asn Glu Asn Asn Thr Tyr Ser Glu Thr Ile Gln<br>970                          975                         980 | 3520 |
| caa gct gtg cta cct gtt gtt gca gcc agc acc tgt gaa gag ggg tac<br>Gln Ala Val Leu Pro Val Val Ala Ala Ser Thr Cys Glu Glu Gly Tyr<br>985                          990                         995                    1000 | 3568 |
| aag gaa gca gac tta cca ctg aca gta aca gag aac atg ttc tgt gca<br>Lys Glu Ala Asp Leu Pro Leu Thr Val Thr Glu Asn Met Phe Cys Ala<br>                     1005                     1010                     1015 | 3616 |
| ggt tac aag aag gga cgt tat gat gcc tgc agt ggg gac agt gga gga<br>Gly Tyr Lys Lys Gly Arg Tyr Asp Ala Cys Ser Gly Asp Ser Gly Gly<br>                     1020                     1025                     1030 | 3664 |
| cct tta gtg ttt gct gat gat tcc cgt acc gaa agg cgg tgg gtc ttg<br>Pro Leu Val Phe Ala Asp Asp Ser Arg Thr Glu Arg Arg Trp Val Leu<br>                     1035                     1040                     1045 | 3712 |
| gaa ggg att gtc agc tgg ggc agt ccc agt gga tgt ggc aag gcg aac<br>Glu Gly Ile Val Ser Trp Gly Ser Pro Ser Gly Cys Gly Lys Ala Asn<br>                     1050                     1055                     1060 | 3760 |
| cag tac ggg ggc ttc act aaa gtt aac gtt ttc ctg tca tgg att agg<br>Gln Tyr Gly Gly Phe Thr Lys Val Asn Val Phe Leu Ser Trp Ile Arg<br>1065                    1070                     1075                     1080<br>cag ttc att tgaaactgat ctaaatattt taagcatggt tataaacgtc<br>Gln Phe Ile | 3808<br><br>3857 |
| ttgttcctat tattgcttta ctggtttaac ccataagaag gttaacgggg taaggcacaa | 3917 |
| ggatcattgt ttctgtttgt ttttacaaat ggttctttta gtcagtgaat gagaatagta | 3977 |
| tccattggag actgttacct tttattctac cttttatat tactatgcaa gtatttggga | 4037 |
| tatcttctac acatgaaaat tctgtcattt taccataaat ttggtttctg gtgtgtgtgt | 4097 |
| taagtccacc actagagaac gatgtaattt tcaatagtac atgaaataaa tatagaacaa | 4157 |

```
atctattata aaaaaaaaaa aaaaa                                              4182

<210> SEQ ID NO 2
<211> LENGTH: 1083
<212> TYPE: PRT
<213> ORGANISM: Carcinoscorpius rotundicauda

<400> SEQUENCE: 2
```

Met Trp Val Thr Cys Phe Asp Thr Phe Leu Phe Val Cys Glu Ser Ser
 1               5                  10                  15

Val Phe Cys Leu Leu Cys Val Trp Arg Phe Gly Phe Cys Arg Trp Arg
             20                  25                  30

Val Phe Tyr Ser Phe Pro Phe Val Lys Ser Thr Val Val Leu Leu Gln
         35                  40                  45

Cys Tyr His Tyr Ser Leu His Asn Thr Ser Lys Phe Tyr Ser Val Asn
     50                  55                  60

Pro Asp Lys Pro Glu Tyr Ile Leu Ser Gly Leu Val Leu Gly Leu Leu
 65                  70                  75                  80

Ala Gln Lys Met Arg Pro Val Gln Ser Lys Gly Val Asp Leu Gly Leu
                 85                  90                  95

Cys Asp Glu Thr Arg Phe Glu Cys Lys Cys Gly Asp Pro Gly Tyr Val
            100                 105                 110

Phe Asn Ile Pro Val Lys Gln Cys Thr Tyr Phe Tyr Arg Trp Arg Pro
        115                 120                 125

Tyr Cys Lys Pro Cys Asp Asp Leu Glu Ala Lys Asp Ile Cys Pro Lys
    130                 135                 140

Tyr Lys Arg Cys Gln Glu Cys Lys Ala Gly Leu Asp Ser Cys Val Thr
145                 150                 155                 160

Cys Pro Pro Asn Lys Tyr Gly Thr Trp Cys Ser Gly Glu Cys Gln Cys
                165                 170                 175

Lys Asn Gly Gly Ile Cys Asp Gln Arg Thr Gly Ala Cys Ala Cys Arg
            180                 185                 190

Asp Arg Tyr Glu Gly Val His Cys Glu Ile Leu Lys Gly Cys Pro Leu
        195                 200                 205

Leu Pro Ser Asp Ser Gln Val Gln Glu Val Arg Asn Pro Pro Asp Asn
    210                 215                 220

Pro Gln Thr Ile Asp Tyr Ser Cys Ser Pro Gly Phe Lys Leu Lys Gly
225                 230                 235                 240

Met Ala Arg Ile Ser Cys Leu Pro Asn Gly Gln Trp Ser Asn Phe Pro
                245                 250                 255

Pro Lys Cys Ile Arg Glu Cys Ala Met Val Ser Ser Pro Glu His Gly
            260                 265                 270

Lys Val Asn Ala Leu Ser Gly Asp Met Ile Glu Gly Ala Thr Leu Arg
        275                 280                 285

Phe Ser Cys Asp Ser Pro Tyr Tyr Leu Ile Gly Gln Glu Thr Leu Thr
    290                 295                 300

Cys Gln Gly Asn Gly Gln Trp Asn Gly Gln Ile Pro Gln Cys Lys Asn
305                 310                 315                 320

Leu Val Phe Cys Pro Asp Leu Asp Pro Val Asn His Ala Glu His Lys
                325                 330                 335

Val Lys Ile Gly Val Glu Gln Lys Tyr Gly Gln Phe Pro Gln Gly Thr
            340                 345                 350

Glu Val Thr Tyr Thr Cys Ser Gly Asn Tyr Phe Leu Met Gly Phe Asp
        355                 360                 365

-continued

```
Thr Leu Lys Cys Asn Pro Asp Gly Ser Trp Ser Gly Ser Gln Pro Ser
    370                 375                 380
Cys Val Lys Val Ala Asp Arg Glu Val Asp Cys Asp Ser Lys Ala Val
385                 390                 395                 400
Asp Phe Leu Asp Asp Val Gly Glu Pro Val Arg Ile His Cys Pro Ala
                405                 410                 415
Gly Cys Ser Leu Thr Ala Gly Thr Val Trp Gly Thr Ala Ile Tyr His
            420                 425                 430
Glu Leu Ser Ser Val Cys Arg Ala Ala Ile His Ala Gly Lys Leu Pro
        435                 440                 445
Asn Ser Gly Gly Ala Val His Val Val Asn Asn Gly Pro Tyr Ser Asp
    450                 455                 460
Phe Leu Gly Ser Asp Leu Asn Gly Ile Lys Ser Glu Glu Leu Lys Ser
465                 470                 475                 480
Leu Ala Arg Ser Phe Arg Phe Asp Tyr Val Ser Ser Ser Thr Ala Gly
                485                 490                 495
Lys Ser Gly Cys Pro Asp Gly Trp Phe Glu Val Asp Glu Asn Cys Val
            500                 505                 510
Tyr Val Thr Ser Lys Gln Arg Ala Trp Glu Arg Ala Gln Gly Val Cys
        515                 520                 525
Thr Asn Met Ala Ala Arg Leu Ala Val Leu Asp Lys Asp Val Ile Pro
    530                 535                 540
Asn Ser Leu Thr Glu Thr Leu Arg Gly Lys Gly Leu Thr Thr Thr Trp
545                 550                 555                 560
Ile Gly Leu His Arg Leu Asp Ala Glu Lys Pro Phe Ile Trp Glu Leu
                565                 570                 575
Met Asp Arg Ser Asn Val Val Leu Asn Asp Asn Leu Thr Phe Trp Ala
            580                 585                 590
Ser Gly Glu Pro Gly Asn Glu Thr Asn Cys Val Tyr Met Asp Ile Gln
        595                 600                 605
Asp Gln Leu Gln Ser Val Trp Lys Thr Lys Ser Cys Phe Gln Pro Ser
    610                 615                 620
Ser Phe Ala Cys Met Met Asp Leu Ser Asp Arg Asn Lys Ala Lys Cys
625                 630                 635                 640
Asp Asp Pro Gly Ser Leu Glu Asn Gly His Ala Thr Leu His Gly Gln
                645                 650                 655
Ser Ile Asp Gly Phe Tyr Ala Gly Ser Ser Ile Arg Tyr Ser Cys Glu
            660                 665                 670
Val Leu His Tyr Leu Ser Gly Thr Glu Thr Val Thr Cys Thr Thr Asn
        675                 680                 685
Gly Thr Trp Ser Ala Pro Lys Pro Arg Cys Ile Lys Val Ile Thr Cys
    690                 695                 700
Gln Asn Pro Pro Val Pro Ser Tyr Gly Ser Val Glu Ile Lys Pro Pro
705                 710                 715                 720
Ser Arg Thr Asn Ser Ile Ser Arg Val Gly Ser Pro Phe Leu Arg Leu
                725                 730                 735
Pro Arg Leu Pro Leu Pro Leu Ala Arg Ala Ala Lys Pro Pro Pro Lys
            740                 745                 750
Pro Arg Ser Ser Gln Pro Ser Thr Val Asp Leu Ala Ser Lys Val Lys
        755                 760                 765
Leu Pro Glu Gly His Tyr Arg Val Gly Ser Arg Ala Ile Tyr Thr Cys
    770                 775                 780
```

-continued

| | | | | | | | | | | | | |
|---|---|---|---|---|---|---|---|---|---|---|---|---|
|Glu|Ser|Arg|Tyr|Tyr|Glu|Leu|Leu|Gly|Ser|Gln|Gly|Arg|Arg|Cys|Asp|
|785| | | |790| | | |795| | | |800|

Ser Asn Gly Asn Trp Ser Gly Arg Pro Ala Ser Cys Ile Pro Val Cys
            805                 810                 815

Gly Arg Ser Asp Ser Pro Arg Ser Pro Phe Ile Trp Asn Gly Asn Ser
        820                 825                 830

Thr Glu Ile Gly Gln Trp Pro Trp Gln Ala Gly Ile Ser Arg Trp Leu
    835                 840                 845

Ala Asp His Asn Met Trp Phe Leu Gln Cys Gly Gly Ser Leu Leu Asn
850                 855                 860

Glu Lys Trp Ile Val Thr Ala Ala His Cys Val Thr Tyr Ser Ala Thr
865                 870                 875                 880

Ala Glu Ile Ile Asp Pro Asn Gln Phe Lys Met Tyr Leu Gly Lys Tyr
                885                 890                 895

Tyr Arg Asp Asp Ser Arg Asp Asp Tyr Val Gln Val Arg Glu Ala
            900                 905                 910

Leu Glu Ile His Val Asn Pro Asn Tyr Asp Pro Gly Asn Leu Asn Phe
        915                 920                 925

Asp Ile Ala Leu Ile Gln Leu Lys Thr Pro Val Thr Leu Thr Thr Arg
    930                 935                 940

Val Gln Pro Ile Cys Leu Pro Thr Asp Ile Thr Thr Arg Glu His Leu
945                 950                 955                 960

Lys Glu Gly Thr Leu Ala Val Val Thr Gly Trp Gly Leu Asn Glu Asn
                965                 970                 975

Asn Thr Tyr Ser Glu Thr Ile Gln Gln Ala Val Leu Pro Val Val Ala
            980                 985                 990

Ala Ser Thr Cys Glu Glu Gly Tyr Lys Glu Ala Asp Leu Pro Leu Thr
        995                 1000                1005

Val Thr Glu Asn Met Phe Cys Ala Gly Tyr Lys Lys Gly Arg Tyr Asp
    1010                1015                1020

Ala Cys Ser Gly Asp Ser Gly Gly Pro Leu Val Phe Ala Asp Asp Ser
1025                1030                1035                1040

Arg Thr Glu Arg Arg Trp Val Leu Glu Gly Ile Val Ser Trp Gly Ser
                1045                1050                1055

Pro Ser Gly Cys Gly Lys Ala Asn Gln Tyr Gly Gly Phe Thr Lys Val
            1060                1065                1070

Asn Val Phe Leu Ser Trp Ile Arg Gln Phe Ile
        1075                1080

<210> SEQ ID NO 3
<211> LENGTH: 3448
<212> TYPE: DNA
<213> ORGANISM: Carcinoscorpius rotundicauda
<220> FEATURE:
<221> NAME/KEY: CDS
<222> LOCATION: (18)..(3074)

<400> SEQUENCE: 3

```
gtgaaggtaa cttaagt atg gtc tta gcg tcg ttt ttg gtg tct ggt tta        50
                   Met Val Leu Ala Ser Phe Leu Val Ser Gly Leu
                     1               5                  10 gtt cta ggg cta cta gcc caa aaa atg cgc cca gtt cag tcc aaa gga       98
Val Leu Gly Leu Leu Ala Gln Lys Met Arg Pro Val Gln Ser Lys Gly
         15                  20                  25 gta gat cta ggc ttg tgt gat gaa acg agg ttc gag tgt aag tgt ggc      146
Val Asp Leu Gly Leu Cys Asp Glu Thr Arg Phe Glu Cys Lys Cys Gly
     30                  35                  40
```

-continued

```
gat cca ggc tat gtg ttc aac att cca gtg aaa caa tgt aca tac ttt        194
Asp Pro Gly Tyr Val Phe Asn Ile Pro Val Lys Gln Cys Thr Tyr Phe
         45                  50                  55 tat cga tgg agg ccg tat tgt aaa cca tgt gat gac ctg gag gct aag        242
Tyr Arg Trp Arg Pro Tyr Cys Lys Pro Cys Asp Asp Leu Glu Ala Lys
 60                  65                  70                  75 gat att tgt cca aag tac aaa cga tgt caa gag tgt aag gct ggt ctt        290
Asp Ile Cys Pro Lys Tyr Lys Arg Cys Gln Glu Cys Lys Ala Gly Leu
                     80                  85                  90 gat agt tgt gtt act tgt cca cct aac aaa tat ggt act tgg tgt agc        338
Asp Ser Cys Val Thr Cys Pro Pro Asn Lys Tyr Gly Thr Trp Cys Ser
                 95                 100                 105 ggt gaa tgt cag tgt aag aat gga ggt atc tgt gac cag agg aca gga        386
Gly Glu Cys Gln Cys Lys Asn Gly Gly Ile Cys Asp Gln Arg Thr Gly
             110                 115                 120 gct tgt gca tgt cgt gac aga tat gaa ggg gtg cac tgt gaa att ctc        434
Ala Cys Ala Cys Arg Asp Arg Tyr Glu Gly Val His Cys Glu Ile Leu
         125                 130                 135 aaa ggt tgt cct ctt ctt cca tcg gat tct cag gtt cag gaa gtc aga        482
Lys Gly Cys Pro Leu Leu Pro Ser Asp Ser Gln Val Gln Glu Val Arg
140                 145                 150                 155 aat cca cca gat aat ccc caa act att gac tac agc tgt tca cca ggg        530
Asn Pro Pro Asp Asn Pro Gln Thr Ile Asp Tyr Ser Cys Ser Pro Gly
                 160                 165                 170 ttc aag ctt aag ggt atg gca cga att agc tgt ctc cca aat gga cag        578
Phe Lys Leu Lys Gly Met Ala Arg Ile Ser Cys Leu Pro Asn Gly Gln
             175                 180                 185 tgg agt aac ttt cca ccc aaa tgt att cga gaa tgt gcc atg gtt tca        626
Trp Ser Asn Phe Pro Pro Lys Cys Ile Arg Glu Cys Ala Met Val Ser
         190                 195                 200 tct cca gaa cat ggg aaa gtg aat gct ctt agt ggt gat atg ata gaa        674
Ser Pro Glu His Gly Lys Val Asn Ala Leu Ser Gly Asp Met Ile Glu
     205                 210                 215 ggg gct act tta cgg ttc tca tgt gat agt ccc tac tac ttg att ggt        722
Gly Ala Thr Leu Arg Phe Ser Cys Asp Ser Pro Tyr Tyr Leu Ile Gly
220                 225                 230                 235 caa gaa aca tta acc tgt cag ggt aat ggt cag tgg aat gga cag ata        770
Gln Glu Thr Leu Thr Cys Gln Gly Asn Gly Gln Trp Asn Gly Gln Ile
                 240                 245                 250 cca caa tgt aag aac ttg gtc ttc tgt cct gac ctg gat cct gta aac        818
Pro Gln Cys Lys Asn Leu Val Phe Cys Pro Asp Leu Asp Pro Val Asn
             255                 260                 265 cat gct gaa cac aag gtt aaa att ggt gtg gaa caa aaa tat ggt cag        866
His Ala Glu His Lys Val Lys Ile Gly Val Glu Gln Lys Tyr Gly Gln
         270                 275                 280 ttt cct caa ggc act gaa gtg acc tat acg tgt tcg ggt aac tac ttc        914
Phe Pro Gln Gly Thr Glu Val Thr Tyr Thr Cys Ser Gly Asn Tyr Phe
     285                 290                 295 ttg atg ggt ttt gac acc tta aaa tgt aac cct gat ggg tct tgg tca        962
Leu Met Gly Phe Asp Thr Leu Lys Cys Asn Pro Asp Gly Ser Trp Ser
300                 305                 310                 315 gga tca cag cca tcc tgt gtt aaa gtg gca gac aga gag gtc gac tgt       1010
Gly Ser Gln Pro Ser Cys Val Lys Val Ala Asp Arg Glu Val Asp Cys
                 320                 325                 330 gac agt aaa gct gta gac ttc ttg gat gat gtt ggt gaa cct gtc agg       1058
Asp Ser Lys Ala Val Asp Phe Leu Asp Asp Val Gly Glu Pro Val Arg
             335                 340                 345 atc cac tgt cct gct ggc tgt tct ttg aca gct ggt act gtg tgg ggt       1106
Ile His Cys Pro Ala Gly Cys Ser Leu Thr Ala Gly Thr Val Trp Gly
```

-continued

```
           350                 355                 360
aca gcc ata tac cat gaa ctt tcc tca gtg tgt cgt gca gcc atc cat   1154
Thr Ala Ile Tyr His Glu Leu Ser Ser Val Cys Arg Ala Ala Ile His
        365                 370                 375 gct ggc aag ctt cca aac tct gga gga gcg gtg cat gtt gtg aac aat   1202
Ala Gly Lys Leu Pro Asn Ser Gly Gly Ala Val His Val Val Asn Asn
380                 385                 390                 395 ggc ccc tac tcg gac ttt ctg ggt agt gac ctg aat ggg ata aaa tcg   1250
Gly Pro Tyr Ser Asp Phe Leu Gly Ser Asp Leu Asn Gly Ile Lys Ser
                400                 405                 410 gaa gag ttg aag tct ctt gcc cgg agt ttc cga ttc gat tat gtc cgt   1298
Glu Glu Leu Lys Ser Leu Ala Arg Ser Phe Arg Phe Asp Tyr Val Arg
            415                 420                 425 tcc tcc aca gca ggt aaa tca gga tgt cct gat gga tgg ttt gag gta   1346
Ser Ser Thr Ala Gly Lys Ser Gly Cys Pro Asp Gly Trp Phe Glu Val
                430                 435                 440 gac gag aac tgt gtg tac gtt aca tca aaa cag aga gcc tgg gaa aga   1394
Asp Glu Asn Cys Val Tyr Val Thr Ser Lys Gln Arg Ala Trp Glu Arg
    445                 450                 455 gct caa ggt gtg tgt acc aat atg gct gct cgt ctt gct gtg ctg gac   1442
Ala Gln Gly Val Cys Thr Asn Met Ala Ala Arg Leu Ala Val Leu Asp
460                 465                 470                 475 aaa gat gta att cca aat tcg ttg act gag act cta cga ggg aaa ggg   1490
Lys Asp Val Ile Pro Asn Ser Leu Thr Glu Thr Leu Arg Gly Lys Gly
                480                 485                 490 tta aca acc acg tgg ata gga ttg cac aga cta gat gct gag aag ccc   1538
Leu Thr Thr Thr Trp Ile Gly Leu His Arg Leu Asp Ala Glu Lys Pro
            495                 500                 505 ttt att tgg gag tta atg gat cgt agt aat gtg gtt ctg aat gat aac   1586
Phe Ile Trp Glu Leu Met Asp Arg Ser Asn Val Val Leu Asn Asp Asn
        510                 515                 520 cta aca ttc tgg gcc tct ggc gaa cct gga aat gaa act aac tgt gta   1634
Leu Thr Phe Trp Ala Ser Gly Glu Pro Gly Asn Glu Thr Asn Cys Val
    525                 530                 535 tat atg gac atc caa gat cag ttg cag tct gtg tgg aaa acc aag tca   1682
Tyr Met Asp Ile Gln Asp Gln Leu Gln Ser Val Trp Lys Thr Lys Ser
540                 545                 550                 555 tgt ttt cag ccc tca agt ttt gct tgc atg atg gat ctg tca gac aga   1730
Cys Phe Gln Pro Ser Ser Phe Ala Cys Met Met Asp Leu Ser Asp Arg
                560                 565                 570 aat aaa gcc aaa tgc gat gat cct gga tca ctg gaa aat gga cac gcc   1778
Asn Lys Ala Lys Cys Asp Asp Pro Gly Ser Leu Glu Asn Gly His Ala
            575                 580                 585 aca ctt cat gga caa agt att gat ggg ttc tat gct ggt tct tct ata   1826
Thr Leu His Gly Gln Ser Ile Asp Gly Phe Tyr Ala Gly Ser Ser Ile
        590                 595                 600 agg tac agc tgt gag gtt ctc cac tac ctc agt gga act gaa acc gta   1874
Arg Tyr Ser Cys Glu Val Leu His Tyr Leu Ser Gly Thr Glu Thr Val
    605                 610                 615 act tgt aca aca aat ggc aca tgg agt gct cct aaa cct cga tgt atc   1922
Thr Cys Thr Thr Asn Gly Thr Trp Ser Ala Pro Lys Pro Arg Cys Ile
620                 625                 630                 635 aaa gtc atc acc tgc caa aac ccc cct gta cca tca tat ggt tct gtg   1970
Lys Val Ile Thr Cys Gln Asn Pro Pro Val Pro Ser Tyr Gly Ser Val
                640                 645                 650 gaa atc aaa ccc cca agt cgg aca aac tcg ata agt cgt gtt ggg tca   2018
Glu Ile Lys Pro Pro Ser Arg Thr Asn Ser Ile Ser Arg Val Gly Ser
            655                 660                 665 cct ttc ttg agg ttg cca cgg tta ccc ctc cca tta gct aga gca gcc   2066
```

```
                    Pro Phe Leu Arg Leu Pro Arg Leu Pro Leu Pro Leu Ala Arg Ala Ala
                                670                 675                 680 aaa cct cct cca aaa cct aga tcc tca caa ccc tct act gtg gac ttg           2114
Lys Pro Pro Pro Lys Pro Arg Ser Ser Gln Pro Ser Thr Val Asp Leu
685                 690                 695 gct tct aaa gtt aaa cta cct gaa ggt cat tac cgg gta ggg tct cga           2162
Ala Ser Lys Val Lys Leu Pro Glu Gly His Tyr Arg Val Gly Ser Arg
700                 705                 710                 715 gcc atc tac acg tgc gag tcg aga tac tac gaa cta ctt gga tct caa           2210
Ala Ile Tyr Thr Cys Glu Ser Arg Tyr Tyr Glu Leu Leu Gly Ser Gln
                720                 725                 730 ggc aga aga tgt gac tct aat gga aac tgg agt ggt cgg cca gcg agc           2258
Gly Arg Arg Cys Asp Ser Asn Gly Asn Trp Ser Gly Arg Pro Ala Ser
            735                 740                 745 tgt att cca gtt tgt gga cgg tca gac tct cct cgt tct cct ttt atc           2306
Cys Ile Pro Val Cys Gly Arg Ser Asp Ser Pro Arg Ser Pro Phe Ile
        750                 755                 760 tgg aat ggg aat tct aca gaa ata ggt cag tgg ccg tgg cag gca gga           2354
Trp Asn Gly Asn Ser Thr Glu Ile Gly Gln Trp Pro Trp Gln Ala Gly
    765                 770                 775 atc tct aga tgg ctt gca gac cac aat atg tgg ttt ctc cag tgt gga           2402
Ile Ser Arg Trp Leu Ala Asp His Asn Met Trp Phe Leu Gln Cys Gly
780                 785                 790                 795 gga tct cta ttg aat gag aaa tgg atc gtc act gct gcc cac tgt gtc           2450
Gly Ser Leu Leu Asn Glu Lys Trp Ile Val Thr Ala Ala His Cys Val
                800                 805                 810 acc tac tct gct act gct gag att att gac ccc aat cag ttt aaa atg           2498
Thr Tyr Ser Ala Thr Ala Glu Ile Ile Asp Pro Asn Gln Phe Lys Met
            815                 820                 825 tat ctg ggc aag tac tac cgt gat gac agt aga gac gat gac tat gta           2546
Tyr Leu Gly Lys Tyr Tyr Arg Asp Asp Ser Arg Asp Asp Asp Tyr Val
        830                 835                 840 caa gta aga gag gct ctt gag atc cac gtg aat cct aac tac gac ccc           2594
Gln Val Arg Glu Ala Leu Glu Ile His Val Asn Pro Asn Tyr Asp Pro
    845                 850                 855 ggc aat ctc aac ttt gac ata gcc cta att caa ctg aaa act cct gtt           2642
Gly Asn Leu Asn Phe Asp Ile Ala Leu Ile Gln Leu Lys Thr Pro Val
860                 865                 870                 875 act ttg aca aca cga gtc caa cca atc tgt ctg cct act gac atc aca           2690
Thr Leu Thr Thr Arg Val Gln Pro Ile Cys Leu Pro Thr Asp Ile Thr
                880                 885                 890 aca aga gaa cac ttg aag gag gga aca tta gca gtg gtg aca ggt tgg           2738
Thr Arg Glu His Leu Lys Glu Gly Thr Leu Ala Val Val Thr Gly Trp
            895                 900                 905 ggt ttg aat gaa aac aac acc tat tca gag acg att caa caa gct gtg           2786
Gly Leu Asn Glu Asn Asn Thr Tyr Ser Glu Thr Ile Gln Gln Ala Val
        910                 915                 920 cta cct gtt gtt gca gcc agc acc tgt gaa gag ggg tac aag gaa gca           2834
Leu Pro Val Val Ala Ala Ser Thr Cys Glu Glu Gly Tyr Lys Glu Ala
    925                 930                 935 gac tta cca ctg aca gta aca gag aac atg ttc tgt gca ggt tac aag           2882
Asp Leu Pro Leu Thr Val Thr Glu Asn Met Phe Cys Ala Gly Tyr Lys
940                 945                 950                 955 aag gga cgt tat gat gcc tgc agt ggg gac agt gga gga cct tta gtg           2930
Lys Gly Arg Tyr Asp Ala Cys Ser Gly Asp Ser Gly Gly Pro Leu Val
                960                 965                 970 ttt gct gat gat tcc cgt acc gaa agg cgg tgg gtc ttg gaa ggg att           2978
Phe Ala Asp Asp Ser Arg Thr Glu Arg Arg Trp Val Leu Glu Gly Ile
            975                 980                 985
```

-continued

| | |
|---|---|
| gtc agc tgg ggc agt ccc agt gga tgt ggc aag gcg aac cag tac ggg<br>Val Ser Trp Gly Ser Pro Ser Gly Cys Gly Lys Ala Asn Gln Tyr Gly<br>990                       995                     1000 | 3026 |
| ggc ttc act aaa gtt aac gtt ttc ctg tca tgg att agg cag ttc att<br>Gly Phe Thr Lys Val Asn Val Phe Leu Ser Trp Ile Arg Gln Phe Ile<br>1005                     1010                     1015 | 3074 |
| tgaaactgat ctaaatattt taagcatggt tataaacgtc ttgtttccta ttattgcttt | 3134 |
| actagtttaa cccataagaa ggttaactgg gtaaggcaca aggatcattg tttctgtttg | 3194 |
| tttttacaaa tggttatttt agtcagtgaa tgagaatagt atccattgaa gactgttacc | 3254 |
| ttttattcta cctttttata ttactatgta agtatttggg atatcttcta cacatgaaaa | 3314 |
| ttctgtcatt ttaccataaa tttggtttct ggtgtgtgct aagtccacca gtagagaacg | 3374 |
| atgtaatttt cactagcaca tgaaataaat atagaacaaa tctattataa actaccttaa | 3434 |
| aaaaaaaaaa aaaa | 3448 |

<210> SEQ ID NO 4
<211> LENGTH: 1019
<212> TYPE: PRT
<213> ORGANISM: Carcinoscorpius rotundicauda

<400> SEQUENCE: 4

Met Val Leu Ala Ser Phe Leu Val Ser Gly Leu Val Leu Gly Leu Leu
1               5                   10                 15

Ala Gln Lys Met Arg Pro Val Gln Ser Lys Gly Val Asp Leu Gly Leu
              20                   25                   30

Cys Asp Glu Thr Arg Phe Glu Cys Lys Cys Gly Asp Pro Gly Tyr Val
             35                   40                   45

Phe Asn Ile Pro Val Lys Gln Cys Thr Tyr Phe Tyr Arg Trp Arg Pro
50                     55                   60

Tyr Cys Lys Pro Cys Asp Asp Leu Glu Ala Lys Asp Ile Cys Pro Lys
65                    70                   75                   80

Tyr Lys Arg Cys Gln Glu Cys Lys Ala Gly Leu Asp Ser Cys Val Thr
              85                   90                   95

Cys Pro Pro Asn Lys Tyr Gly Thr Trp Cys Ser Gly Glu Cys Gln Cys
              100                 105                110

Lys Asn Gly Gly Ile Cys Asp Gln Arg Thr Gly Ala Cys Ala Cys Arg
              115                120                125

Asp Arg Tyr Glu Gly Val His Cys Glu Ile Leu Lys Gly Cys Pro Leu
130                   135                140

Leu Pro Ser Asp Ser Gln Val Gln Glu Val Arg Asn Pro Pro Asp Asn
145                   150                  155                 160

Pro Gln Thr Ile Asp Tyr Ser Cys Ser Pro Gly Phe Lys Leu Lys Gly
                165                170                175

Met Ala Arg Ile Ser Cys Leu Pro Asn Gly Gln Trp Ser Asn Phe Pro
              180                 185                190

Pro Lys Cys Ile Arg Glu Cys Ala Met Val Ser Ser Pro Glu His Gly
              195                200                205

Lys Val Asn Ala Leu Ser Gly Asp Met Ile Glu Gly Ala Thr Leu Arg
              210                215                220

Phe Ser Cys Asp Ser Pro Tyr Tyr Leu Ile Gly Gln Glu Thr Leu Thr
225                   230                  235                 240

Cys Gln Gly Asn Gly Gln Trp Asn Gly Gln Ile Pro Gln Cys Lys Asn
              245                250                255

Leu Val Phe Cys Pro Asp Leu Asp Pro Val Asn His Ala Glu His Lys

-continued

```
            260                 265                 270
Val Lys Ile Gly Val Glu Gln Lys Tyr Gly Gln Phe Pro Gln Gly Thr
            275                 280                 285
Glu Val Thr Tyr Thr Cys Ser Gly Asn Tyr Phe Leu Met Gly Phe Asp
            290                 295                 300
Thr Leu Lys Cys Asn Pro Asp Gly Ser Trp Ser Gly Ser Gln Pro Ser
305                 310                 315                 320
Cys Val Lys Val Ala Asp Arg Glu Val Asp Cys Asp Ser Lys Ala Val
                        325                 330                 335
Asp Phe Leu Asp Asp Val Gly Glu Pro Val Arg Ile His Cys Pro Ala
                340                 345                 350
Gly Cys Ser Leu Thr Ala Gly Thr Val Trp Gly Thr Ala Ile Tyr His
            355                 360                 365
Glu Leu Ser Ser Val Cys Arg Ala Ala Ile His Ala Gly Lys Leu Pro
            370                 375                 380
Asn Ser Gly Gly Ala Val His Val Val Asn Asn Gly Pro Tyr Ser Asp
385                 390                 395                 400
Phe Leu Gly Ser Asp Leu Asn Gly Ile Lys Ser Glu Glu Leu Lys Ser
                        405                 410                 415
Leu Ala Arg Ser Phe Arg Phe Asp Tyr Val Arg Ser Ser Thr Ala Gly
                420                 425                 430
Lys Ser Gly Cys Pro Asp Gly Trp Phe Glu Val Asp Glu Asn Cys Val
            435                 440                 445
Tyr Val Thr Ser Lys Gln Arg Ala Trp Glu Arg Ala Gln Gly Val Cys
            450                 455                 460
Thr Asn Met Ala Ala Arg Leu Ala Val Leu Asp Lys Asp Val Ile Pro
465                 470                 475                 480
Asn Ser Leu Thr Glu Thr Leu Arg Gly Lys Gly Leu Thr Thr Thr Trp
                        485                 490                 495
Ile Gly Leu His Arg Leu Asp Ala Glu Lys Pro Phe Ile Trp Glu Leu
                500                 505                 510
Met Asp Arg Ser Asn Val Val Leu Asn Asp Asn Leu Thr Phe Trp Ala
            515                 520                 525
Ser Gly Glu Pro Gly Asn Glu Thr Asn Cys Val Tyr Met Asp Ile Gln
            530                 535                 540
Asp Gln Leu Gln Ser Val Trp Lys Thr Lys Ser Cys Phe Gln Pro Ser
545                 550                 555                 560
Ser Phe Ala Cys Met Met Asp Leu Ser Asp Arg Asn Lys Ala Lys Cys
                        565                 570                 575
Asp Asp Pro Gly Ser Leu Glu Asn Gly His Ala Thr Leu His Gly Gln
                580                 585                 590
Ser Ile Asp Gly Phe Tyr Ala Gly Ser Ser Ile Arg Tyr Ser Cys Glu
            595                 600                 605
Val Leu His Tyr Leu Ser Gly Thr Glu Thr Val Thr Cys Thr Thr Asn
            610                 615                 620
Gly Thr Trp Ser Ala Pro Lys Pro Arg Cys Ile Lys Val Ile Thr Cys
625                 630                 635                 640
Gln Asn Pro Pro Val Pro Ser Tyr Gly Ser Val Glu Ile Lys Pro Pro
                        645                 650                 655
Ser Arg Thr Asn Ser Ile Ser Arg Val Gly Ser Pro Phe Leu Arg Leu
                660                 665                 670
Pro Arg Leu Pro Leu Pro Leu Ala Arg Ala Ala Lys Pro Pro Pro Lys
            675                 680                 685
```

```
Pro Arg Ser Ser Gln Pro Ser Thr Val Asp Leu Ala Ser Lys Val Lys
            690                 695                 700
Leu Pro Glu Gly His Tyr Arg Val Gly Ser Arg Ala Ile Tyr Thr Cys
705                     710                 715                 720
Glu Ser Arg Tyr Tyr Glu Leu Leu Gly Ser Gln Gly Arg Arg Cys Asp
                    725                 730                 735
Ser Asn Gly Asn Trp Ser Gly Arg Pro Ala Ser Cys Ile Pro Val Cys
                740                 745                 750
Gly Arg Ser Asp Ser Pro Arg Ser Pro Phe Ile Trp Asn Gly Asn Ser
            755                 760                 765
Thr Glu Ile Gly Gln Trp Pro Trp Gln Ala Gly Ile Ser Arg Trp Leu
            770                 775                 780
Ala Asp His Asn Met Trp Phe Leu Gln Cys Gly Gly Ser Leu Leu Asn
785                     790                 795                 800
Glu Lys Trp Ile Val Thr Ala Ala His Cys Val Thr Tyr Ser Ala Thr
                    805                 810                 815
Ala Glu Ile Ile Asp Pro Asn Gln Phe Lys Met Tyr Leu Gly Lys Tyr
                820                 825                 830
Tyr Arg Asp Asp Ser Arg Asp Asp Tyr Val Gln Val Arg Glu Ala
            835                 840                 845
Leu Glu Ile His Val Asn Pro Asn Tyr Asp Pro Gly Asn Leu Asn Phe
    850                 855                 860
Asp Ile Ala Leu Ile Gln Leu Lys Thr Pro Val Thr Leu Thr Thr Arg
865                     870                 875                 880
Val Gln Pro Ile Cys Leu Pro Thr Asp Ile Thr Thr Arg Glu His Leu
                    885                 890                 895
Lys Glu Gly Thr Leu Ala Val Val Thr Gly Trp Gly Leu Asn Glu Asn
                900                 905                 910
Asn Thr Tyr Ser Glu Thr Ile Gln Gln Ala Val Leu Pro Val Val Ala
            915                 920                 925
Ala Ser Thr Cys Glu Glu Gly Tyr Lys Glu Ala Asp Leu Pro Leu Thr
    930                 935                 940
Val Thr Glu Asn Met Phe Cys Ala Gly Tyr Lys Lys Gly Arg Tyr Asp
945                     950                 955                 960
Ala Cys Ser Gly Asp Ser Gly Gly Pro Leu Val Phe Ala Asp Asp Ser
                    965                 970                 975
Arg Thr Glu Arg Arg Trp Val Leu Glu Gly Ile Val Ser Trp Gly Ser
                980                 985                 990
Pro Ser Gly Cys Gly Lys Ala Asn Gln Tyr Gly Gly Phe Thr Lys Val
            995                 1000                1005
Asn Val Phe Leu Ser Trp Ile Arg Gln Phe Ile
    1010                1015
```